United States Patent
Bellevergue et al.

(10) Patent No.: US 8,436,011 B2
(45) Date of Patent: May 7, 2013

(54) PYRIDINOPYRIDINONE DERIVATIVES, PREPARATION THEREOF AND THERAPEUTIC USE THEREOF

(75) Inventors: Patrice Bellevergue, Paris (FR); Gilbert Lassalle, Paris (FR); Gary McCort, Paris (FR); Valerie Martin, Paris (FR); Pierre Savi, Paris (FR); Cecile Volle-Challier, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/985,749

(22) Filed: Jan. 6, 2011

(65) Prior Publication Data
US 2011/0124643 A1 May 26, 2011

Related U.S. Application Data

(63) Continuation of application No. PCT/FR2009/051321, filed on Jul. 6, 2009.

(30) Foreign Application Priority Data

Jul. 8, 2008 (FR) .................................. 08 03862

(51) Int. Cl.
*A61K 31/4375* (2006.01)
*C07D 471/06* (2006.01)

(52) U.S. Cl.
USPC .......................................... 514/300; 546/122

(58) Field of Classification Search ................. 546/122; 514/300
See application file for complete search history.

(56) References Cited

U.S. PATENT DOCUMENTS

| | | | |
|---|---|---|---|
| 8,263,614 B2 | 9/2012 | Alam et al. | |
| 2010/0144757 A1 | 6/2010 | Alam et al. | |

FOREIGN PATENT DOCUMENTS

| FR | 2917412 | | 12/2008 |
|---|---|---|---|
| FR | 2917413 | | 12/2008 |
| WO | WO 2005/026156 | | 3/2005 |
| WO | WO-2005/026156 A1 * | 3/2005 | |
| WO | 2008/121687 | | 10/2008 |
| WO | WO 2010/004197 A3 | | 1/2010 |

OTHER PUBLICATIONS

Carroll, M., et al., The TEL/Platelet-Derived Growth Factor B Receptor (PDGFBR) Fusion in Chronic Myelomonocytic Leukemia is a Transforming Protein That Self-Associates and Activates PDGFBR Kinase-Dependent Signaling Pathways, Proc. Natl. Acad. Sci. USA, vol. 93, pp. 14845-14850, (1996).
Cools, J., et al., The EOL-1 Cell Line as an In Vitro Model for the Study of FIP1L1-PDGFRA-Positive Chronic Eosinophilic Leukemia, Blood, vol. 103, No. 7, (2004), pp. 2802-2805.
Fukushima, H., et al., Synthesis and Structure-Activity Relationships of Potent 3- and 4-Substituted-2-Cyanoprrolidine Dipeptidyl Peptidase IV Inhibitors, Bioorganic & Medicinal Chemistry, vol. 12, (2004), pp. 6053-6061.
Giroux, A., et al., One Pot Biaryl Synthesis via in Situ Boronate Formation, Tetrahedron Letters, vol. 38, No. 22, pp. 3841-3844, (1997).
Vuorinen, K., et al., Imatinib Mesylate Inhibits Fibrogenesis in Asbestos-Induced Interstitial Pneumonia, Experimental Lung Research, vol. 33, pp. 357-373, (2007).
Jones, G., et al., Triazolopyridines. 18.1 Nucleophilic Substitution Reactions on Triazolopyridines; A New Route to 2,2'-Bipyridines, Tetrahedron, vol. 53, No. 24, pp. 8257-8268, (1997).
O'Farrell, A.-M., et al., SU11248 is a Novel FLT3 Tyrosine Kinase Inhibitor With Potent Activity In Vitro and In Vivo, Blood, (2003), vol. 101, No. 9, pp. 3597-3605.
Olah, G. A., et al., Synthetic Methods and Reactions; IV. Fluorination of Carboxylic Acids with Cyanuric Fluoride, Synthesis, (1973) pp. 487-488.
Spiekermann, K., et al., The Protein Tyrosine Kinase Inhibitor SU5614 Inhibits FLT3 and Induces Growth Arrest and Apoptosis in AML-Derived Cell Lines Expressing a Constitutively Activated FLT3, Blood, vol. 101, No. 4, (2003), pp. 1494-1504.
Supuran, C. T., et al., Protein Tyrosine Kinase Inhibitors as Anticancer Agents. Expert Opin. Ther. Patents, (2004), vol. 14, No. 1, pp. 35-53.
Ishiyama, T., et al., Palladium(0)-Catalyzed Cross-Coupling Reaction of Alkoxydibron With Haloarenes: A Direct Procedure for Arylboronic Esters, J. Org. Chem., vol. 60, pp. 7508-7510, (1995).
Ishikawa, N., et al., Preparation of Carboxylic Acid Fluorides Using Hexafluoro-1,2-Epoxypropane, Chem. Lett., (1976) pp. 1407-1408.
Mukaiyama, T., et al., A Convenient Method for the Preparation of Carboxylic Acid Fluorides, Chem. Lett., (1976) pp. 303-306.
Abramsson, et al., Endothelial and nonendothelial sources of PDGF-B regulate pericyte recruitment and influence vascular pattern formation in tumors, J. Clin. Invest 112, 1142-1151, (2003).

(Continued)

*Primary Examiner* — Kamal Saeed
*Assistant Examiner* — Janet L Coppins
(74) *Attorney, Agent, or Firm* — Janann Y. Ali

(57) ABSTRACT

The present invention relates to pyridopyridone derivatives of formula (I):

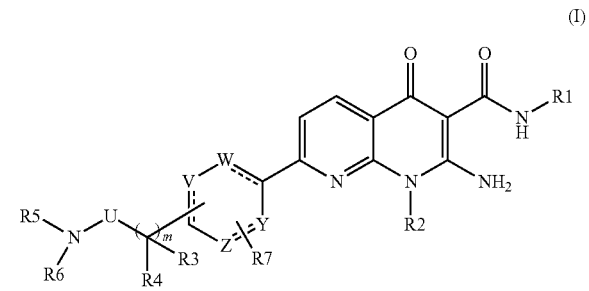

in which the variables are as defined herein, to their preparation and to their therapeutic use as inhibitors of the kinase activity of PDGF (platelet-derived growth factor) ligand receptors and possibly of FLT3 (fms-like tyrosine kinase receptor) ligand receptors.

13 Claims, No Drawings

OTHER PUBLICATIONS

Aono, et al., Imatinib as a novel antifibrotic agent in bleomycin-induced pulmonary fibrosis in mice, Am. J. Respir. Crit Care Med. 171, 1279-1285, (2005).
Apte, et al., Targeting the platelet-derived growth factor receptor in antivascular therapy for human ovarian carcinoma. Clin. Cancer Res. 10, 897-908, (2004).
Bergers, et al., Benefits of targeting both pericytes and endothelial cells in the tumor vasculature with kinase inhibitors, J. Clin. Invest 111, 1287-1295, (2003).
Bonner, Regulation of PDGF and its receptors in fibrotic diseases, Cytokine Growth Factor Rev. 15, 255-273, (2004).
Borkham-Kamphorst, et al., Pro-fibrogenic potential of PDGF-D in liver fibrosis, J. Hepatol. 46, 1064-1074, (2007).
Bouzin, et al., Targeting tumor stroma and exploiting mature tumor vasculature to improve anti-cancer drug delivery, Drug Resist. Updat. 10, 109-120, (2007).
Cao, Direct role of PDGF-BB in lymphangiogenesis and lymphatic metastasis, Cell Cycle 4, 228-230, (2005).
Cao, et al., Angiogenesis stimulated by PDGF-CC, a novel member in the PDGF family, involves activation of PDGFR-alphaalpha and -alphabeta receptors, FASEB J. 16, 1575-1583, (2002).
Carow, et al., Expression of the hematopietic growth factor receptor FLT3 (STK-1/Flk2) in human leukemias, Blood 87, 1089-1096, (1996).
Chin, et al., K252a inhibits proliferation of glioma cells by blocking platelet-derived growth factor signal transduction, Clin. Cancer Res. 3, 771-776, (1997).
Claesson-Welsh, Platelet-derived growth factor receptor signals, J. Biol. Chem. 269, 32023-32026, (1994).
Corless, et al., Biology of gastrointestinal stromal tumors, J. Clin. Oncol. 22, 3813-3825, (2004).
Corless, et al., PDGFRA mutation in gastrointestinal stromal tumors: frequency, spectrum and in vitro sensitivity to imatinib, J. Clin. Oncol. 23, 5357-5364, (2005).
Deguchi, et al., Inhibitory effects of trapidil on PDGF signaling in balloon-injured rat carotid artery, Life Sci. 65, 2791-2799, (1999).
Eitner, et al., Expression of a novel PDGF isoform, PDGF-C, in normal and diseased rat kidney, J. Am. Soc. Nephrol. 13, 910-917, (2002).
Eitner, et al., PDGF-C is a proinflammatory cytokine that mediates renal interstitial fibrosis, J. Am. Soc. Nephrol. 19, 281-289, (2008).
Ferns, et al., Inhibition of neointimal smooth muscle accumulation after angioplasty by an antibody to PDGF, Science 253, 1129-1132, (1991).
Fons, et al., VEGF-R2 and neuropilin-1 are involved in VEGF-A-induced differentiation of human bone marrow progenitor cells, J. Cell Physiol 200, 351-359, (2004).
Geng, et al., STI571 (Gleevec) improves tumor growth delay and survival in irradiated mouse models of glioblastoma, Int. J. Radiat. Oncol. Biol. Phys. 64, 263-271, (2006).
Griffin, et al., Discovery of a fusion kinase in EOL-1 cells and idiopathic hypereosinophilic syndrome, Proc. Natl. Acad. Sci. U. S. A. 100, 7830-7835, (2003).
Griffon-Etienne, et al., Taxane-induced apoptosis decompresses blood vessels and lowers interstitial fluid pressure in solid tumors: clinical implications. Cancer Res. 59, 3776-3782, (1999).
Heldin, Structural and functional studies on platelet-derived growth factor, EMBO J. 11, 4251-4259, (1992).
Hellstrom, et al., Lack of pericytes leads to endothelial hyperplasia and abnormal vascular morphogenesis, J. Cell Biol. 153, 543-553, (2001).
Hellstrom, et al., Role of PDGF-B and PDGFR-beta in recruitment of vascular smooth muscle cells and pericytes during embryonic blood vessel formation in the mouse, Development 126, 3047-3055, (1999).
Heuchel, et al., Platelet-derived growth factor beta receptor regulates interstitial fluid homeostasis through phosphatidylinositol-3' kinase signaling, Proc. Natl. Acad. Sci. U. S. A 96, 11410-11415, (1999).
Hwang, et al., Inhibition of platelet-derived growth factor receptor phosphorylation by STI571 (Gleevec) reduces growth and metastasis of human pancreatic carcinoma in an orthotopic nude mouse model, Clin. Cancer Res. 9, 6534-6544, (2003).
Kelly, et al., FLT3 internal tandem duplication mutations associated with human acute myeloid leukemias induce myeloproliferative disease in a murine bone marrow transplant model, Blood 99, 310-318, (2002).
Kim, et al., Simultaneous blockade of platelet-derived growth factor-receptor and epidermal growth factor-receptor signaling and systemic administration of paclitaxel as therapy for human prostate cancer metastasis in bone of nude mice, Cancer Res. 64, 4201-4208, (2004).
Le Tourneau, et al., Sunitnib: a novel tyrosine kinase inhibitor. A brief review of its therapeutic potential in the treatment of renal carcinoma and gastrointestinal stromal tumors (GIST), Ther. Clin. Risk Manag. 3, 341-348, (2007).
Levis, et al., Novel FLT3 tyrosine kinase inhibitors, Expert. Opin. Investig. Drugs 12, 1951-1962, (2003).
Lindner, Expression of platelet-derived growth factor ligands and receptors by rat aortic endothelium in vivo, Pathobiology 63, 257-264, (1995).
Merchant, et al., Potential use of imatinib in Ewing's Sarcoma: evidence for in vitro and in vivo activity, J. Natl. Cancer Inst. 94, 1673-1679, (2002).
Mizuki, et al., Flt3 mutations from patients with acute myeloid leukemia induce transformation of 32D cells mediated by the Ras and STAT5 pathways, Blood 96, 3907-3914, (2000).
Neef, et al., Oral imatinib treatment reduces early fibrogenesis but does not prevent progression in the long term, J. Hepatol. 44, 167-175, (2006).
Pietras, et al., Functions of paracrine PDGF signaling in the proangiogenic tumor stroma revealed by pharmacological targeting, PLOS, Med. 5, e19, (2008).
Pietras, et al., Inhibition of PDGF receptor signaling in tumor stroma enhances antitumor effect of chemotherapy, Cancer Res. 62, 5476-5484, (2002).
Pietras, et al., PDGF receptors as cancer drug targets, Cancer Cell 3, 439-443, (2003).
Ritchie, et al., The Tel-PDGFRbeta fusion gene produces a chronic myeloproliferative syndrome in transgenic mice, Leukemia 13, 1790-1803, (1999).
Rosnet, et al., Human FLT3/FLK2 gene: cDNA cloning and expression in hematopoietic cells, Blood 82, 1110-1119, (1993).
Ross, Platelet-derived growth factor, Annu. Rev. Med. 38, 71-79, (1987).
Rovida, et al., ERK5 differentially regulates PDGF-induced proliferation and migration of hepatic stellate cells, J. Hepatol.48, 107-115,(2008).
Schermuly, et al., Reversal of experimental pulmonary hypertension by PDGF inhibition, J. Clin Invest 115, 2811-2821, (2005).
Sirois, et al., Antisense oligonucleotide inhibition of PDGFR-beta receptor subunit expression directs suppression of intimal thickening, Circulation 95, 669-676, (1997).
Sjoblom, et al., Growth inhibition of dermatofibrosarcoma protuberans tumors by the platelet-derived growth factor receptor antagonist STI571 through induction of apoptosis, Cancer Res. 61, 5778-5783, (2001).
Strawn, et al., Inhibition of glioma cell growth by a truncated platelet-derived growth factor-beta receptor, J. Biol. Chem. 269, 21215-21222, (1994).
Tse, et al., Constitutive activation of FLT3 stimulates multiple intracellular signal transducers and results in transformation, Leukemia 14, 1766-1776, (2000).
Uehara, et al., Effects of blocking platelet-derived growth factor-receptor signaling in a mouse model of experimental prostate cancer bone metastases, J. Natl. Cancer Inst. 95, 458-470, (2003).
Ullrich, et al., Signal transduction by receptors with tyrosine kinase activity, Cell 61, 203-212, (1990).
Uren, et al., Beta-platelet-derived growth factor receptor mediates motility and growth of Ewing's sarcoma cells, Oncogene 22, 2334-2342, (2003).
Weiss, et al., Switching signals on or off by receptor dimerization, Cell 94, 277-280, (1998).

Yu, et al., Platelet-derived growth factor (PDGF) receptor-alpha-activated c-Jun NH2-terminal kinase-1 is critica for PDGF-induced p21WAF1/CIP1 promoter activity independent of p53, J. Biol. Chem. 278, 49582-49588, (2003).

Yu, et al., Platelet-derived growth factor signaling and human cancer, J. Biochem. Mol. Biol. 36, 49-59, (2003).

Zwerner, et al., PDGF-C is an EWS/FLI induced transforming growth factor in Ewing family tumors, Oncogene 20, 626-633, (2001).

Drexler, Expression of FLT3 receptor and response to FLT3 ligand by leukemia cells, Leukemia 10, 588-599 (1996).

McArthur, Molecular targeting of dermatofibrosarcoma protuberans: a new approach to a surgical disease, J. Natl. Compr. Canc. Netw. 5, 557-562, (2007).

Medeiros, et al., KIT-negative gastrointestinal stromal tumors: proof of concept and therapeutic implications, Am. J. Surg. Pathol. 28, 889-894, (2004).

Stacchini, et al., Expression of type III receptor tyrosine kinases FLT3 and KIT and responses to their ligands by acute myeloid leukemia blasts, Leukemia 10, 1584-1591, (1996).

U.S. Appl. No. 13/477,778, Lassalle, et al.

U.S. Appl. No. 13/539,706, filed Jul. 2, 2012, Arylsulfonamide Pyridine-Pyridinone Derivatives, Preparation of Same, and Therapeutic Use Thereof.

Van Leuben, et al., One-Step Conversion of Aldehydes to Nitrites Introduction of a One-Carbon Unit, Synthetic Communications, vol. 10, No. 5, pp. 399-403, (1980).

Stille, et al., Stereospecific Cross-Coupling of Vinyl Halides With Vinyl Tin Reagents Catalyzed by Palladium, J. Am. Chem. Soc., vol. 109, pp. 813-817, (1987).

Miyaura, et al., Palladium-Catalyzed Cross-Coupling Reactions of Organoboron Compounds, Chem Rev., 1995 (95) 7 pp. 2457-2483.

Whitten, et al., [2-(Trimethylsilyl)ethoxy]methyl (SEM) as a Novel and Effective Imidazole and Fused Aromatic Imidazole Protecting Group, J. Org. Chem., (1986), vol. 51, pp. 1891-1894.

Kaur, etl al., Corneal Stroma PGDF Blockade and Myolibroblast Development Experimental Eye Research, vol. 88, (2009), pp. 960-965.

Jo, et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, (2006), pp. 2036-2053.

Dell, et al., The Role of PDGF Receptor Inhibitors and PI3-Kinase Signaling in the Pathogenesis of Corneal Neovascularization, Investigative Ophthalmology & Visual Science, (2006), vol. 47, No. 5, pp. 1926-1937.

* cited by examiner

PYRIDINOPYRIDINONE DERIVATIVES, PREPARATION THEREOF AND THERAPEUTIC USE THEREOF

The present invention relates to pyridopyridone derivatives substituted in position 7 with an aryl or heteroaryl, which is itself optionally substituted with a unit of the type —[C(R3)(R4)]$_m$-U—N(R5)(R6), to their preparation and to their therapeutic use as inhibitors of the kinase activity of PDGF (platelet-derived growth factor) ligand receptors and possibly of FLT3 (fms-like tyrosine kinase receptor) ligand receptors.

FLT3 and PDGF-R receptors are members of class III of the family of tyrosine kinase receptors (TKR), in which the receptor of Stem cell factor (c-kit) and of M-CSF (c-fms) are also included. They are characterized by an extracellular domain composed of five immunoglobulin-like domains containing the ligand-binding region and a transmembrane domain, and an intracellular part composed of a juxtamembrane domain and a kinase domain split in two by an insert domain (split domain) (Ullrich & Schlessinger, 1990).

Binding of the ligands to TKRs induces dimerization of the receptors and activation of their tyrosine kinase part, which leads to transphosphorylation of the tyrosine residues (Weiss & Schlessinger, 1998). These phosphorylated residues thus serve as a point of attachment to the intracellular signalling proteins, which, finally, bring about various cell responses: cell maintenance, division, proliferation, differentiation or migration (Claesson-Welsh, 1994).

The gene coding for FLT3 is located on chromosome 13q12 (Rosnet et al., 1992) and codes for the FLT3 protein (CD135 antigen) expressed specifically by the haematopoietic cells and more particularly the immature cells, for instance the haematopoietic stem cells and the myeloid and lymphoid multipotent progenitors, and its expression disappears in the course of haematopoietic differentiation. Its ligand, the FLT3 ligand, induces dimerization of the receptor, followed by autophosphorylation of the intracellular part of the receptor, which leads to activation of the signalling cascade. The effects of activation of the receptor with its ligand are the survival and expansion of the multipotent progenitors.

Two isoforms of PDGF receptors have been revealed, the PDGF-Rα chain and the PDGF-Rβ chain, which, following binding of their ligands, homo- or heterodimerize and induce intracellular signalling. The PDGF receptors are essentially expressed by cells of mesenchymal origin and are especially found on fibroblasts, smooth muscle cells, pericytes and glial cells (Ross et al., 1986, Heldin, 1992).

Platelet-derived growth factor, PDGF, a protein with a molecular weight of about 30 000 daltons, is secreted essentially by platelets, and secondarily by the endothelium, vascular smooth muscles and monocytes. It is formed of two polypeptide chains linked together via disulfide bridges forming either homodimers or heterodimers. Four genes (7p22, 22q13, 4q31 and 11q22) have been described as coding for four different polypeptide chains (A, B, C and D), which, once dimerized, give five biologically active ligands PDGF-AA, BB, CC, DD and AB (for a review, see: Yu et al., 2003). Binding specificity exists, especially including PDGF-AA for the alpha isoform of the receptor, PDGF-D for the BB form, and PDGF-C for the alpha and alpha/beta form. The PDGF ligands are powerful mitogens, but are also involved in cell migration, survival, apoptosis and transformation phenomena.

Inhibitors of the function of PDGF-R alpha, beta and FLT3 intervene in various therapeutic fields. Among the physiopathological phenomena in which these receptors may be involved are liquid cancers or leukaemias, solid cancers with or without metastases targeting tumour cells and/or cells of the tumoural environment (vascular cells, fibroblasts), fibroses and vascular diseases:

A. Liquid Cancers

Leukaemias are of different types and affect either the myeloid compartment or the lymphoid compartment.

The expression of FLT3 in leukaemic cells derived from acute myeloid leukaemias (AML) is of the order of 100% of cases, and FLT3 thus contributes towards stimulating the survival and proliferation of leukaemic cells (Carow et al., 1996; Drexler et al., 1996, Stacchini et al., 1996).

Furthermore, FLT3 is the site of activating mutations in 22% to 30% of adult AMLs and 11% of infant AMLs. It is most frequently a case of tandem duplications (ITD) in the transmembrane region of the receptor (more particularly exons 14 and 15). These mutations conserve the reading frame and their size may range between 18 and 111 base pairs. More readily, in about 7% of AMLs, a point mutation at residue D835 located in the kinase domain is found. In the majority of cases, the FLT3 ITD forms have a greater risk of relapse and are markers of a low prognosis of survival. These two types of mutation lead to constitutive activity of the kinase domain independent of stimulation by the ligand, and have been shown as transforming haematopoietic cells in vitro and in vivo (Mizuki et al., 2000; Tse et al; 2000). Kelly et al. (2002), have elegantly shown, in a model of bone marrow reconstitution in mice, that FLT3 ITD causes a myeloproliferative syndrome.

The value of using inhibitors of tyrosine kinase activity has been reported both in vitro and in vivo by several teams, and recently, in the model of FLT3 ITD bone marrow reconstitution, such an inhibitor has been shown to be capable of inducing regression of the tumour and of increasing the survival of the animals (O'Farrell, 2003).

Furthermore, recent data show the value of combining such inhibitors with cytotoxic agents such as daunorubicin (Levis et al., 2004).

Interestingly, blastic cells of AML type can also overexpress other receptors with kinase activity, for instance c-kit or PDGF-R.

Myeloproliferative/Dysplastic Syndromes

Quite often, cytogenetic abnormalities following chromosomal translocations have been reported in myeloproliferative syndromes. These rearrangements generate deregulated fusion proteins with tyrosine kinase activity that are involved in the proliferation of blastic myeloid cells.

Fusion Proteins with PDGF-Rβ Kinase Activity

Fusion proteins with PDGF-Rβ kinase activity are constituted of the intracellular part of PDGF-Rβ and, on the other hand, of an N-terminal domain of another protein (in general a transcription factor). The following have especially been reported in chronic myelomonocytic leukaemias (CMML): Rab5/PDGF-Rβ, H4-PDGF-Rβ, HIP1-PDGF-RB or Tel/PDGF-Rβ. The latter is the one most commonly represented. It is derived from the t(5;12)(q31;p12) translocation and encodes a fusion protein constituted of the N-terminal part of the Tel transcription factor and the C-terminal part of PDGF-Rβ. An oligomerization domain present in the Tel part leads to a dimerized form of the fusion protein and to constitutive activity of the kinase domain. This protein has been shown in vitro as being capable of transforming haematopoietic cells in several instances and especially in detailed manner in the article by M. Carroll et al. (PNAS, 1996, 93, 14845-14850). In vivo, this fusion protein leads to a syndrome of hyperproliferation of myeloid cells (Ritchie et al., 1999).

Furthermore, in animals and also clinically in man, it has been shown that inhibitors of tyrosine kinase activity inhibit the proliferation of blastic cells and make it possible to eliminate the leukaemogenesis process.

Fusion Proteins with PDGF-Rα Activity

Two fusion proteins involving PDGF-Rα have been reported: bcr-PDGF-Rα present in an atypic chronic myeloid leukaemia (CML) and FIP1L1-PDGF-Rα found in a subpopulation of leukaemias, the LEO "eosinophilic leukaemias", originating from hypereosinophilic syndrome (Griffin et al., 2003). This fusion protein bears constitutive activity of the kinase domain of PDGF-Rα and is responsible for the anarchic proliferation of these cells.

Inhibitors of the kinase activity of PDGF-Rα have shown efficacy on the proliferation of positive FIP1L1-PDGF-Rα cells, and an inhibitory compound has recently received an indication for HES/CELs.

Thus, inhibiting the kinase activity of PDGF-R alpha and beta and the FLT3 wt and FLT3ITD activity, as do the compounds of the invention, proves to be of therapeutic interest for AMLs.

Besides AMLs and myeloproliferative syndromes, it may be interesting to target other leukaemias with such inhibitors, including ALL-Bs and ALL-Ts (acute lymphoid leukaemias-B or -T), in which FLT3 is also expressed. Furthermore, by means of the normal expression of FLT3 on haematopoietic stem cells and the demonstration of its expression on leukaemic stem cells, inhibitors of the kinase activity of FLT3 may prove to be of interest in all leukaemias (including CMLs) in which the role of the leukaemic stem cells in recidivism where resistance is involved.

B. Solid Cancers

Inhibitors of the tyrosine kinase activity of the PDGF-R alpha and beta receptors may be of interest for solid cancers, either by directly targeting the tumour cell, which, by autocrine or paracrine activity, is sensitive to the TK-inhibiting activity of PDGF-R, or by targeting the cells of the environment by destabilizing the network to promote association with other therapeutic agents.

Examples of Solid Cancers Whose Target is the Tumour Cell

Soft-Tissue Cancers: Ewing's Sarcoma

Ewing's sarcoma is a form of bone cancer that mainly affects children and young adults (the average age is 13). It concerns 10% of primary bone tumours and the risk of metastases is high. It is a rare tumour affecting 2 to 3 persons per million inhabitants per year. The tumour cells are characterized by a t(11;22) chromosomal translocation encoding the EWS/FLI1 fusion protein.

The cells responsible are those of the mesenchyme, which express the PDGF-Rβ receptor that induces the motility and growth of the Ewing's sarcoma cells under stimulation by PDGF-BB (Üren et al., 2003). Furthermore, Zwerner and May (2001) have demonstrated the expression of PDGF-C by Ewing's sarcoma cells.

These same cells also express the c-kit TKR receptor, and it has been shown that an inhibitor of the kinase activity of PDGF-R and c-kit is capable of inhibiting the tumoural growth of Ewing's sarcoma lines in a model of xenograft in mice (Merchant et al., 2002).

Connective Tissue Tumour (Gist, Dermatofibrosarcoma)

GISTs (Gastrointestinal Stromal Tumours)

The Fletcher group (2004) investigated the 15% of GISTs in which KIT is neither mutated nor overexpressed (KIT-wt). These authors observed strong overexpression of the PDGF-Rα receptor. This situation is found in about a third of these GIST KIT-wt. As regards mutations of PDGF-RA, the authors observe these (35%) in cases where KIT is normal. The mutated PDGF-RAs have high and constitutive tyrosine kinase activity and affect the aspartic acid in position 842. In the same way as for Ewing's sarcomas, two inhibitors of the kinase activity of c-kit and PDGF-R have shown efficacy in vitro and in vivo on the proliferation of mutated PDGF-Rα cells (Le Tourneau et al., 2007; Corless et al., 2005).

Dermatofibrosarcomas (Darier-Ferrand's or Protuberans or DFSP)

Darier-Ferrand's dermatofibrosarcoma (or DFSP) is a dermal tumour with fusiform cells of intermediate malignancy characterized by a slow evolution with a major risk of recidivism in the case of insufficient exeresis. A genetic anomaly present in 95% of cases was discovered in 1990, with the demonstration especially of translocation of chromosomes 17 and 22 t(17-22)(q22; q13), which results in fusion of the genes COL1A1 and PDGF B and the large quantity of PDGF B overexpresses its tyrosine kinase receptor, PDGF R. Inhibiting the kinase activity of PDGF-R is a promising therapy since, in vitro, this leads to inhibition of tumour cell proliferation and apoptosis, and, in vivo, this allows a reduction of tumoural growth in tumour graft models in immunodeficient mice (Sjöblom T. et al., 2001). Furthermore, clinical studies have shown the efficacy (complete or total remission) of such a molecule in DFSPs (for a review, see McArthur, 2007).

Gliomas and Glioblastomas

Glioblastomas are the most widespread and most aggressive brain tumours, with a median survival of about one year. PDGFs and its receptors (alpha and beta) are frequently expressed in gliomas. The possibility exists that an autocrine/paracrine loop may contribute towards the pathogenicity of these tumours. The PDGF-Rα receptor is preferentially expressed in the tumour cells, whereas the PDGF-beta receptor is preferentially expressed in the vascular endothelial cells of the tumour. Blocking the kinase activity of PDGF-R has shown efficacy 1) in vitro by decreasing the number of colonies in soft agar and inhibiting the proliferation of cell lines, 2) on reducing the tumoural growth in graft models in nude mice, and 3) in combination with irradiation in models of intracranial graft of cells of glioblastoma lines (Oerbel et al., 2006; Geng et al., 2005, Strawn et al., 1994 Chin et al., 1997).

Thus, the compounds of the invention are of interest for Ewing's sarcoma, GIST and dermatofibrosarcomas, but also for desmoid tumours, haemangiomas and other fibrosarcomas for which PDGF-R expression data exist.

C. Targeting PDGF-R in the Tumoural Environment

Angiogenesis

The cells of the tumoural environment form an integral part of the development of cancer, whether in the case of a primary or secondary tumour (metastases). Among the cells of the environment that express PDGF-R and for which the role of this receptor has been demonstrated, the wall cells of vessels, i.e. the pericytes and smooth muscle cells, but also activated fibroblasts, are included.

Angiogenesis is a process of generation of new blood vessels from pre-existing vessels or by mobilization and differentiation of bone marrow cells. Thus, uncontrolled proliferation of endothelial cells and mobilization of angioblasts from the bone marrow are simultaneously observed in the processes of neovascularization of tumours. It has been shown in vitro and in vivo that several growth factors stimulate endothelial proliferation, for instance VEGF and FGFs. Besides these mechanisms, it has also been demonstrated that the wall cells such as the pericytes and smooth muscle cells participate in stabilizing the newly formed vessels. Invalidation of PDGF-Rβ causes a deficit of pericytes in mice and leads to the death of the animals at the end of gestation due to microhaemorrhages and oedemas (Hellström et al., 1999, Hellström et al., 2001). In an elegant study of transplantation, the expression of PDGF-Rβ by pericytes was shown to be necessary for their recruitment by the tumour vessels via the retention of PDGF-B by the endothelial cells, but also by the PDGF-B secreted by the tumour cells (Abramsson et al., 2003). In the transgenic model Rip1Tag2 of pancreatic tumour, Song et al. also showed the expression of PDGF-Rβ on the perivascular progenitors in the marrow derived from the bone marrow, these progenitors differentiating into mature pericytes around the tumour.

The value of blocking the activity of PDGF-R on the tumoural pericytes was demonstrated by the use of an inhibitor of the tyrosine kinase activity of PDGF-R in animal models (transgenic model of pancreatic tumour and implementation of gliomal tumour), and the effect on the tumoural growth is found to be profound in association with an inhibitor of the kinase activity of VEGF-R (Bergers et al., 2003). Literature data (Cao et al., 2002, Fons et al., 2004) have demonstrated the intervention of PDGF-Rα and of PDGF-C in angiogenesis and in the differentiation of the endothelial progenitors towards cells such as pericytes and smooth muscle cells.

Activated Fibroblasts

PDGF-R is abundant in the tumoural stroma and is found on activated fibroblasts (myofibroblasts). It has been shown in two studies that association of PDGF-R inhibitors or antagonists with cytotoxic agents leads to a decrease in the microdensity of vessels in ovarian cancers (Apte et al., 2004) and pancreatic cancers (Hwang et al., 2003). PDGF-Rβ regulates the pressure of the interstitial tissue of the tumour (Heuchel et al., 1999) and the co-administration of PDGF-R inhibitors and of chemotherapy agents improves their delivery into tumour cells by reducing the intratumoural pressure (Griffon-Etienne, 1999). Finally, in a murine model, the administration of an inhibitor of the kinase activity of PDGF-R improves the consumption of chemotherapy agents by the tumour and thus increases their efficacy (Griffon-Etienne, 1999; Pietras et al., 2002; Pietras et al., 2003). These effects are undoubtedly the effect of TAFs (tumour-associated fibroblasts), also known as CAFs (carcinoma-associated fibroblasts), which are activated fibroblasts present around the tumour and which express PDGF-R, as illustrated by the recent investigations of Hwang et al. (2008), Kain et al. (2008) and Pietras et al. (2008) in in vivo models of pancreatic cancer and cervical carcinogenesis. Stimulation with the PDGF ligand produced by the tumour cells stimulates the fibroblasts, which produce extracellular matrix and thus increase the interstitial tension. Thus, reducing this tension can facilitate the delivery of drugs into the tumour and hence increase their efficacy. Activated fibroblasts present in the tumoural stroma thus represent a new therapeutic target in oncology (for a review, see Bouzin & Feron, 2007).

Metastases

Several studies indicate that the PDGF-R and PDGF-ligand pair is involved in the development of metastases, undoubtedly by virtue of their action on angiogenesis and metastatization by the blood circulation, but also by means of a direct effect on lymphangiogenesis and thus the metastases disseminated by the lymphatic vessels. A review in particular documents the direct role of PDGF-BB in lymphangiogenesis and lymphatic metastases (Cao et al., 2005). However, the majority of the studies involve the expression of PDGF-R in the environment of the metastases that promote the taking and development of secondary tumours. The example most frequently reported is the development of bone metastases.

Example of Prostate Cancer:

Bone is frequently the site of metastases. 85% to 100% of patients who die from prostate cancer have bone metastases. Chemotherapy improves the survival without progression and the overall survival, but, on account of the extreme heterogeneity of bone metastases within the same patient, chemotherapy is not curative. It has been shown using a model of immunodeficient mice that PDGF-BB plays an important role in the in vivo development of osteoblastic bone metastases (Yu et al., 2003). PDGF-DD, for its part, accelerates the growth of prostate tumour cells and increases their interaction with stromal cells. Expression of the PDGF alpha and beta receptor has been demonstrated in 62% and 75%, respectively, of prostate cancers. Furthermore, an immunohistochemical study has shown that the prostate tumour and its metastases express PDGF-R (Hwang et al., 2003). Kim et al. (2003) have shown that PDGF-R is expressed on bone metastases and the vascular endothelial cells dependent on the metastases. A tyrosine kinase inhibitor of PDGF-R combined with a cytotoxic agent substantially reduces the bone metastases of prostate cancer in a murine model (Uehara et al., 2003). Furthermore, this same combination leads to apoptosis of the tumour cells and of the vascular endothelial cells and to inhibition of growth of the tumour cells in the bone. Blocking these receptors and their signalling pathways in bone constitutes a new therapeutic approach (Hwang et al., 2003; Uehara et al., 2003). In man, clinical studies have shown that gains can be had by the combination of PDGF-R inhibitor and of cytotoxic agent in the case of patients suffering from hormone-resistant prostate cancers with bone metastases. A decrease in the marker (prostate-specific antigen) PSA>50% has in fact been observed in 38% of patients. The mean duration of the PSA response was 8 months and the duration of survival without progression was 11 months.

In the light of these various studies, it appears that the compounds of the invention are of value for the treatment of solid cancers by virtue of their effect on the cells of the environment, in combination with other therapeutic agents such as cytotoxic agents or angiogenesis inhibitors.

D. Fibroses

Fibroses are often the cause of a primary event such as a cancer, radiotherapy treatment, hepatitis or alcoholism. The involvement of PDGF is clearly demonstrated in pulmonary fibrosis (including asbestosis), renal fibrosis (glomerulonephritis) and medullary fibrosis (often associated with leukaemias with megakaryocytes), induced by radiotherapy, and also hepatic and pancreatic fibrosis (associated with alcoholism or hepatitis) (for a review, see J. C. Bonner, 2004). Overexpression of PDGF has, in particular, clearly been shown, and results in in vivo models with inhibitors of the TK activity of PDGF-R have also been reported. Among these studies, that of Einter et al. (2002) has shown that PDGF-CC is a powerful inducer of renal fibrosis. The authors tested the efficacy of a neutralizing antibody in a model of unilateral urethral ligation, in which the fibrosis develops particularly quickly. They observed a very pronounced antifibrosing effect with a reduction in the accumulation of myofibroblasts, a reduction in the accumulation of extracellular matrix and a reduction in collagen IV deposits. Another study conducted on a model of bleomycin-induced pulmonary fibrosis in mice showed the efficacy of an inhibitor of the TK activity of PDGF-R on the prevention of fibrosis by inhibition of the proliferation of mesenchymal cells (Aono et al., 2005). In a model of asbestos-induced fibrosis, a PDGF-R TK inhibitor reduced the progression of fibrosis in the pulmonary parenchyma and the deposit of collagen (Vuorinen K., Gao F., Oury T. D., Kinnula V. L., Myllärniemi M. Imatinib mesylate inhibits fibrogenesis in asbestos-induced interstitial pneumonia. Exp. Lung Res. 2007 September; 33(7): 357-73). Several teams have demonstrated the involvement of PDGF-R in hepatic fibrosis. It is clearly shown that PDGF-BB and DD have pro-fibrogenic characteristics on hepatic stellate cells (Rovida et al., 2008; Borkham-Kamphorst et al., 2007). In vivo, a PDGF-R TK inhibitor is capable of reducing early-onset fibrogenesis in a model of bile canal ligation in rats (Neef et al., 2006).

Thus, in the light of the literature data, the compounds of the invention appear to be of therapeutic value for the various types of fibrosis.

E. Vascular Diseases: Atherosclerosis, Restenosis and Arteriosclerosis

The proliferation and migration of vascular smooth muscle cells contributes towards intimal hypertrophy of the arteries and thus plays a predominant role in atherosclerosis and restenosis after angioplasty and endoarterectomy. It has been clearly demonstrated in vitro and in vivo in animal models that PDGF is involved in these phenomena. In vivo, an increase in PDGF expression has especially been shown in a vein graft model in pigs. Furthermore, it has also been shown that an inhibitor of the TK activity of PDGF-R consequently decreases the size of the lesions of the thoracic and abdominal artery of ApoE-KO diabetic mice (animals treated with streptozotocin). Another study showed that inhibition of the signalling induced by PDGF (TK or PDGF A antisense) leads to a decrease in the formation of the neointima formation in "balloon injury" and "coronary artery restenosis" models (Deguchi J., 1999, Ferns et al, 1991, Sirois et al., 1997, Lindner et al., 1995).

Thus, inhibitors of the tyrosine kinase activity of PDGF-R, such as the compounds of the present invention, represent a therapy of choice, either alone or in combination with antagonists of other growth factors involved in these pathologies, such as FGF, in the treatment of pathologies associated with the proliferation of vascular smooth muscle cells such as atherosclerosis, post-angioplasty restenosis, or following the insertion of endovascular prostheses (stents) or during aorto-coronary bypass surgery.

By virtue of their inhibitory activity on the TK activity of PDGF-R, the compounds of the invention appear to be of value for treating these vascular diseases.

F. Others

Other pathologies appear to be liable to be indications for the compounds of the invention, including idiopathic pulmonary arterial hypertension (PAHT). PAHT, characterized by a large and continuous rise in pressure in the pulmonary artery, leads to right-ventricular insufficiency and, often, to the death of the patient. It is associated with an increase in the proliferation and migration of the smooth muscle cells of the pulmonary vessels. Schermuly et al. (2005) have shown that inhibiting the tyrosine kinase activity of the PDGF receptors considerably improves the evolution of the disease. To do this, they use, inter alia, a model of experimental pulmonary arterial hypertension in rats, obtained by the administration of monocrotaline for 28 days. All the treated rats survived, whereas 50% of them died in the untreated control group.

One subject of the present invention is compounds corresponding to formula (I):

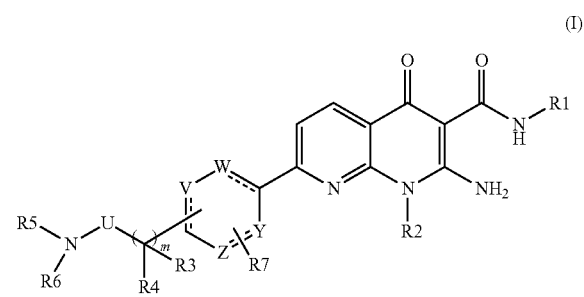

in which

R1 represents a (C1-C4)alkyl group,

R2 represents —(CH$_2$)$_{n'}$—B in which n'=0, 1, 2, 3, 4 and B is a (C3-C5)-cycloalkyl group or a (C1-C4)alkyl group optionally substituted with one or more fluorine atoms or a (C1-C4)alkoxy group, U represents a carbonyl group or a —CH$_2$— group, Y, Z, V and W represent, independently of each other, a —CH— group or a carbon atom optionally substituted with a group R7 or a heteroatom such as a nitrogen atom, a sulfur atom or an oxygen atom, or no atom, it being understood that the ring must be aromatic and be 5- or 6-membered, R3, R4 represent, independently of each other, a hydrogen atom or a linear (C1-C4)alkyl group, or R3 and R4 form, together with the carbon to which they are attached, a (C3-C5)cycloalkyl group, m is an integer equal to 1, 2, 3, 4, R5 represents a hydrogen atom or a (C1-C4)alkyl group, R6 represents —(CH$_2$)$_n$-L in which n=0, 1, 2, 3 and L is a group independently selected from the following groups:

a (C1-C5)alkyl group optionally substituted with a (C1-C4)alkoxy group, a (C3-C5)cycloalkyl group, an aryl comprising 6 carbon atoms and optionally substituted with one or more halogen atoms, a 5- or 6-membered heteroaryl including at least one heteroatom chosen from a nitrogen or sulfur atom, optionally substituted with a (C1-C4)alkyl group, a saturated heterocycle, in which the said heterocycle is 4- to 7-membered including at least one heteroatom chosen from a nitrogen atom and an oxygen atom, and is optionally substituted in any position, including on the nitrogen atom, with one or more substituents chosen from a fluorine atom, a (C1-C4) fluoroalkyl group, a linear or branched (C1-C4)alkyl group, a (C3-C5)cycloalkyl group and a (C1-C4)alkylsulfonamide group, R7 represents a hydrogen atom or a (C1-C4)alkyl group or a halogen atom.

One subject of the present invention is compounds corresponding to formula (I):

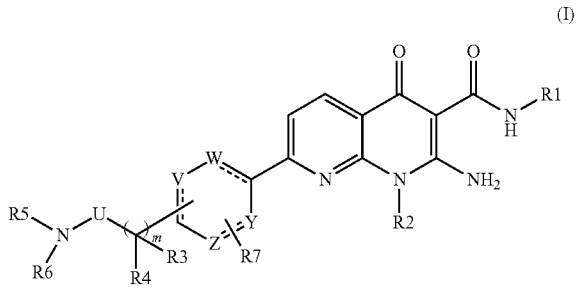

in which
R1 represents a (C1-C4)alkyl group,
R2 represents —(CH$_2$)$_{n'}$—B in which n'=0, 1, 2, 3, 4 and B is a (C3-C5)-cycloalkyl group or a (C1-C4)alkyl group optionally substituted with one or more fluorine atoms or a (C1-C4)alkoxy group,
U represents a carbonyl group or a —CH$_2$— group,
Y, Z, V and W represent, independently of each other, a —CH— group or a carbon atom optionally substituted with a group R7 or a heteroatom such as a nitrogen atom, a sulfur atom or an oxygen atom, or no atom, it being understood that the ring must be aromatic and be 5- or 6-membered,
R3, R4 represent, independently of each other, a hydrogen atom or a linear (C1-C4)alkyl group, or R3 and R4 form, together with the carbon to which they are attached, a (C3-C5)cycloalkyl group,
m is an integer equal to 1, 2, 3, 4,
R5 represents a hydrogen atom or a (C1-C4)alkyl group,
R6 represents —(CH$_2$)$_n$-L in which n=0, 1, 2, 3 and L is a group independently selected from the following groups:
  a (C1-C5)alkyl group optionally substituted with a (C1-C4)alkoxy group,
  a (C3-C5)cycloalkyl group,
  an aryl comprising 6 carbon atoms and optionally substituted with one or more halogen atoms,
  a 5- or 6-membered heteroaryl including at least one heteroatom chosen from a nitrogen or sulfur atom, optionally substituted with a (C1-C4)alkyl group,
  a saturated heterocycle, in which the said heterocycle is 5- to 7-membered including at least one heteroatom chosen from a nitrogen atom and an oxygen atom, and is optionally substituted in any position, including on the nitrogen atom, with one or more substituents chosen from a fluorine atom, a (C1-C4) fluoroalkyl group, a linear or branched (C1-C4)alkyl group, a (C3-C5)cycloalkyl group and a (C1-C4)alkylsulfonamide group,
R7 represents a hydrogen atom or a (C1-C4)alkyl group or a halogen atom.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

For example, when L represents a heterocycle, the absolute configuration of a substituted carbon on the said heterocycle may be R or S.

The compounds of formula (I) may especially exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

The compounds of formula (I) may also exist in the form of solvates, i.e. in the form of associations or combinations with one or more solvent molecules. Such solvates also form part of the invention.

In the context of the present invention, the following definitions apply:
  an alkyl group: a saturated aliphatic group containing from 1 to 7 carbon atoms (advantageously from 1 to 4 carbon atoms) and being linear or, when the alkyl chain contains at least 3 carbon atoms, possibly being branched or cyclic (including cyclization that is only partial). Examples that may be mentioned include methyl, ethyl, propyl, isopropyl, butyl, isobutyl, tert-butyl, methyl-cyclopropyl, pentyl, 2,2-dimethylpropyl, hexyl, heptyl, etc. . . . groups, and also the cycloalkyl groups defined below;
  a cycloalkyl group: a cyclic alkyl group containing from 3 to 7 carbon atoms (advantageously from 3 to 5 carbon atoms), all the carbon atoms of which are included in the ring. Mention may be made of cyclopropyl, cyclobutyl, cyclopentyl, cyclohexyl and cycloheptyl groups;
  an alkoxy group: a group —O-alkyl, in which the alkyl group is as defined above;
  a halogen atom: a fluorine, a chlorine, a bromine or an iodine;
  a haloalkyl group: a group comprising an alkyl group as defined above, one or more hydrogen atoms of which have been replaced with a halogen atom as defined above;
  a heteroatom: a nitrogen, oxygen or sulfur atom;
  an aryl group: a 6-membered monocyclic aromatic group, for example a phenyl group;
  a heteroaryl group: a 5- to 7-membered monocyclic aromatic group including between 1 and 3 heteroatoms as defined previously. Examples that may be mentioned include pyridine, pyrazine, pyrimidine, imidazole, pyrrole, thiophene and thiazole groups;
  a heterocycle: a 5- to 7-membered cyclic alkyl group including one or more heteroatoms as defined previously. Examples that may be mentioned include pyrrolidine, morpholine, piperidine and piperazine groups.

Among the compounds of formula (I) that are subjects of the invention, mention may be made of a group of compounds that is defined as follows:
R1 represents a (C1-C4)alkyl group,
and/or
R2 represents —(CH$_2$)$_{n'}$—B in which n'=0, 1 and B is a (C3-C5)cycloalkyl group or a (C1-C4)alkyl group optionally substituted with one or more fluorine atoms or a (C1-C4)alkoxy group,
and/or
U represents a carbonyl group or a —CH$_2$— group,
and/or
Y, Z, V and W represent, independently of each other, a —CH— group or a carbon atom optionally substituted with a group R7 or a heteroatom such as a nitrogen atom or a sulfur atom, or no atom, it being understood that the ring must be aromatic and be 5- or 6-membered, and/or R3, R4 represent, independently of each other, a hydrogen atom or a linear (C1-C4)alkyl group or R3 and R4 form, together with the carbon to which they are attached, a (C3-C5)cycloalkyl group, and/or m is an integer equal to 1, 2, 3, 4, and/or R5 represents a hydrogen atom or a (C1-C4)alkyl group, and/or R6 represents —$(CH_2)_n$-L in which n=0, 1, 2, 3 and L is a group independently selected from the following groups:
- a (C1-C5)alkyl group optionally substituted with a (C1-C4)alkoxy group,
- a (C3-C5)cycloalkyl group,
- an aryl comprising 6 carbon atoms and optionally substituted with one or more halogen atoms,
- a 5- or 6-membered heteroaryl including at least one heteroatom chosen from a nitrogen or sulfur atom, optionally substituted with a (C1-C4)alkyl group,
- a saturated heterocycle, in which the said heterocycle is 5- to 7-membered including at least one heteroatom chosen from a nitrogen atom and an oxygen atom, and is optionally substituted in any position, including on the nitrogen atom, with one or more substituents chosen from a fluorine atom, a (C1-C4) fluoroalkyl group, a linear or branched (C1-C4)alkyl group, a (C3-C5)cycloalkyl group and a (C1-C4)alkylsulfonamide group, and/or R7 represents a hydrogen atom or a (C1-C4)alkyl group or a halogen atom.

Among the compounds of formula (I) that are subjects of the invention, a first subgroup of compounds is constituted by the compounds for which U represents a carbonyl group.

Among the compounds of formula (I) that are subjects of the invention, a second subgroup of compounds is constituted by the compounds for which U represents a —$CH_2$— group.

Among the compounds of formula (I) that are subjects of the invention, a third subgroup of compounds is constituted by the compounds for which the ring comprising Y, Z, V and W is chosen from phenyl, pyridine, thiazole and thiophene groups.

Among the compounds of formula (I) that are subjects of the invention, a fourth subgroup of compounds is constituted by the compounds for which R3 represents a hydrogen atom.

Among the compounds of formula (I) that are subjects of the invention, a fifth subgroup of compounds is constituted by the compounds for which R4 represents a hydrogen atom.

Among the compounds of formula (I) that are subjects of the invention, a sixth subgroup of compounds is constituted by the compounds for which R5 represents a hydrogen atom.

Among the compounds of formula (I) that are subjects of the invention, a seventh subgroup of compounds is constituted by the compounds for which L represents a (C1-C5) alkyl group optionally substituted with a (C1-C4)alkoxy group.

Among the compounds of formula (I) that are subjects of the invention, an eighth subgroup of compounds is constituted by the compounds for which L represents a (C3-C5) cycloalkyl group.

Among the compounds of formula (I) that are subjects of the invention, a ninth subgroup of compounds is constituted by the compounds for which L represents a 5- or 6-membered heteroaryl group including at least one heteroatom chosen from a nitrogen or sulfur atom, optionally substituted with a (C1-C4)alkyl group. Advantageously, the heteroaryl group is chosen from pyridine, pyrazine, pyrimidine, imidazole, pyrrole and thiazole groups.

Among the compounds of formula (I) that are subjects of the invention, a tenth subgroup of compounds is constituted by the compounds for which L represents a saturated heterocycle, in which the said heterocycle is 5- to 7-membered including at least one heteroatom chosen from a nitrogen atom and an oxygen atom, and is optionally substituted in any position, including on the nitrogen atom, with one or more substituents chosen from a fluorine atom, a (C1-C4) fluoroalkyl group, a linear or branched (C1-C4)alkyl group, a (C3-C5)-cycloalkyl group and a (C1-C4)alkylsulfonamide group. Advantageously, the said heterocyclic group is chosen from pyrrolidine and morpholine groups.

Among the compounds of formula (I) that are subjects of the invention, an eleventh subgroup of compounds is constituted by the compounds for which m is equal to 1.

Among the compounds of formula (I) that are subjects of the invention, a twelfth subgroup of compounds is constituted by the compounds for which the chain —$[C(R3R4)]_m$-U—N(R5)(R6) is in the para position relative to the ring to which it is attached.

Among the compounds of formula (I) that are subjects of the invention, a thirteenth subgroup of compounds is constituted by the compounds for which the chain —$[C(R3R4)]_m$-U—N(R5)(R6) is in a meta position relative to the ring to which it is attached.

All the groups and subgroups may be used, independently of each other, in combination to obtain compounds according to the invention.

Among the combinations of groups and subgroups corresponding to compounds that are subjects of the invention, mention may be made of a first combination corresponding to compounds for which:

U represents a carbonyl group,
R3, R4 represent a hydrogen atom,
R5 represents a hydrogen atom,
R7 represents a hydrogen atom,
m is equal to 1,
and R1, R2, Y, Z, V, W, R6, n are as defined previously.

Mention may be made of a second combination corresponding to compounds according to the invention for which:

R1 represents a (C1-C4)alkyl group,
R2 represents —$(CH_2)_{n'}$—B with n'=0 or 1 and B is a (C3-C5)cycloalkyl group or a (C1-C4)alkyl group,
U represents a carbonyl group,
Y, Z, V, W represent, independently of each other, a heteroatom, a carbon atom substituted with a group R7 or a —CH— group,
R7 represents a hydrogen or halogen atom or a (C1-C4) alkyl group,
R3 represents a hydrogen atom,
R4 represents a hydrogen atom or a (C1-C4)alkyl group,
R5 represents a hydrogen atom,
R6 represents —$(CH_2)_n$-L in which L represents a group selected from the following groups:
- an aryl comprising 6 carbon atoms and optionally substituted with one or more halogen atoms,
- a 5- or 6-membered heteroaryl including at least one heteroatom chosen from a nitrogen or sulfur atom,
- a saturated heterocycle, in which the said heterocycle is 5- or 6-membered including at least one heteroatom chosen from a nitrogen atom and an oxygen atom, and is optionally substituted in any position, including on the nitrogen atom, with one or more substituents chosen from a fluorine atom, a (C1-C4) fluoroalkyl group, a (C1-C4)alkyl group and a (C3-C5)cycloalkyl group, m is equal to 1, and n is as defined previously.

Mention may be made of a third combination corresponding to compounds according to the invention for which:

R1 represents a (C1-C4)alkyl group,

R2 represents —$(CH_2)_{n'}$—B with n'=0, 1, 2, 3, 4 and B is a (C1-C4)alkyl group, U represents a carbonyl group, Y, Z, V, W represent, independently of each other, a heteroatom, a carbon atom substituted with a group R7 or a —CH— group, R7 represents a hydrogen or halogen atom or a (C1-C4) alkyl group, R3 represents a hydrogen atom, R4 represents a hydrogen atom, R5 represents a hydrogen atom, R6 represents —$(CH_2)_n$-L in which L represents a group selected from the following groups:
- an aryl comprising 6 carbon atoms and optionally substituted with one or more halogen atoms,
- a 5- or 6-membered heteroaryl including at least one heteroatom chosen from a nitrogen or sulfur atom,
- a saturated heterocycle, in which the said heterocycle is 5- or 6-membered including at least one heteroatom chosen from a nitrogen atom and an oxygen atom, and is optionally substituted in any position, including on the nitrogen atom, with one or more substituents chosen from a fluorine atom, a (C1-C4) fluoroalkyl group and a (C1-C4)alkyl group, m is equal to 1, and n is as defined previously.

Mention may be made of a fourth combination corresponding to compounds according to the invention for which:

R1 represents a (C1-C4)alkyl group,

R2 represents a group —$(CH_2)_{n'}$—B in which n'=0, 1, 2, 3, 4 and B is a (C1-C4)alkyl group, U represents a carbonyl group, Y, Z, V, W represent, independently of each other, a heteroatom or a —CH— group, R3 represents a hydrogen atom, R4 represents a hydrogen atom, R5 represents a hydrogen atom, R6 represents —$(CH_2)_n$-L in which L represents a group selected from the following groups:
- a an aryl comprising 6 carbon atoms and optionally substituted with one or more halogen atoms,
- a 5- or 6-membered heteroaryl including at least one heteroatom chosen from a nitrogen or sulfur atom,
- a saturated heterocycle, in which the said heterocycle is 5- or 6-membered including at least one heteroatom chosen from a nitrogen atom and an oxygen atom, and is optionally substituted in any position, including on the nitrogen atom, with one or more substituents chosen from a fluorine atom, a (C1-C4)alkyl group and a (C3-C5)cycloalkyl group and m and n are as defined previously.

Mention may be made of a fifth combination corresponding to compounds according to the invention for which:

R1 represents a (C1-C4)alkyl group,

R2 represents a group —$(CH_2)_{n'}$—B in which n'=0, 1, 2, 3, 4 and B is a (C1-C4)alkyl group, U represents a carbonyl group, Y, Z, V, W represent a —CH— group, R3, R4 represent a hydrogen atom, R5 represents a hydrogen atom, R7 is a hydrogen atom, R6 represents —$(CH_2)_n$-L in which L represents a linear or branched (C1-C5)alkyl group optionally substituted with a (C1-C4)alkoxy group or a (C3-C5)cycloalkyl group, m is equal to 1, and n is as defined previously.

A sixth combination corresponds to compounds according to the invention for which:

R1 represents a (C1-C4)alkyl group,

R2 represents a group —$(CH_2)_{n'}$—B in which n'=0, 1, 2, 3, 4 and B is a (C1-C4)alkyl group, U represents a carbonyl group, Y, Z, V, W represent a —CH— group, R3, R4 represent a hydrogen atom, R5 represents a hydrogen atom, R7 is a hydrogen atom, R6 represents —$(CH_2)_n$-L in which L represents an aryl group optionally substituted with one or more halogen atoms, m is equal to 1, and n is as defined previously.

A seventh combination corresponds to compounds according to the invention for which:

R1 represents a (C1-C4)alkyl group,

R2 represents —$(CH_2)_{n'}$—B with n'=0 or 1 and B is a (C3-C5)cycloalkyl group or a (C1-C4)alkyl group optionally substituted with one or more fluorine atoms, U represents a carbonyl group, Y, Z, V, W represent, independently of each other, a heteroatom, a —CH—group, a carbon atom optionally substituted with a group R7, or no atom, R3, R4 represent a hydrogen atom, or R3 and R4 form, together with the carbon to which they are attached, a (C3-C5)cycloalkyl group, R5 represents a hydrogen atom, R6 represents —$(CH_2)_n$-L in which L represents a saturated heterocyclic group optionally substituted in any position, including on the nitrogen atom, with one or more substituents chosen from a fluorine atom, a (C1-C4) fluoroalkyl group, a linear or branched (C1-C4) alkyl group, a (C3-C5)cycloalkyl group and a (C1-C4) alkylsulfonamide group, R7, m and n are as defined previously.

An eighth combination corresponds to compounds according to the invention for which:

R1 represents a (C1-C4)alkyl group,

R2 represents a group —$(CH_2)_{n'}$—B in which n'=0, 1, 2, 3, 4 and B is a (C1-C4)alkyl group optionally substituted with a (C1-C4)alkoxy group, U represents a carbonyl group, Y, Z, V, W represent, independently of each other, a heteroatom, a carbon atom or a —CH— group, R7 is a hydrogen atom, R3, R4 represent a hydrogen atom, R5 represents a hydrogen atom, R6 represents —$(CH_2)_n$-L in which L represents a heteroaryl group, optionally substituted with a (C1-C4) alkyl, m is equal to 1, and n is as defined previously.

A ninth combination corresponds to compounds according to the invention for which:

R1 represents a (C1-C4)alkyl group,

R2 represents a group —$(CH_2)_{n'}$—B in which n'=0, 1, 2, 3, 4 and B is a (C1-C4)alkyl group, U represents a —CH$_2$— group,
Y, Z, V, W represent a —CH— group,
R3, R4 represent a hydrogen atom,
R5 represents a hydrogen atom,
R6 represents —(CH$_2$)$_n$-L in which L represents a heteroaryl group,
m is equal to 1,
and n is as defined previously.

Among the compounds of formula (I) that are subjects of the invention, mention may be made especially of the following compounds:

2-amino-1-ethyl-N-methyl-4-oxo-7-{4-[2-oxo-2-(phenylamino)ethyl]-phenyl}-1,4-dihydro-1,8-naphthyridine-3-carboxamide (compound 1)

2-amino-1-ethyl-7-[4-(2-{[(1-ethylpyrrolidin-2-yl)methyl](methyl)amino}-2-oxoethyl)phenyl]-N-methyl-4-oxo-1,4-dihydro-1,8-naphthyridine-3-carboxamide (compound 2)

2-amino-1-ethyl-N-methyl-4-oxo-7-{4-[2-oxo-2-(pyrid-3-ylamino)ethyl]-phenyl}-1,4-dihydro-1,8-naphthyridine-3-carboxamide (compound 3)

2-amino-1-ethyl-N-methyl-4-oxo-7-{4-[2-oxo-2-(pyrid-2-ylamino)ethyl]-phenyl}-1,4-dihydro-1,8-naphthyridine-3-carboxamide (compound 4)

2-amino-7-(4-{2-[(2-chlorophenyl)amino]-2-oxoethyl}phenyl)-1-ethyl-N-methyl-4-oxo-1,4-dihydro-1,8-naphthyridine-3-carboxamide (compound 5)

2-amino-7-(4-{2-[(3,5-difluorophenyl)amino]-2-oxoethyl}phenyl)-1-ethyl-N-methyl-4-oxo-1,4-dihydro-1,8-naphthyridine-3-carboxamide (compound 6)

2-amino-1-ethyl-N-methyl-4-oxo-7-(4-{2-oxo-2-[(pyrid-4-ylmethyl)amino]-ethyl}phenyl)-1,4-dihydro-1,8-naphthyridine-3-carboxamide (compound 7)

2-amino-1-ethyl-N-methyl-4-oxo-7-(4-{2-oxo-2-[(pyrid-2-ylmethyl)amino]-ethyl}phenyl)-1,4-dihydro-1,8-naphthyridine-3-carboxamide (compound 8)

2-amino-1-ethyl-7-(4-{2-[(2-methoxyethyl)amino]-2-oxoethyl}phenyl)-N-methyl-4-oxo-1,4-dihydro-1,8-naphthyridine-3-carboxamide (compound 9)

2-amino-7-{4-[2-(cyclopropylamino)-2-oxoethyl]phenyl}-1-ethyl-N-methyl-4-oxo-1,4-dihydro-1,8-naphthyridine-3-carboxamide (compound 10)

2-amino-1-ethyl-N-methyl-7-(4-{2-[(1-methylethyl)amino]-2-oxoethyl}-phenyl)-4-oxo-1,4-dihydro-1,8-naphthyridine-3-carboxamide (compound 11)

2-amino-7-{4-[2-(cyclopentylamino)-2-oxoethyl]phenyl}-1-ethyl-N-methyl-4-oxo-1,4-dihydro-1,8-naphthyridine-3-carboxamide (compound 12)

2-amino-1-ethyl-N-methyl-4-oxo-7-{4-[2-oxo-2-(pyrazin-2-ylamino)ethyl]-phenyl}-1,4-dihydro-1,8-naphthyridine-3-carboxamide (compound 13)

2-amino-1-ethyl-7-{4-[2-({[(2R)-1-ethylpyrrolidin-2-yl]methyl}amino)-2-oxoethyl]phenyl}-N-methyl-4-oxo-1,4-dihydro-1,8-naphthyridine-3-carboxamide (compound 14)

2-amino-1-ethyl-7-{4-[2-({[(2S)-1-ethylpyrrolidin-2-yl]methyl}amino)-2-oxoethyl]phenyl}-N-methyl-4-oxo-1,4-dihydro-1,8-naphthyridine-3-carboxamide (compound 15)

2-amino-1-ethyl-N-methyl-4-oxo-7-{4-[2-oxo-2-(pyrimidin-4-ylamino)-ethyl]phenyl}-1,4-dihydro-1,8-naphthyridine-3-carboxamide (compound 16)

2-amino-1-ethyl-N-methyl-4-oxo-7-{4-[2-oxo-2-(pyrid-4-ylamino)ethyl]-phenyl}-1,4-dihydro-1,8-naphthyridine-3-carboxamide (compound 17)

2-amino-1-ethyl-N-methyl-7-(4-{2-[(2-morpholin-4-yl-ethyl)amino]-2-oxoethyl}phenyl)-4-oxo-1,4-dihydro-1,8-naphthyridine-3-carboxamide (compound 18)

2-amino-1-ethyl-N-methyl-4-oxo-7-{5-[2-oxo-2-(pyrid-2-ylamino)-ethyl]pyrid-2-yl}-1,4-dihydro-1,8-naphthyridine-3-carboxamide (compound 19)

2-amino-1-ethyl-N-methyl-7-{4-[1-methyl-2-oxo-2-(pyrid-2-ylamino)ethyl]-phenyl}-4-oxo-1,4-dihydro-1,8-naphthyridine-3-carboxamide (compound 20)

2-amino-1-ethyl-N-methyl-4-oxo-7-{6-[2-oxo-2-(pyrid-2-ylamino)-ethyl]pyrid-3-yl}-1,4-dihydro-1,8-naphthyridine-3-carboxamide (compound 21)

2-amino-1-ethyl-7-[4-(2-{[(4-ethylmorpholin-3-yl)methyl]amino}-2-oxoethyl)phenyl]-N-methyl-4-oxo-1,4-dihydro-1,8-naphthyridine-3-carboxamide (compound 22)

2-amino-1-ethyl-7-[6-(2-{[(4-ethylmorpholin-3-yl)methyl]amino}-2-oxoethyl)pyrid-3-yl]-N-methyl-4-oxo-1,4-dihydro-1,8-naphthyridine-3-carboxamide (compound 23)

2-amino-1-ethyl-7-{4-[2-({[(2S)-1-ethyl-4,4-difluoropyrrolidin-2-yl]methyl}-amino)-2-oxoethyl]phenyl}-N-methyl-4-oxo-1,4-dihydro-1,8-naphthyridine-3-carboxamide (compound 24)

2-amino-1-ethyl-7-[4-(2-{[(4-ethylmorpholin-3-yl)methyl]amino}-1-methyl-2-oxoethyl)phenyl]-N-methyl-4-oxo-1,4-dihydro-1,8-naphthyridine-3-carboxamide (compound 25)

2-amino-1-ethyl-7-{4-[2-({[(2S,4R)-1-ethyl-4-fluoropyrrolidin-2-yl]methyl}-amino)-2-oxoethyl]phenyl}-N-methyl-4-oxo-1,4-dihydro-1,8-naphthyridine-3-carboxamide (compound 26)

2-amino-1-ethyl-7-{4-[2-({[(2R)-1-(2-fluoroethyl)pyrrolidin-2-yl]methyl}-amino)-2-oxoethyl]phenyl}-N-methyl-4-oxo-1,4-dihydro-1,8-naphthyridine-3-carboxamide (compound 27)

2-amino-1-ethyl-N-methyl-7-{4-[2-({[(2R)-1-(methylsulfonyl)pyrrolidin-2-yl]methyl}amino)-2-oxoethyl]phenyl}-4-oxo-1,4-dihydro-1,8-naphthyridine-3-carboxamide (compound 28)

2-amino-1-ethyl-7-{5-[2-({[(2R)-1-(2-fluoroethyl)pyrrolidin-2-yl]methyl}-amino)-2-oxoethyl]pyrid-2-yl}-N-methyl-4-oxo-1,4-dihydro-1,8-naphthyridine-3-carboxamide (compound 29)

2-amino-1-ethyl-N-methyl-4-oxo-7-{4-[2-oxo-2-({[(2R)-1-(2,2,2-trifluoroethyl)pyrrolidin-2-yl]methyl}amino)ethyl]phenyl}-1,4-dihydro-1,8-naphthyridine-3-carboxamide (compound 30)

2-amino-7-{4-[2-({[(2R)-1-(2,2-difluoroethyl)pyrrolidin-2-yl]methyl}amino)-2-oxoethyl]phenyl}-1-ethyl-N-methyl-4-oxo-1,4-dihydro-1,8-naphthyridine-3-carboxamide (compound 31)

2-amino-1-ethyl-N-methyl-7-{4-[2-({[4-(1-methylethyl)morpholin-3-yl]-methyl}amino)-2-oxoethyl]phenyl}-4-oxo-1,4-dihydro-1,8-naphthyridine-3-carboxamide (compound 32)

2-amino-7-[4-(2-{[(4-cyclopropylmorpholin-3-yl)methyl]amino}-2-oxoethyl)phenyl]-1-ethyl-N-methyl-4-oxo-1,4-dihydro-1,8-naphthyridine-3-carboxamide (compound 33)

2-amino-7-{5-[2-({[(2R)-1-(2,2-difluoroethyl)pyrrolidin-2-yl]methyl}amino)-2-oxoethyl]pyrid-2-yl}-1-ethyl-N-methyl-4-oxo-1,4-dihydro-1,8-naphthyridine-3-carboxamide (compound 34)

2-amino-1-ethyl-N-methyl-4-oxo-7-{4-[2-oxo-2-(1,3-thiazol-2-ylamino)-ethyl]phenyl}-1,4-dihydro-1,8-naphthyridine-3-carboxamide (compound 35)

2-amino-1-ethyl-N-methyl-7-[4-(2-{[(1-methyl-1H-imidazol-5-yl)methyl]amino}-2-oxoethyl)phenyl]-4-oxo-1,4-dihydro-1,8-naphthyridine-3-carboxamide (compound 36)

2-amino-1-ethyl-N-methyl-4-oxo-7-(4-{2-oxo-2-[(2-pyrid-3-ylethyl)amino]-ethyl}phenyl)-1,4-dihydro-1,8-naphthyridine-3-carboxamide (compound 37)

2-amino-1-ethyl-N-methyl-7-(4-{2-[(3-morpholin-4-ylpropyl)amino]-2-oxoethyl}phenyl)-4-oxo-1,4-dihydro-1,8-naphthyridine-3-carboxamide (compound 38)

2-amino-1-ethyl-N-methyl-4-oxo-7-(4-{2-oxo-2-[(2-pyrid-2-ylethyl)amino]-ethyl}phenyl)-1,4-dihydro-1,8-naphthyridine-3-carboxamide (compound 39)

2-amino-1-ethyl-N-methyl-4-oxo-7-(4-{2-oxo-2-[(2-phenylethyl)amino]-ethyl}phenyl)-1,4-dihydro-1,8-naphthyridine-3-carboxamide (compound 40)

2-amino-1-ethyl-N-methyl-4-oxo-7-(4-{2-oxo-2-[(3-phenylpropyl)amino]-ethyl}phenyl)-1,4-dihydro-1,8-naphthyridine-3-carboxamide (compound 41)

2-amino-1-ethyl-N-methyl-7-[4-(2-{[2-(1-methyl-1H-pyrrol-2-yl)-ethyl]amino}-2-oxoethyl)phenyl]-4-oxo-1,4-dihydro-1,8-naphthyridine-3-carboxamide (compound 42)

2-amino-1-ethyl-7-[4-(2-{[(1-ethylpyrrolidin-2-yl)methyl]amino}-2-oxoethyl)-1,3-thiazol-2-yl]-N-methyl-4-oxo-1,4-dihydro-1,8-naphthyridine-3-carboxamide (compound 43)

2-amino-1-(3-methoxypropyl)-N-methyl-oxo-7-{4-[2-oxo-2-(pyrid-2-ylamino)ethyl]phenyl}-1,4-dihydro-1,8-naphthyridine-3-carboxamide (compound 44)

2-amino-7-[4-(2-{[1-(2,2-difluoroethyl)pyrrolidin-3-yl]amino}-2-oxoethyl)-phenyl]-1-ethyl-N-methyl-4-oxo-1,4-dihydro-1,8-naphthyridine-3-carboxamide (compound 45)

2-amino-1-ethyl-7-[4-(3-{[(1-ethylpyrrolidin-2-yl)methyl]amino}-3-oxopropyl)phenyl]-N-methyl-4-oxo-1,4-dihydro-1,8-naphthyridine-3-carboxamide (compound 46)

2-amino-1-ethyl-7-[4-(4-{[(1-ethylpyrrolidin-2-yl)methyl]amino}-4-oxobutyl)phenyl]-N-methyl-4-oxo-1,4-dihydro-1,8-naphthyridine-3-carboxamide (compound 47)

2-amino-1-ethyl-7-[4-(2-{[(1-ethylpyrrolidin-2-yl)methyl]amino}-2-oxoethyl)phenyl]-4-oxo-N-propyl-1,4-dihydro-1,8-naphthyridine-3-carboxamide (compound 48)

2-amino-7-[4-(2-{[(1-ethylpyrrolidin-2-yl)methyl]amino}-2-oxoethyl)-phenyl]-N-methyl-4-oxo-1-(2,2,2-trifluoroethyl)-1,4-dihydro-1,8-naphthyridine-3-carboxamide (compound 49)

2-amino-1-cyclopentyl-7-[4-(2-{[(1-ethylpyrrolidin-2-yl)methyl]amino}-2-oxoethyl)phenyl]-N-methyl-4-oxo-1,4-dihydro-1,8-naphthyridine-3-carboxamide (compound 50)

2-amino-1-ethyl-7-[4-(5-{[(1-ethylpyrrolidin-2-yl)methyl]amino}-5-oxopentyl)phenyl]-N-methyl-4-oxo-1,4-dihydro-1,8-naphthyridine-3-carboxamide (compound 51)

1-ethyl-7-[5-(2-{[(1-ethylpyrrolidin-2-yl)methyl]amino}-2-oxoethyl)thiophen-2-yl]-N,2-dimethyl-4-oxo-1,4-dihydro-1,8-naphthyridine-3-carboxamide (compound 52)

2-amino-7-{4-[2-({[(2R)-1-ethylpyrrolidin-2-yl]methyl}amino)-2-oxoethyl]-phenyl}-N-methyl-1-(2-methylpropyl)-4-oxo-1,4-dihydro-1,8-naphthyridine-3-carboxamide (compound 53)

2-amino-1-ethyl-7-{4-[1-({[(2R)-1-ethyl pyrrolidin-2-yl]methyl}carbamoyl)-cyclopropyl]phenyl}-N-methyl-4-oxo-1,4-dihydro-1,8-naphthyridine-3-carboxamide (compound 54)

2-amino-1-ethyl-7-{2-[2-({[(2R)-1-ethyl pyrrolidin-2-yl]methyl}amino)-2-oxoethyl]-1,3-thiazol-4-yl}-N-methyl-4-oxo-1,4-dihydro-1,8-naphthyridine-3-carboxamide (compound 55)

2-amino-1-ethyl-7-{4-[2-({[(2R)-1-ethyl pyrrolidin-2-yl]methyl}amino)-2-oxoethyl]-2-fluorophenyl}-N-methyl-4-oxo-1,4-dihydro-1,8-naphthyridine-3-carboxamide (compound 56)

2-amino-7-[3-chloro-4-(2-{[(1-ethylpyrrolidin-2-yl)methyl]amino}-2-oxoethyl)phenyl]-1-ethyl-N-methyl-4-oxo-1,4-dihydro-1,8-naphthyridine-3-carboxamide (compound 57)

2-amino-7-[3-fluoro-4-(2-{[(1-ethylpyrrolidin-2-yl)methyl]amino}-2-oxoethyl)phenyl]-1-ethyl-N-methyl-4-oxo-1,4-dihydro-1,8-naphthyridine-3-carboxamide (compound 58)

2-amino-7-[3-methyl-4-(2-{[(1-ethylpyrrolidin-2-yl)methyl]amino}-2-oxoethyl)phenyl]-1-ethyl-N-methyl-4-oxo-1,4-dihydro-1,8-naphthyridine-3-carboxamide (compound 59)

2-amino-1-(cyclopropylmethyl)-7-[4-(2-{[(1-ethylpyrrolidin-2-yl)methyl]amino}-2-oxoethyl)phenyl]-N-methyl-4-oxo-1,4-dihydro-1,8-naphthyridine-3-carboxamide (compound 60)

2-amino-1-ethyl-7-[4-(2-{[(1-ethylpyrrolidin-2-yl)methyl]amino}-2-oxoethyl)-2-methylphenyl]-N-methyl-4-oxo-1,4-dihydro-1,8-naphthyridine-3-carboxamide (compound 61)

2-amino-1-ethyl-7-[3-(2-{[(1-ethylpyrrolidin-2-yl)methyl]amino}-2-oxoethyl)phenyl]-N-methyl-4-oxo-1,4-dihydro-1,8-naphthyridine-3-carboxamide (compound 62)

2-amino-1-ethyl-N-methyl-4-oxo-7-{3-[2-oxo-2-(pyrid-2-ylamino)ethyl]-phenyl}-1,4-dihydro-1,8-naphthyridine-3-carboxamide (compound 63)

2-amino-1-ethyl-N-methyl-4-oxo-7-{4-[2-(pyrid-2-ylamino)ethyl]phenyl}-1,4-dihydro-1,8-naphthyridine-3-carboxamide (compound 64).

It should be noted that the above compounds have been named according to the IUPAC nomenclature by means of the ACDLABS 10.0 ACD/name (Advanced Chemistry Development) software.

In the text hereinbelow, the term "protecting group" Pg means a group that can, firstly, protect a reactive function such as a hydroxyl or an amine during a synthesis, and, secondly, regenerate the intact reactive function at the end of the synthesis. Examples of leaving groups and protection and deprotection methods are given in "Protective Groups in Organic Synthesis", Greene et al., $2^{nd}$ Edition (John Wiley & Sons, Inc., New York), 1991.

In the text hereinbelow, the term "leaving group" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and references for their preparation are given in "Advances in Organic Chemistry", J. March, $3^{rd}$ Edition, Wiley Interscience, 1985, pp. 310-316.

In accordance with the invention, the compounds of general formula (I) may be prepared according to the process that follows.

Scheme 1

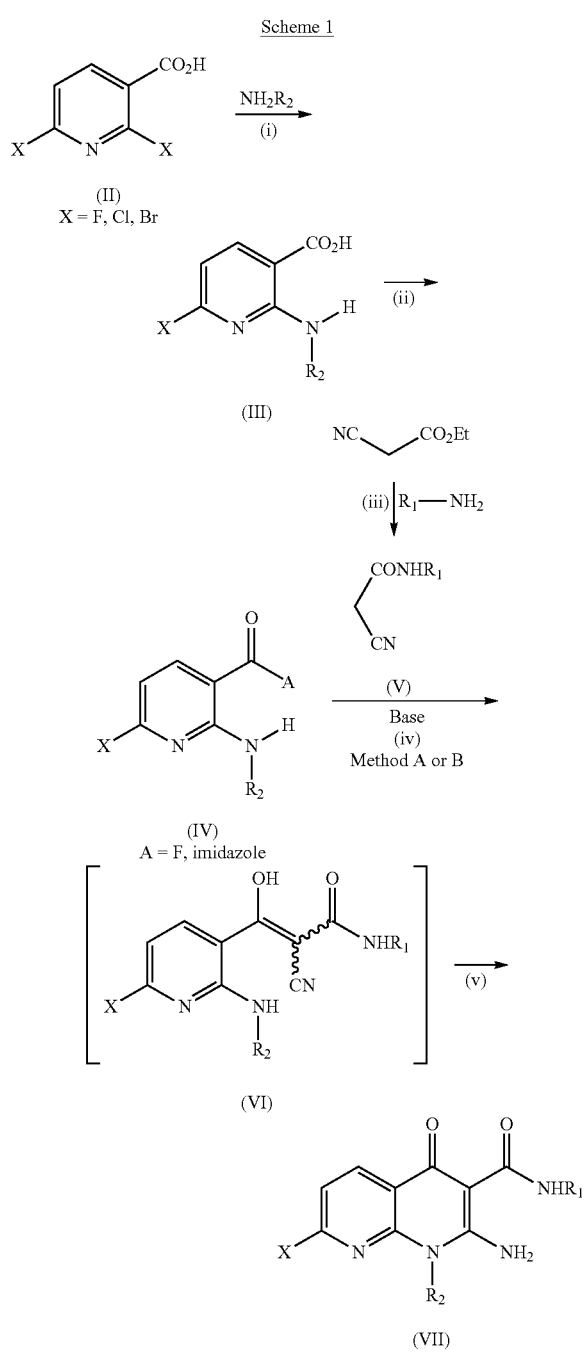

According to Scheme 1, a 2,6-dihalonicotinic acid of formula (II) is monosubstituted in position 2 with an amine of formula $R_2$—$NH_2$ (in which $R_2$ is as defined previously in relation to the compounds of formula (I)), at room temperature, or at a temperature from 50° C. to 100° C., heating conventionally or by microwave and in a protic solvent such as an alcohol, for example ethanol, n-butanol or tert-butanol, or water. The acid (III), obtained from step (i), is then activated as the derivative of formula (IV) either in the form of the acid fluoride via the action of cyanuric fluoride at room temperature, and in the presence of a base such as triethylamine or pyridine and in a solvent such as dichloromethane or THF, as described by G. Olah et al. in *Synthesis* (1973), 487, or in the form of the imidazolide via the action of carbonyldiimidazole in a solvent such as DMF or THF, or via other methods known to those skilled in the art, such as those described by Mukaiyama and Tanaka in *Chem. Lett.* (1976), 303 or by Ishikawa and Sasaki in *Chem. Lett.* (1976), 1407.

The acid fluoride or the imidazolide of formula (IV) obtained after step (ii), which are highly reactive but stable, are then reacted with an N-substituted cyanoacetamide of formula (V) according to method A or B.

According to method A, two equivalents of a base such as sodium hydride or potassium tert-butoxide are used for step (iv) of condensation of the N-substituted cyanoacetamide derivative with a compound of formula (IV). After reacting overnight at room temperature, a β-keto-cyanoacetamide of formula (VI) is obtained, which is then cyclized to the pyridopyridone of formula (VII) by heating to a temperature of between 90 and 125° C. in a polar solvent such as n-butanol, DMSO or DMF.

Method B is similar to method A for the condensation step (iv), but a third equivalent of the base used is added to the reaction mixture and the compound of formula (VI) formed cyclizes in situ, at room temperature, to form the pyridopyridone compound of formula (VII) directly.

The N-alkylcyanoacetamides of formula (V) are prepared according to step (iii) by reacting ethyl cyanoacetate with an excess of amine of formula $R_1$—$NH_2$ (in which $R_1$ is as defined previously in relation to the compounds of formula (I) that are subjects of the invention) in a solvent such as THF or ethanol, at a temperature ranging from room temperature to the reflux temperature of the solvent.

Scheme 2

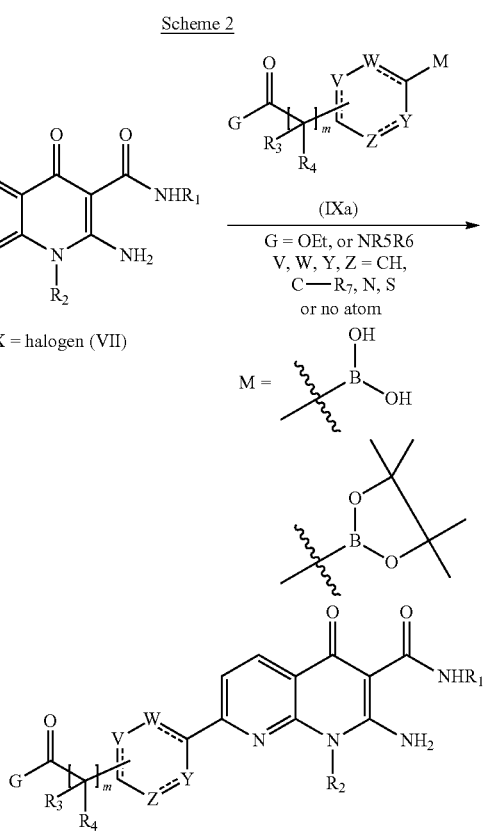

Route 1 if G = NR5R6, compound (I)
Route 2 if G = OEt, compound (X)

-continued

Route 2
if G = OEt,
compound (X) (vii)

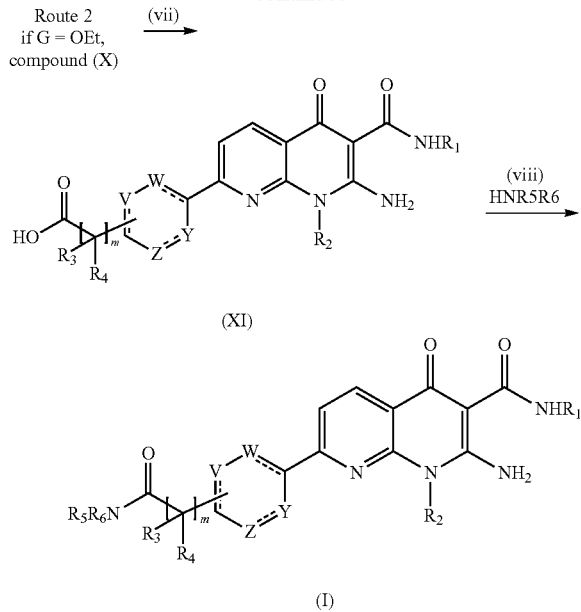

To obtain compounds of formula (I) that are subjects of the present invention, two methods may be used starting with the halo intermediate of formula (VII). According to method 1 described in Scheme 2, the intermediate (VII) is employed in step (vi) in a Suzuki coupling reaction with a boronic acid or a boronic ester of bispinacol (IXa) and m, $R_3$, $R_4$, V, W, Y and Z are as defined previously in relation to the compounds of formula (I) that are subjects of the invention, it being understood that the ring must be 5- or 6-membered, and G is either a (C1-C4)alkoxy group such as OEt or a unit —$NR_5R_6$, in which $R_5$ and $R_6$ are as defined for the compound of formula (I). This reaction (vi) is performed in the presence of a palladium complex (in oxidation state (0) or (II)), for instance $Pd(PPh_3)_4$, $PdCl_2(PPh_3)_2$, $Pd_2dba_3$, Xphos or $PdCl_2(dppf)$, in a polar, protic or aprotic solvent such as DME, ethanol, DMF or dioxane, or mixtures of these solvents, in the presence of a base such as caesium carbonate, aqueous sodium hydrogen carbonate or $K_3PO_4$, by conventional heating between 80 and 120° C. or under the action of microwaves between 130 and 170° C.

When G is a unit $NR_5R_6$, in which $R_5$ and $R_6$ are as defined for the compounds of formula (I), i.e. route 1, the compound of formula (I) that is a subject of the invention is obtained directly from this coupling (vi).

When G is a (C1-C4)alkoxy group such as OEt according to route 2, it is compound (X) that is obtained via the Suzuki coupling in step (vi). Compound (X) is then saponified, in step (vii), in the presence of a nucleophilic reagent such as LiOH or NaOH in aqueous solution, in a solvent such as a polar solvent, such as THF, DMF, MeOH or EtOH, at a temperature ranging from room temperature to 80° C., to give compound (XI), which is then used in a peptide coupling reaction, in step (viii), with the chosen amine $HNR_5R_6$, in which $R_5$ and $R_6$ are as defined for the compound of formula (I), in the presence of a coupling agent such as TBTU, HBTU or CU and of a base, for example diisopropylethylamine, triethylamine or $NaHCO_3$, in an aprotic solvent such as dichloromethane, THF or DMF, or via other methods known to those skilled in the art, such as those described by "Principles of Peptide Synthesis", $2^{nd}$ Ed. 1993, M. Bodanszky, Springer Laboratory, to give the compound of formula (I) that is a subject of the invention.

Scheme 3:

Method 2:

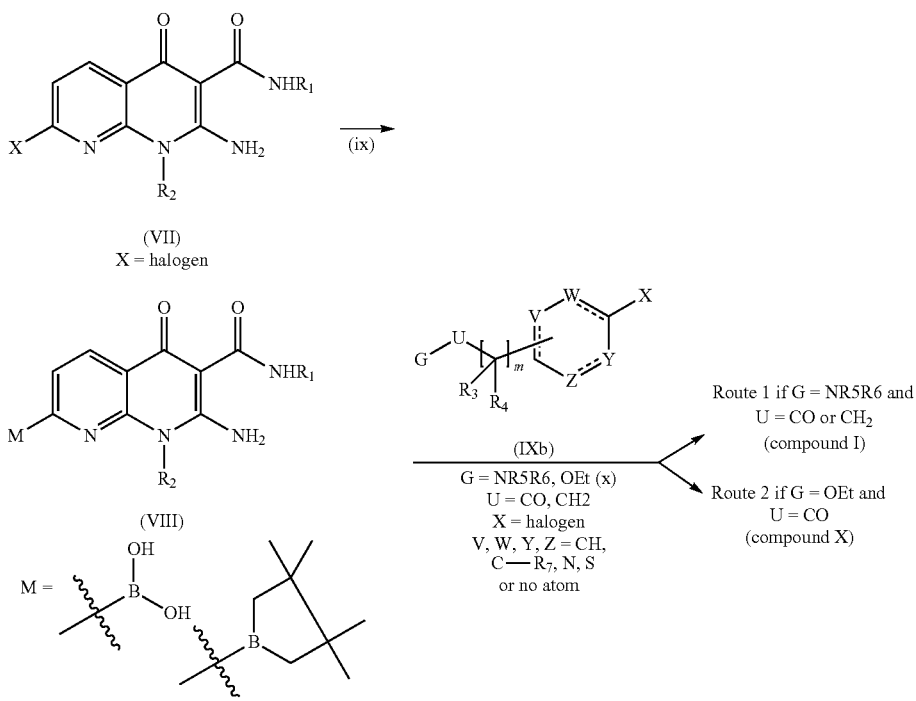

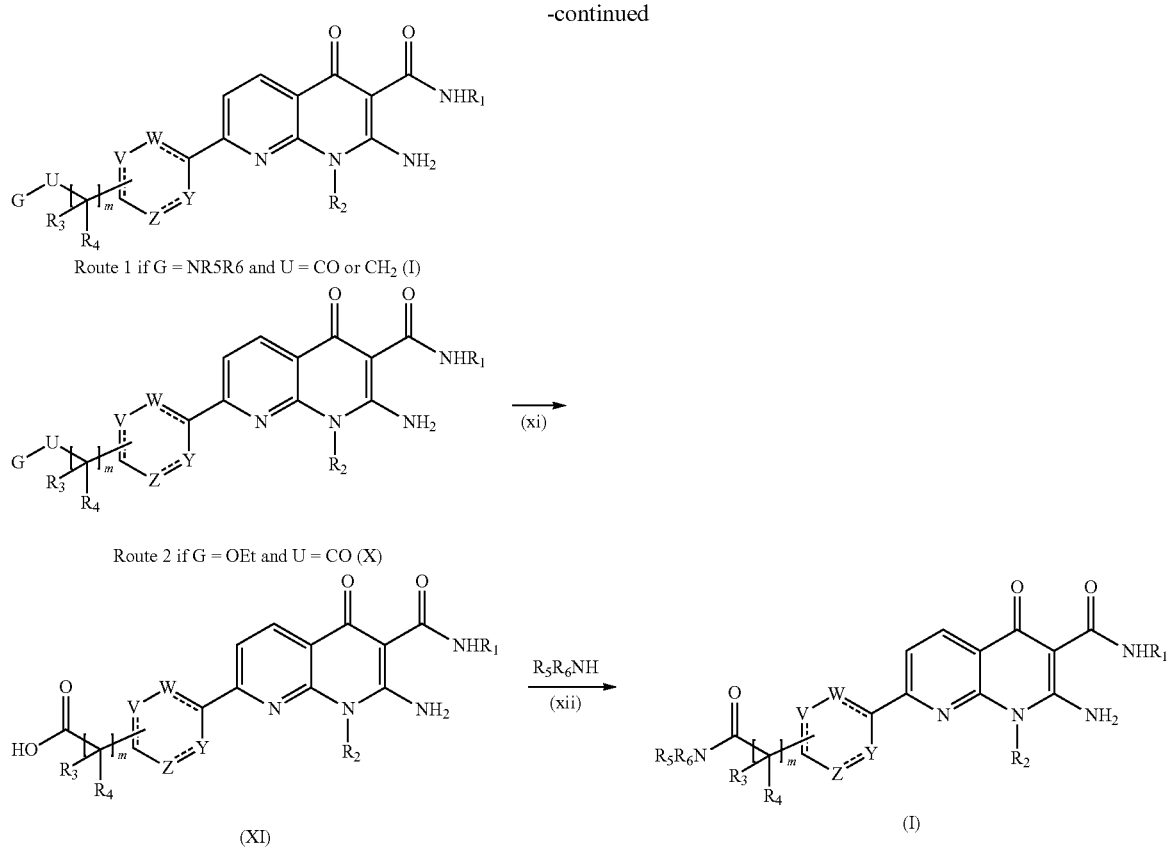

To obtain compounds of formula (I) that are subjects of the present invention, a second method may be used starting with the halo intermediate of formula (VII), this method 2 being described in Scheme 3. The halo intermediate of formula (VII) may be converted into the boronic acid or boronic ester derivative of bispinacol of formula (VIII) according to step (ix), by reaction with bis(pinacolato)diborane in the presence of [1,1'-bis(diphenylphosphino)ferrocene]dichloropalladium (II) and potassium acetate or potassium carbonate in a polar solvent such as DMSO, DMF, DME or dioxane, at a temperature between 50 and 100° C., according to the methodology described by Ishiyama, T. et al. in *J. Org. Chem.*, 1995, 60, 7508-7510 and Giroux, A. et al. in *Tet. Lett.*, 1997, 38, 3841-3844. In the following step (x), the acid or boronic ester compound (VIII) is used in a reaction of Suzuki type, with a halogenated aromatic compound of formula (IXb) in which X, m, $R_3$, $R_4$, U, V, W, Y and Z are as defined previously in relation with the compounds of formula (I) that are subjects of the invention, it being understood that the ring must be 5- or 6-membered and G is either a (C1-C4)alkoxy group such as OEt or a unit —$NR_5R_6$, in which $R_5$ and $R_6$ are as defined for the compound of formula (I). For this reaction (x), the Suzuki coupling conditions described in step (vi) of Scheme 2 may be applied.

When G is a unit $NR_5R_6$, in which $R_5$ and $R_6$ are as defined previously and U is either a carbonyl or a methylene unit, the compound of formula (I) that is a subject of the invention is obtained directly after the coupling step (x) (route 1).

When G is an OEt group and U is a carbonyl, it is route 2 that is followed, and it is compound (X) that is obtained via this Suzuki coupling (x). This compound (X) is then used in step (xi) to give the acid compound (XI), which is itself converted in step (xii) into a compound of formula (I) that is the subject of the invention. Steps (xi) and (xii) are identical, respectively, to steps (vii) and (viii) described previously.

When the methods for preparing the starting compounds, the reagents such as the amines $HNR_5R_6$ or the compounds of formula IXa and IXb used in Schemes 1, 2 and 3 are not described, they are either commercially available or may be prepared according to methods that are described in the literature or known to those skilled in the art.

If necessary, certain reactive functions located on the group $R_2$, $R_5$ or $R_6$ may be protected during these reactions, with protecting groups, as described in "Protective Groups in Organic Synthesis", Greene et al., $2^{nd}$ Edition (John Wiley & Sons, Inc., New York).

According to another of its aspects, a subject of the invention is also the compounds of formulae (VIII), (X) and (XI). These compounds are useful as intermediates for synthesizing the compounds of formula (I).

The examples that follow illustrate the preparation of certain compounds in accordance with the invention. These examples are not limiting, and serve merely to illustrate the present invention. The numbers of the compounds given as examples refer to those in the table below, which illustrates the chemical structures and the physical properties of a few compounds according to the invention.

The following abbreviations and empirical formulae are used:
EtOAc Ethyl acetate
CU Carbonyldiimidazole
DCM Dichloromethane
° C. degrees Celsius
DME Dimethoxyethane DMF Dimethylformamide
DMSO Dimethyl sulfoxide
EDC.HCl N-[3-(Dimethylamino)propyl-N'-ethylcarbodiimide hydrochloride
FAMSO Methyl methylthiomethyl sulfoxide
HBTU O-(Benzotriazol-1-yl)-N,N,N',N'-tetramethyluronium hexafluorophosphate
h Hour(s)
HCl Hydrochloric acid
LiOH Lithium hydroxide
$Na_2CO_3$ Sodium carbonate
$NH_4Cl$ Ammonium chloride
$NaHCO_3$ Sodium hydrogen carbonate
$Na_2SO_4$ Sodium sulfate
NaCl Sodium chloride
NaOH Sodium hydroxide
$NH_4OH$ Ammonium hydroxide
$Na_2SO_4$ Sodium sulfate
min. minutes
ml millilitres
$P_2O_5$ Diphosphorus pentoxide
TBTU N-[(1H-Benzotriazol-1-yloxy)(dimethylamino)methylidene]-N-methylmethanaminium tetrafluoroborate
THF Tetrahydrofuran
RT Room temperature
Xphos 2-Dicyclohexylphosphino-2',4',6'-triisopropylbiphenyl
Microwave apparatus used: Biotage, initiator
Analysis Conditions:
LC/UV/MS Coupling Conditions:
  Instrument (Agilent): HPLC chain: Series 1100, MSD SL mass spectrometer (Agilent), Software: Chemstation version B.01.03 from Agilent
LC/UV
  Column: Symmetry C18 3.5 μm (2.1×50 mm) (Waters), column temp.: 25° C.,
  Post run: 5 min. UV detection: 220 nm. Injection volume: 2 μl of a 0.5 mg/ml solution
Condition 1: pH 3 gradient 15 minutes
  Eluents: A: $H_2O$+0.005% TFA/B: $CH_3CN$+0.005% TFA, Flow rate: 0.4 ml/min. Gradient: 0 to 10 min 0 to 100% B, and from 10 to 15 min 100 B %
Condition 2: pH 3 gradient 30 minutes
  column: Symmetry C18 3.5 μm (2.1×50 mm) (Waters), Column temp.: 25° C., Eluents: A: $H_2O$+0.005% TFA/B: $CH_3CN$+0.005% TFA, Flow rate: 0.4 ml/min. Gradient: 0 to 30 min 0 to 100% B, and from 30 to 35 min 100 B %
  Post run: 6 min. UV detection: 220 nm. Injection volume: 2 μl of a 0.5 mg/ml solution
Condition 3: pH 7 gradient 20 minutes
  column: X terra MS C18 3.5 μm (2.1×50 mm), column temp.: 20° C.
  Eluents: A: $H_2O$+$NH_4Ac$ (5 nM)+3% $CH_3CN$/B: $CH_3CN$. Gradient 0 to 20 min 0 to 100% B. UV detection: 210 nm.
Condition GC Cl/CH4+): ionization Cl/CH4+, 30 minutes
  column: Agilent HP-5MS 30 m×250 μm, film 0.25 μm thick. Temperature 250° C., vector gas: helium, flow rate constant 1.4 ml/min
Mass Spectrometry (MS)
ionization mode: Electrospray positive mode ESI+, Mass range: 90-1500 amu
Spray Chamber Gas temp.: 350° C. Drying gas ($N_2$): 10.0 l/min Neb. pressure: 30 psig Vcap: 4000 V
The $^1H$ NMR spectra were obtained using Bruker 250, 300 or 400 MHz NMR spectrometers in DMSO-$d_6$, using the peak for DMSO-$d_5$ as reference. The chemical shifts δ are expressed in parts per million (ppm). The signals observed are expressed as follows: s=singlet; d=doublet; t=triplet; m=unresolved peak or broad singlet; H=proton.

The melting points below 260° C. were measured with a Köfler block and the melting points above 260° C. were measured with a Büchi B-545 machine.

The optical rotations were measured on a polarimeter of the type: Polarimeter Perkin-Elmer, energy 55 μA.

EXAMPLE 1

2-Amino-1-ethyl-7-{4-[2-({[(2R)-1-(2-fluoroethyl)-pyrrolidin-2-yl]methyl}amino)-2-oxoethyl]phenyl}-N-methyl-4-oxo-1,4-dihydro-1,8-naphthyridine-3-carboxamide hydrochloride (compound 27)

1.1: 6-Chloro-2-(ethylamino)pyridine-3-carboxylic acid

A solution of 18.0 g (84.4 mmol) of 2,6-dichloronicotinic acid in 180 ml (3.45 mol) of a 70% solution of ethylamine in water is heated at 50° C. for ten hours. The excess amine is then evaporated off under reduced pressure, and aqueous 10% acetic acid solution is then added until the product precipitates. The beige-coloured solid is filtered off by suction, rinsed with cold water and oven-dried. 10.5 g of the expected product are obtained. Yield=62%. Melting point: 158-160° C. $MH^+$: 201.1 (tr: 7.7 min., condition 1).

1.2: 6-Chloro-2-(ethylamino)pyridine-3-carbonyl fluoride

To a suspension of 10.5 g (52.3 mmol) of the compound obtained in step 1.1 in dichloromethane (250 ml) are successively added 4.2 ml (52.3 mmol) of pyridine and 8.4 ml (99.6 mmol) of cyanuric fluoride. The mixture is stirred for 3 hours at room temperature and then filtered. The solid is rinsed with dichloromethane (100 ml) and the filtrate is washed twice with ice-cold water (60 ml). The organic phase is dried over $Na_2SO_4$ and then concentrated under reduced pressure. 10.44 g of product are obtained, the form of an orange-coloured oil. Yield=99%. The product is used without purification in the following step.

1.3: 2-Cyano-N-methylacetamide

To 10.9 g (353.6 mmol) of a solution of methylamine in THF, cooled to 0° C., are added dropwise 20 g (176.8 mmol) of ethyl cyanoacetate, and the reaction mixture is then stirred at room temperature overnight. The solvents are evaporated off under reduced pressure and the product is purified by recrystallization from toluene. 16.8 g of product are obtained in the form of a beige-coloured solid. Yield=96%. Melting point=99° C.

Method A (1.4 and 1.5 Below)

1.4: 3-[6-Chloro-2-(ethylamino)pyrid-3-yl]-2-cyano-3-hydroxy-N-methylprop-2-enamide To a solution, cooled to 0-5° C., of 9.80 g (100 mmol) of the compound obtained from step 1.3 in 100 ml of anhydrous DMF are added portionwise 3.98 g (100 mmol) of sodium hydride at 60% in mineral oil. After the evolution of hydrogen has ceased, the mixture is stirred for ten minutes at room temperature, and then cooled again to 0-5° C. A solution of 10.1 g (49.8 mmol) of the compound obtained from step 1.2 in 60 ml of DMF is added and the mixture is stirred at room temperature overnight, and then 2.85 ml (49.8 mmol) of acetic acid are added. The DMF is evaporated off under reduced pressure, the residue is then taken up in water and the product is then extracted twice with a 95/5 dichloromethane/methanol mixture, and then once with an ethyl acetate/THF mixture (2/1). The combined organic phases are dried over $MgSO_4$ and the solvents are then evaporated off under reduced pressure. 19.0 g of product are obtained, which product is used in its native form in the following step.

1.5: 2-Amino-7-chloro-1-ethyl-N-methyl-4-oxo-1,4-dihydro-1,8-naphthyridine-3-carboxamide A solution of 19.0 g (49.8 mmol) of the crude product obtained from step 1.4 in 600 ml of n-butanol is heated for 48 hours at 110° C. The solvent is evaporated off under reduced pressure and the solid obtained is triturated in methanol. The solid is then filtered off and oven-dried. 7.9 g of the expected product are obtained in the form of a pale yellow solid. Yield=57%. Melting point: 283-286° C. $MH^+$: 281.2 (tr=6.99 min., condition 1).

Method B (1.6 Below Instead of 1.4 and 1.5)

1.6: 2-Amino-7-chloro-1-ethyl-N-methyl-4-oxo-1,4-dihydro-1,8-naphthyridine-3-carboxamide To a solution, cooled to 0-5° C., of 0.48 g (4.9 mmol) of the compound obtained from step 1.3 in anhydrous DMF (7 ml) is added portionwise 0.4 g (9.95 mmol) of sodium hydride at 60% in mineral oil. The mixture is stirred at this temperature for ten minutes, and a solution of 1.0 g (4.93 mmol) of the compound obtained from step 1.2 in anhydrous DMF (5 ml) is then added. The reaction mixture is stirred overnight at room temperature, and a further 0.2 g (4.9 mmol) of 60% sodium hydride are then added portionwise. Stirring is continued at this temperature for 30 minutes, 0.56 ml (9.8 mmol) of acetic acid is then added, followed by addition of 60 ml of water, and the solid is filtered off, rinsed with water and then oven-dried. 1.30 g of the expected product are obtained. Yield=94%. Melting point: 283-284° C. $MH^+$: 281.2 (tr=6.99 min., condition 1)

1.7 [7-Amino-8-ethyl-6-(methylcarbamoyl)-5-oxo-5,8-dihydro-1,8-naphthyridin-2-yl]boronic acid A suspension of 8 g (0.03 mol) of the compound obtained from step 1.5 or 1.6 (depending on whether method A or B was used), 8.0 g (0.03 mol) of bis(pinacolato)diborane and 8.5 g (0.08 mol) of potassium acetate in dimethyl sulfoxide (130 ml) is degassed with argon for 15 minutes. 1.4 g (1.7 mmol) of 1,1'-bis(diphenylphosphino)ferrocene]dichloropalladium(II) complexed with dichloromethane (1:1) is added and the mixture is heated at 80° C. for 30 minutes, under argon, and then cooled and diluted with 1.1 l of water and acidified to pH 4 by adding acetic acid (50 ml). The mixture is filtered and the black precipitate is washed with water (40 ml) and then with ether (60 ml). The black residue is taken up in 575 ml of NaOH solution (1N) and the mixture is filtered through Celite 545. The filtrate is acidified with 60 ml of acetic acid and the precipitate is filtered off, washed with water and ether and then oven-dried. 6.85 g of product are obtained in the form of a white powder. Yield=83%. Melting point: 335° C. $MH^+$: 291.2 (tr=5.3 min., condition 1)

$^1$H NMR (250 MHz, DMSO-$d_6$), δ (ppm): 11.69 (s, 1H); 11.12 (q, 1H, 4.67 Hz); 8.47 (s, 2H); 8.44 (d, 1H, 7.7 Hz); 7.9 (s, 1H); 7.75 (d, 1H, 7.7 Hz); 4.72 (m, 2H); 2.8 (d, 3H, 4.67 Hz); 1.22 (t, 3H, 6.9 Hz).

1.8: 1-Trityl-D-prolinamide

Under cold conditions (ice bath) and under an inert atmosphere, 10 ml of triethylamine (69.7 mmol) are added to 5 g (33.2 mmol) of prolinamide hydrochloride suspended in chloroform (50 ml), and 9.7 g (34.9 mmol) of trityl chloride are then added portionwise. The reaction mixture is stirred at room temperature for 2 days. The reaction mixture is dissolved in dichloromethane (200 ml) and washed successively twice with HCl solution (1N) (150 ml), with water (150 ml), with saturated $NaHCO_3$ solution (150 ml) and with saturated NaCl solution (150 ml). The organic phase is dried ($Na_2SO_4$), filtered and evaporated under reduced pressure. The residue is recrystallized from 20 ml of hot ethanol, to give 11 g of compound in the form of white crystals. Yield=93%. Melting point: 162° C.

1.9: 1-[(2R)-1-Tritylpyrrolidin-2-yl]methanamine

Under cold conditions (ice bath) and under an inert atmosphere, 60 ml (61.6 mmol) of a solution of lithium aluminium hydride (1N) in THF are added dropwise to 11 g (30.8 mmol) of the compound obtained from step 1.8 suspended in THF (60 ml). After addition, the reaction mixture is heated for 3 hours at 70° C. and then cooled to 0° C. 2.8 ml of water (formation of a precipitate), 2.8 ml of NaOH solution (1N) and 8.3 ml of water are then successively added dropwise. This mixture is stirred for 30 minutes and then filtered, the solid is rinsed with THF (10 ml) and the filtrate is then concentrated under reduced pressure. 10 g of compound are obtained in the form of a bright yellow powder, which is used without further purification in the following step. Yield=95%. Melting point: 100° C.

1.10: 2-(4-Iodophenyl)-N-[(2R)-pyrrolidin-2-ylmethyl]acetamide

Under an inert atmosphere and at room temperature, 4 ml (43.8 mmol) of oxalyl chloride are added to 3.8 g (14.6 mmol) of 4-iodophenylacetic acid suspended in dichloromethane (54 ml). Two drops of DMF are introduced and the reaction mixture is heated for one hour at room temperature, and then concentrated under reduced pressure. The residue is taken up in toluene and concentrated again. The acid chloride thus obtained is dissolved in dichloromethane (10 ml) and added dropwise to 5 g (14.6 mmol) of the compound obtained from step 1.9 suspended in dichloromethane (30 ml) in the presence of 2.45 g (29.2 mmol) of $NaHCO_3$, under cold conditions (ice bath) and under an inert atmosphere. The reaction medium is stirred overnight at room temperature, and is then filtered through Celite and concentrated under reduced pressure. 8.5 g of product are obtained in the form of a yellow foam, and are used directly in the following step without purification. $MH^+$: 586.

8.5 g (14.6 mmol) of this compound, obtained from the preceding step, are taken up in an ethanol/35% HCl mixture (41 ml/3.2 ml) under cold conditions (ice bath). The reaction medium is stirred for 2 hours at room temperature. The reaction medium is concentrated under reduced pressure, taken up in water (30 ml) and extracted with ether (30 ml×2). The aqueous phase, cooled, is basified with 35% NaOH solution added dropwise to pH 10. The product is then extracted with dichloromethane (100 ml×6). The organic phase is dried (Na₂SO₄), filtered and evaporated under reduced pressure. 4.6 g of compound are obtained, in the form of a white powder.

Yield=92% for the three steps. Melting point: 120° C. MH⁺: 345 (tr: 4.65 min., condition 1)

1.11: N-{[(2R)-1-(2-Fluoroethyl)pyrrolidin-2-yl]methyl}-2-(4-iodophenyl)-acetamide In a sealed tube, 0.53 g of NaHCO₃ (6.4 mmol) and 0.49 g of 1-iodo-2-fluoroethane (2.8 mmol) are added to 0.88 g (2.6 mmol) of the compound obtained from step 1.10 dissolved in DMF (6 ml). The sealed tube is heated at 90° C. for 5 hours. The reaction mixture is cooled, the DMF is then evaporated off under reduced pressure, and the residue obtained is taken up in water (10 ml) and extracted with ethyl acetate (20 ml×2). The organic phase is dried over sodium sulfate, filtered and evaporated under reduced pressure. The residue obtained is purified by flash chromatography on silica gel (eluent: dichloromethane/methanol, 1% NH₄OH), with a gradient of 0% to 10% methanol. 0.82 g of compound is obtained, in the form of a beige-coloured powder. Yield=85%. Melting point: 96° C. MH⁺: 391 (tr: 5.1 min., condition 1)

1.12: 2-Amino-1-ethyl-7-{4-[2-({[(2R)-1-(2-fluoroethyl)pyrrolidin-2-yl]-methyl}amino)-2-oxoethyl]phenyl}-N-methyl-4-oxo-1,4-dihydro-1,8-naphthyridine-3-carboxamide hydrochloride (compound 27)

In a sealing tube, 2.1 ml of saturated aqueous NaHCO₃ solution are added to 0.19 g (0.51 mmol) of the compound obtained from step 1.11 and 0.15 g (0.53 mmol) of the compound obtained from step 1.7 dissolved in a 2/1 mixture of 1,2-dimethoxyethane/ethanol (6 ml). After degassing with argon for 15 minutes, 0.03 g (0.03 mmol) of tetrakis(triphenylphosphine)palladium is added. The reaction medium is heated at 100° C. for 3 hours. The reaction medium is cooled to room temperature, water (10 ml) is then added and the precipitate formed is then filtered off, rinsed with water (5 ml×2) and then with dichloromethane (5 ml×2) and oven-dried. It is then purified by flash chromatography on silica gel (eluent: dichloromethane/methanol, 1% NH₄OH), with a gradient of 0% to 10% methanol. 0.05 g of product is obtained in the form of a white powder. The 0.05 g (0.1 mmol) of this compound thus obtained is suspended in 3 ml of methanol, and 0.1 ml (0.1 mmol) of a solution (1N) of HCl in ether is added. The reaction medium is stirred at room temperature for 30 minutes, 5 ml of ether are then added, and the precipitate formed is collected by filtration and oven-dried. 0.031 g of product is obtained in the form of a white powder. Yield=19%.

Melting point: 180° C. MH⁺: 509.3 (tr: 4.6 min., condition 1)

¹H NMR (400 MHz, DMSO-d₆), δ (ppm): 11.71 (broad s, 1H); 11.16 (d, 1H); 10.36 (broad s, 1H); 8.61 (m, 1H); 8.53 (d, 1H, 8.1 Hz); 8.16 (d, 2H, 8.3 Hz); 7.96 (s+d, 2H, 8.1 Hz); 7.47 (d, 2H, 8.3 Hz); 4.83 (broad m, 2H); 4.61 (m, 2H); 3.84-3.37 (very broad unresolved peak, 8H); 3.15 (m, 1H); 2.82 (d, 3H, 4.6 Hz); 2.15-1.68 (very broad m, 4H); 1.33 (t, 3H, 6.9 Hz).

EXAMPLE 2

2-Amino-1-ethyl-N-methyl-7-{4-[2-({[4-(1-methylethyl)-morpholin-3-yl]methyl}amino)-2-oxoethyl]phenyl}-4-oxo-1,4-dihydro-1,8-naphthyridine-3-carboxamide hydrochloride (compound 32)

2.1: 4-(1-Methylethyl)morpholine-3-carboxamide

To a solution of 1.1 g (6.3 mmol) of morpholine-3-carboxamide (a synthesis of which is described in WO-2005/026 156, Hennequin L. F. A. et al.) in acetonitrile (16 ml) are successively added 1.86 g (22.2 mmol) of sodium hydrogen carbonate powder and 0.7 ml (7.0 mmol) of isopropyl iodide, and the mixture is then heated at 150° C. by microwave for 30 minutes. The reaction mixture is cooled to room temperature, diluted with dichloromethane (30 ml) and filtered through Celite. The filtrate is concentrated under reduced pressure and 1.1 g of compound are obtained in the form of a beige-coloured powder, which is used without further purification in the following step. Yield: 97%. MH⁺: 173.2 (tr: 0.72 min., condition 1).

2.2: 1-[4-(1-Methylethyl)morpholin-3-yl]methanamine hydrochloride

Under an inert atmosphere, 15.4 ml of a solution (1M) of lithium aluminium hydride in THF are added dropwise to a solution of 1.1 g (6.15 mmol) of the compound obtained from step 2.1, in anhydrous THF, and the reaction mixture is then heated at 70° C. for 2 hours, and then cooled to room temperature. 0.6 ml of water, 0.6 ml of sodium hydroxide (1N) and 1.8 ml of water are successively added slowly, and the reaction mixture is then stirred for 30 minutes at room temperature. The precipitate formed is removed by filtration and rinsed with THF (20 ml). The filtrate is concentrated under reduced pressure, and 6.2 ml of a solution (1M) of HCl in diethyl ether are then added. The mixture is stirred at room temperature for 30 minutes and then concentrated under reduced pressure. 1.0 g of hydrochloride compound is obtained in the form of a brown powder, and is used without purification in the following step. Yield: 86%. MH⁺: 159.4 (tr: 0.53 min., condition 1).

2.3: Ethyl [4-(4,4,5,5-tetramethyl-1,3,2-dioxaborolan-2-yl)phenyl]acetate

A mixture of 9.5 g (32.8 mmol) of ethyl (4-iodophenyl) acetate and 9.16 g (36.1 mmol) of bispinacolatodiborane dissolved in anhydrous dimethyl sulfoxide (65 ml) is degassed with argon for 15 minutes, 27.8 g (98.4 mmol) of potassium acetate and 1.34 g (1.64 mmol) of dichloro(phosphinoferrocene)palladium are then added and the reaction mixture is heated at 55° C. for 1 hour 30 minutes under argon. The reaction mixture is diluted with 220 ml of ethyl acetate, and the organic phase is then washed three times with water (200 ml) and then dried over Na₂SO₄ and concentrated under reduced pressure. 10.8 g of compound are obtained in the form of an impure brown oil, but are used in this form in the following step. MH⁺: 291.2 (tr: 9.4 min., condition 1).

2.4: Ethyl {4-[7-amino-8-ethyl-6-(methylcarbamoyl)-5-oxo-5,8-dihydro-1,8-naphthyridin-2-yl]phenyl}acetate To 6.16 g (21.9 mmol) of the compound obtained from step 1.5 or 1.6 (depending on whether method A or B was used) and 7.64 g (26.3 mmol) of the compound obtained from step 2.3 dissolved in a 2/1 mixture of 1,2-dimethoxyethane/ethanol (275 ml) are added 88 ml of saturated aqueous NaHCO₃ solution. After degassing with argon for 15 minutes, 1.27 g (1.1 mmol) of tetrakis(triphenylphosphine)palladium are added. The reaction mixture is heated at 100° C. for 4 hours. The reaction medium is cooled to room temperature, water (300 ml) is then added and the precipitate formed is then filtered off, rinsed with water (20 ml×2), washed with ethyl acetate (50 ml) and then dried under vacuum over P₂O₅. 5.3 g of product are obtained in the form of a white powder. Yield: 59%. Melting point 195° C. MH+: 409.1 (tr: 5.89 min., condition 1).

2.5: {4-[7-Amino-8-ethyl-6-(methyl carbamoyl)-5-oxo-5,8-dihydro-1,8-naphthyridin-2-yl]phenyl}acetic acid To a suspension of 0.87 g (2.1 mmol) of the compound obtained from step 2.4 in a 1/1/1 mixture of THF/methanol/water (12 ml) is added 0.134 g (3.2 mmol) of lithium hydroxide in a single portion. The reaction mixture is heated at 70° C. for 3 hours, and then cooled to room temperature. Water (10 ml) is added and the medium is acidified with HCl solution (1N) to pH 2, and the precipitate formed is isolated by filtration and dried over $P_2O_5$. 0.78 g of product is obtained in the form of a white powder. Yield=96%. Melting point 260° C. MH+: 381.1 (tr: 6.74 min., condition 1).

2.6: 2-Amino-1-ethyl-N-methyl-7-{4-[2-({[4-(1-methylethyl)morpholin-3-yl]-methyl}amino)-2-oxo-ethyl]phenyl}-4-oxo-1,4-dihydro-1,8-naphthyridine-3-carboxamide hydrochloride (compound 32)

Under an inert atmosphere, 0.18 g of N,N-carbonyldiimidazole is added to a suspension of 0.4 g (1.1 mmol) of the compound obtained from step 2.5 in DMF (5 ml). The reaction mixture is stirred at room temperature for 1 hour 30 minutes, 0.225 g (1.2 mmol) of the compound obtained from step 2.2 dissolved in DMF (1 ml), and stirred beforehand in the presence of 0.13 g (1.3 mmol) of sodium carbonate, is then added and the mixture is heated at 80° C. for 2 hours. The DMF is removed by evaporation under reduced pressure, and the residue is then purified by flash chromatography on silica gel (eluent: dichloromethane/methanol/1% $NH_4OH$), with a gradient of 0% to 5% methanol. 0.3 g of product is obtained, in the form of a white powder. Yield: 57%. MH+: 521.3

To a suspension of 0.28 g (0.54 mmol) of this compound in methanol (2 ml) is added 0.05 ml of concentrated (35%) HCl solution. The mixture is stirred for 1 hour and diethyl ether (10 ml) is then added, and the solid formed is isolated by filtration and then dried under vacuum. 0.26 g of hydrochloride product is obtained in the form of an orange-coloured powder. Yield 87%. Melting point 192° C. MH+: 521.3 (tr: 9.1 min., condition 2)

$^1$H NMR (400 MHz, DMSO-$d_6$), δ (ppm): 11.75 (s, 1H); 11.13 (q, 1H, 4.6 Hz); 10.86 (s, 1H); 8.52 (d, 2H, 8.1 Hz); 8.16 (d, 2H, 8.3 Hz); 8.01 (s, 1H); 7.95 (d, 1H, 8.1 Hz); 7.46 (d, 2H, 8.3 Hz); 4.61 (q, 2H, 6.8 Hz); 3.96 (m, 3H); 3.83-3.02 (broad m, 9H); 2.8 (s, 3H); 1.24 (m, 9H).

EXAMPLE 3

2-Amino-1-ethyl-N-methyl-4-oxo-7-{5-[2-oxo-2-(pyrid-2-ylamino)ethyl]pyrid-2-yl}-1,4-dihydro-1,8-naphthyridine-3-carboxamide hydrochloride (compound 19)

3.1: 2-(6-Chloropyrid-3-yl)-N-pyrid-2-ylacetamide

Under an inert atmosphere, 6.23 g (38.5 mmol) of N,N-carbonyldiimidazole are added to a suspension of 6 g (35 mmol) of 2-chloropyridylacetic acid in anhydrous THF (90 ml) at room temperature. The reaction mixture is stirred at this temperature for 2 hours, 5.43 g (57.7 mmol) of 2-aminopyridine are then added and the mixture is refluxed for 2 hours. 200 ml of dichloromethane are added to the reaction mixture, cooled to room temperature, and the organic phase thus obtained is washed with saturated ammonium chloride solution and then with aqueous sodium hydroxide solution (1N), dried over $Na_2SO_4$, filtered and concentrated under reduced pressure. The residue is purified by flash chromatography on silica gel (eluent: dichloromethane/ethyl acetate, from 0% to 70% ethyl acetate). 5.6 g of compound are obtained in the form of a white powder. Yield 65%. Melting point: 130° C. MH+: 248.1 (tr: 5.45 min., condition 1).

3.2: 2-Amino-1-ethyl-N-methyl-4-oxo-7-{5-[2-oxo-2-(pyrid-2-ylamino)-ethyl]pyrid-2-yl}-1,4-dihydro-1,8-naphthyridine-3-carboxamide hydrochloride (compound 19)

Using the same procedure as that described in Example 1, step 1.12, starting with 0.32 g (1.3 mmol) of the compound obtained from step 3.1, 0.41 g (1.4 mmol) of the compound obtained from step 1.7, 74 mg (0.06 mmol) of tetrakis(triphenylphosphine)palladium, 14.5 ml of saturated sodium hydrogen carbonate solution in a mixture of 1,2-dimethoxyethane/ethanol (2/1) (19 ml) and 0.26 ml of a solution (1M) of HCl in ether, 0.095 g of hydrochloride product is obtained in the form of a yellow powder. MH+: 458.3 (tr: 6.3 min., condition 1). Yield: 16%. Melting point: 268-288° C. (decomposition).

$^1$H NMR (400 MHZ, DMSO-$d_6$), δ (ppm): 11.77 (s, 1H); 11.3 (s, 1H); 11.12 (s, 1H); 8.74 (d, 1H, 2 Hz); 8.62 (d, 1H, 8.1 Hz); 8.49 (d, 1H, 8.2 Hz); 8.36 (m, 1H); 8.35 (d, 1H, 8.1 Hz); 8.05 (s+dd, 2H, 2, 8.2 Hz); 8 (d, 1H, 8.4 Hz); 7.9 (dd, 1H, 7.2, 8.4 Hz); 7.2 (dd, 1H, 5.2, 7.2 Hz); 6.33 (2HCl); 4.64 (m, 2H); 3.97 (s, 2H); 2.82 (s, 3H); 1.33 (t, 3H, 6.8 Hz).

EXAMPLE 4

2-Amino-1-ethyl-N-methyl-4-oxo-7-{6-[2-oxo-2-(pyrid-2-ylamino)ethyl]pyrid-3-yl}-1,4-dihydro-1,8-naphthyridine-3-carboxamide (compound 21)

4.1: 2-(5-Bromopyrid-2-yl)-N-pyrid-2-ylacetamide

Under an inert atmosphere, 0.09 g (0.95 mmol) of 2-aminopyridine, 0.31 g (2.4 mmol) of diisopropylethylamine and 0.35 g (1.1 mmol) of TBTU are successively added to 0.26 g (0.95 mmol) of (5-bromo-2-pyridyl)acetic acid (a synthesis of which is described in Tetrahedron, 1997, 53(24) 8257-8268 Gurnos J. et al.) dissolved in anhydrous THF (4 ml). The reaction mixture is stirred for 3 hours at room temperature. The reaction mixture is concentrated under reduced pressure, the residue is taken up in ethyl acetate (20 ml) and the organic phase thus obtained is then washed with saturated ammonium chloride solution (15 ml) and with saturated sodium hydrogen carbonate solution (15 ml), and then dried over $Na_2SO_4$, filtered and concentrated under reduced pressure. The residue is purified by flash chromatography on silica gel (eluent: dichloromethane/ethyl acetate, 1% $NH_4OH$), with a gradient of 0% to 20% ethyl acetate, 1% $NH_4OH$. 0.125 g of compound is obtained in the form of a white powder. Yield: 45%. Melting point: 131° C. MH+: 292-294 (tr: 6.1 min., condition 1).

4.2: 2-Amino-1-ethyl-N-methyl-4-oxo-7-{6-[2-oxo-2-(pyrid-2-ylamino)-ethyl]pyrid-3-yl}-1,4-dihydro-1,8-naphthyridine-3-carboxamide (compound 21)

Using the same procedure as that described in Example 1, step 1.12, starting with 0.42 g (1.4 mmol) of the compound obtained from step 4.1, 0.46 g (1.6 mmol) of the compound obtained from step 1.7, 83 mg (0.07 mmol) of tetrakis(triphenylphosphine)palladium and 15 ml of saturated sodium hydrogen carbonate solution in a mixture of 1,2-dimethoxyethane/ethanol (2/1) (24 ml), 0.03 g of product is obtained in the form of a white powder. Yield: 5%. Melting point: 266° C. MH+ 458.1 (tr: 6.5 min., condition 1)

$^1$H NMR (400 MHz, DMSO-d$_6$), δ (ppm): 11.76 (s, 1H); 11.10 (q, 1H, 4.6 Hz); 10.78 (s, 1H); 9.32 (d, 1H, 2.3 Hz); 8.57 (d, 1H, 8.1 Hz); 8.53 (dd, 1H, 2.3-8.2 Hz); 8.34 (d, 1H, 5 Hz); 8.07 (d, 1H, 8.2 Hz); 8.04 (d+s, 2H, 8.2 Hz); 7.78 (dd, 1H, 7.4, 8.2 Hz); 7.59 (d, 1H, 8.1 Hz); 7.12 (dd, 1H, 5, 7.4 Hz); 4.61 (m, 2H); 4.05 (s, 2H); 2.82 (d, 3H, 4.6 Hz); 1.3 (t, 3H, 6.8 Hz).

EXAMPLE 5

2-Amino-7-[4-(2-{[(4-cyclopropylmorpholin-3-yl)methyl]amino}-2-oxoethyl)phenyl]-1-ethyl-N-methyl-4-oxo-1,4-dihydro-1,8-naphthyridine-3-carboxamide hydrochloride (compound 33)

5.1: 4-Cyclopropylmorpholine-3-carboxamide

To 1.2 g (7.2 mmol) of morpholine-3-carboxamide hydrochloride (a synthesis of which is described in WO-2005/026 156, Hennequin L. F. A. et al.) dissolved in methanol (36 ml) are successively added 2.9 g of 3 Å molecular sieves, 4.3 g (72 mmol) of acetic acid, 7. g (43.2 mmol) of 2-[(1-ethoxycyclopropyl)oxy]trimethylsilane and 4.4 g (31.7 mmol) of sodium cyanoborohydride. The reaction mixture is heated at 70° C. for 3 hours 30 minutes, and then cooled to room temperature and filtered. The filtrate is concentrated under reduced pressure and the residue is then taken up in dichloromethane (200 ml) and washed three times with aqueous NaOH solution (1N) (100 ml). The organic phase is dried over Na$_2$SO$_4$, filtered and then concentrated under reduced pressure. 0.58 g of product is obtained, in the form of a white powder. Yield 47%. Melting point 116° C. MH+: 171.2 (tr: 1.03 min., condition 1).

5.2: 1-(4-Cyclopropylmorpholin-3-yl)methanamine hydrochloride

Under an inert atmosphere, 13.6 ml (13.6 mmol) of a solution (1N) of triborohydride complexed with tetrahydrofuran, in THF, are added dropwise to a solution of 0.58 g (3.4 mmol) of the compound obtained from step 5.1 in anhydrous THF, cooled to 0° C. The reaction mixture is heated at 70° C. for 3 hours. 15 ml of HCl solution (1N) are added to the reaction mixture cooled to room temperature. After stirring for 30 minutes, the aqueous phase is separated out by settling and extracted twice with ether (15 ml) and then basified by addition of sodium hydroxide solution (1N). The aqueous phase is then extracted 4 times with ethyl acetate (20 ml) and 4 times with dichloromethane (20 ml). The combined organic phases are dried over Na$_2$SO$_4$, filtered and concentrated under reduced pressure. The residue is taken up in methanol (4 ml), and 3.4 ml of a solution of HCl in ether are added. The solution is stirred for 30 minutes, and 5 ml of ether are then added. The solid formed is collected by filtration and dried under vacuum over P$_2$O$_5$. 0.51 g of product is obtained, in the form of a white powder. Yield 78%. MH+: 157.2 (tr: 0.4 min., condition 1).

5.3: 2-Amino-7-[4-(2-{[(4-cyclopropylmorpholin-3-yl)methyl]amino}-2-oxoethyl)phenyl]-1-ethyl-N-methyl-4-oxo-1,4-dihydro-1,8-naphthyridine-3-carboxamide hydrochloride (compound 33)

Using the same procedure as that described in Example 2, step 2.6, starting with 0.33 g (0.88 mmol) of the compound obtained from step 2.5, suspended in anhydrous DMF (5 ml), 0.15 g (0.92 mmol) of CU is added and the mixture is stirred at room temperature for 2 hours 40 minutes. In parallel, under an inert atmosphere, 0.11 g (1.1 mmol) of sodium carbonate is added to 0.22 g (0.97 mmol) of the compound obtained from step 5.2, dissolved in DMF (2 ml), and the mixture is stirred at RT for 2 hours. The supernatant is then removed and is added dropwise to the imidazolide intermediate formed previously. The mixture is then heated at 80° C. for 2 hours. The DMF is evaporated off under reduced pressure, and the residue is purified by flash chromatography on silica gel (eluent: dichloromethane/methanol) with a gradient of 0% to 5% methanol. 0.13 g of product is obtained in the form of a white powder. Yield: 28%.

To 0.13 g (0.25 mmol) of this compound dissolved in 2 ml of methanol is added 0.02 g (0.3 mmol) of concentrated 35.6% HCl solution. The mixture is stirred at RT for 1 hour, and the solid formed is collected by filtration and dried over P$_2$O$_5$. 0.13 g of compound is obtained, in the form of a white powder. Yield 92%. Melting point: 250° C. MH+: 519.2 (tr: 5.5 min., condition 1).

$^1$H NMR (400 MHz, DMSO-d$_6$) 11.74 (s, 1H); 11.13 (q, 1H, 4.6 Hz); 10.33 (s, 1H); 8.53 (d, 1H, 8.1 Hz); 8.38 (s, 1H); 8.16 (d, 2H, 8.1 Hz); 8.0 (s, 1H); 7.97 (d, 1H, 8.1 Hz); 7.45 (d, 2H, 8.1 Hz); 4.61 (m, 2H); 4.03-3.79 (m, 3H); 3.69-3.24 (m, 8H); 2.95 (m, 1H); 2.81 (s, 3H); 1.32 (t, 3H, 6.9 Hz); 1.16-0.92 (m, 4H).

EXAMPLE 6

2-Amino-1-ethyl-7-{4-[2-({[(2S,4R)-1-ethyl-4-fluoropyrrolidin-2-yl]methyl}amino)-2-oxoethyl]phenyl}-N-methyl-4-oxo-1,4-dihydro-1,8-naphthyridine-3-carboxamide hydrochloride (compound 26)

6.1: (4R)-1-Ethyl-4-fluoro-L-prolinamide

Using the same procedure as that described in Example 2, step 2.1, starting with 0.88 g (5.2 mmol) of 4(R)-fluoro-2(S)-pyrrolinecarboxamide (a synthesis of which is described in Bioorg. Med. Chem. 12 (23), 2004, 6053-6061, Fukushima H. et al.), 0.90 g (5.7 mmol) of ethyl iodide and 1.53 g (18.3 mmol) of NaHCO$_3$ in anhydrous DMF (17 ml), 0.84 g of product is obtained, in the form of a white powder. Yield: 100%. Melting point: 127° C. MH+: 161.2 (tr: 0.36 min., condition 1).

6.2: 1-[(2S,4R)-1-Ethyl-4-fluoropyrrolidin-2-yl] methanamine hydrochloride

Using the same procedure as that described in Example 5, step 5.2, starting with 0.69 g (4.3 mmol) of the compound obtained from step 6.1, 17.3 ml (17.3 mmol) of a solution (1M in THF) of boron trihydride complexed with tetrahydrofuran, in anhydrous THF (30 ml), and then 4.3 ml of a solution (1M) of HCl in ether, 0.33 g of product is obtained in the form of a yellow oil, and is used without further purification in the following step. Yield: 52%. MH+: 147.3 (tr: 0.36 min., condition 1).

6.3: 2-Amino-1-ethyl-7-{4-[2-({[(2S,4R)-1-ethyl-4-fluoropyrrolidin-2-yl]-methyl}amino)-2-oxoethyl] phenyl}-N-methyl-4-oxo-1,4-dihydro-1,8-naphthyridine-3-carboxamide hydrochloride (compound 26)

Under an inert atmosphere, to a suspension of 0.85 g (2.2 mmol) of the compound obtained from step 2.5, in dichloromethane (9 ml), is added 0.45 g (4.4 mmol) of triethylamine. The mixture is cooled to 0° C. (ice bath) and 0.61 g (4.4 mmol) of cyanuric fluoride dissolved in dichloromethane (1 ml) is added dropwise. The mixture is stirred at RT for 3 hours 30 minutes, and then diluted with 30 ml of dichloromethane, washed with 20 ml of saturated NaHCO₃ solution, cooled beforehand, dried over Na₂SO₄, filtered and concentrated. The acid fluoride obtained is used without purification in the following step.

To 0.24 g (1.6 mmol) of compound obtained from step 6.2 dissolved in anhydrous DMF (4 ml) is added 0.41 g (4.1 mmol) of triethylamine, followed by addition of 0.63 g (1.7 mmol) of acid fluoride obtained from the preceding step. The mixture is stirred at RT overnight, the DMF is then evaporated off under vacuum, the residue is taken up in dichloromethane (20 ml) and the organic phase is washed with saturated NaHCO₃ solution, dried over Na₂SO₄, filtered and concentrated under reduced pressure. The residue is purified by flash chromatography on silica gel (eluent: dichloromethane/methanol) with a gradient of 0% to 3% methanol. 0.075 g of compound is obtained in the form of a white powder. Yield: 9%. $\alpha_D$=−12 (concentration: 25 mg/ml in MeOH). MH⁺: 509 (tr: 5.2 min., condition 1).

To 0.07 g (0.13 mmol) of the compound obtained from the preceding step dissolved in methanol (2.5 ml) is added 0.13 ml (0.13 mmol) of a solution (1M) of HCl in ether. The mixture is stirred at RT for 1 hour and then concentrated under reduced pressure. The solid is triturated in dichloromethane (2 ml), filtered off and dried under vacuum over P₂O₅. 0.05 g of compound is obtained in the form of a pale yellow powder. Yield: 59%. Melting point 170° C. MH⁺: 509.3 (tr: 5.2 min., condition 1).

¹H NMR (400 MHz, DMSO-d₆), δ (ppm): 11.73 (s, 1H); 11.12 (m, 1H); 10.56 (s, 1H); 8.59 (t, 1H, 5.6 Hz); 8.54 (d, 1H, 8.1 Hz); 8.16 (d, 2H, 8.3 Hz); 7.99 (s, 1H); 7.96 (d, 1H, 8.1 Hz); 7.48 (d, 2H, 8.3 Hz); 5.41 (dt, 1H, 4.9-53.2 Hz); 4.61 (m, 2H); 3.9 (m, 1H); 3.82-3.44 (m, 6H); 3.38 (m, 1H); 3.12 (m, 1H); 2.82 (m, 3H); 2.36 (m, 1H); 2.02 (m, 1H); 1.33 (t, 3H, 6.8 Hz); 1.24 (t, 3H, 7.9 Hz).

EXAMPLE 7

2-Amino-1-ethyl-7-{4-[2-({[(2S)-1-ethyl-4,4-difluoropyrrolidin-2-yl]methyl}amino)-2-oxoethyl]phenyl}-N-methyl-4-oxo-1,4-dihydro-1,8-naphthyridine-3-carboxamide hydrochloride (compound 24).

7.1: 1-Ethyl-4,4-difluoro-L-prolinamide

Using the same procedure as that described in Example 2, step 2.1, starting with 0.2 g (1.1 mmol) of 4,4-difluoro-2(S)-pyrrolinecarboxamide (a synthesis of which is described in Bioorg. Med. Chem. 12 (23) 2004 6053-6061 Fukushima H. et al.), 0.18 g (1.2 mmol) of ethyl iodide and 0.32 g (3.7 mmol) of NaHCO₃ in anhydrous DMF (3.5 ml), 0.18 g of product is obtained, in the form of a white powder. Yield: 95%. Melting point: 138° C. MH⁺: 179.2 (tr: 1.25 min., condition 1).

7.2: 1-[(2S)-1-Ethyl-4,4-difluoropyrrolidin-2-yl]methanamine hydro-chloride

Using the same procedure as described in Example 2, step 5.2, starting with 0.18 g (1 mmol) of compound obtained from step 7.1, 8.2 ml (8.2 mmol) of a solution (1M in THF) of boron trihydride complexed with tetrahydrofuran, in anhydrous THF (12 ml), and 2 ml of a solution (1M) of HCl in ether, 0.2 g of product is obtained in the form of a grey powder, and is used without further purification. Yield: 100%. MH⁺: not detectable 7.3: 2-Amino-1-ethyl-7-{4-[2-({[(2S)-1-ethyl-4,4-difluoropyrrolidin-2-yl]-methyl}amino)-2-oxoethyl]phenyl}-N-methyl-4-oxo-1,4-dihydro-1,8-naphthyridine-3-carboxamide hydrochloride (compound 24)

Under an inert atmosphere, 0.37 ml (3.8 mmol) of diisopropylethylamine and then a solution in DMF (2 ml) of 0.20 g (0.85 mmol) of the compound obtained from step 7.2 in the presence of 0.3 ml (1.7 mmol) of diisopropylethylamine are successively added to 0.32 g (0.85 mmol) of compound obtained from step 2.5, suspended in anhydrous DMF (4 ml). 0.31 g (0.9 mmol) of TBTU is added to this reaction mixture, cooled in an ice bath. The reaction mixture is stirred for 6 hours at 70° C. and then concentrated under reduced pressure. The residue is purified by flash chromatography on silica gel (eluent: dichloromethane/ethyl acetate, 1% NH₄OH), with a gradient of 0% to 100% ethyl acetate, 1% NH₄OH. 0.087 g of compound is obtained in the form of a pink powder.

To 0.087 g (0.17 mmol) of the compound obtained from the preceding step, dissolved in 2 ml of methanol, is added 0.17 ml (0.17 mmol) of an HCl solution (1M in ether). The mixture is stirred at RT for 1 hour, 5 ml of ether are then added and the solid formed is collected by filtration and dried over P₂O₅ under vacuum. 0.065 g of product is obtained in the form of a pink powder. Yield: 70%. Melting point: 266° C. MH⁺: 527.3 (tr: 6.04 min., condition 1).

¹H NMR (400 MHz, DMSO-d₆), δ (ppm): 11.74 (s, 1H); 11.12 (q, 1H, 4.6 Hz); 11.08 (s, 1H); 8.58 (s, 1H); 8.53 (d, 1H, 8.1 Hz); 8.16 (d, 2H, 8.3 Hz); 7.98 (s, 1H); 7.96 (d, 1H, 8.1 Hz); 7.47 (d, 2H, 8.3 Hz); 4.61 (m, 2H); 4.18 (q, 1H, 10.7 Hz); 3.91 (m, 1H); 3.82 (q, 1H, 12.9 Hz); 3.59 (s, 2H); 3.56 (m, 3H); 3.17 (m, 1H); 2.81 (s, 3H); 2.75 (m, 1H); 2.43 (m, 1H); 1.32 (t, 3H, 6.8 Hz); 1.21 (t, 3H, 7.1 Hz).

EXAMPLE 8

2-Amino-1-ethyl-7-[4-(2-{[(4-ethylmorpholin-3-yl)methyl]-amino}-2-oxoethyl)phenyl]-N-methyl-4-oxo-1,4-dihydro-1,8-naphthyridine-3-carboxamide hydrochloride (compound 22)

8.1: 4-Ethylmorpholine-3-carboxamide

Using the same procedure as that described in Example 2, step 2.1, starting with 0.2 g (1.1 mmol) of morpholine-3-carboxamide (the synthesis of which is described in WO-2005/026 156, Hennequin L. F. A. et al.), 0.18 g (1.2 mmol) of ethyl iodide and 0.32 g (3.7 mmol) of NaHCO₃ in anhydrous DMF (3.5 ml), 0.18 g of product is obtained in the form of a white powder. Yield: 95%. Melting point: 127° C. MH⁺: 159.3 (tr=0.35 min., condition 1).

8.2: 1-(4-Ethylmorpholin-3-yl)methanamine

Under an inert atmosphere, 0.76 ml (0.76 mmol) of a solution (1M) in THF of lithium aluminium hydride is added to 0.06 g (0.38 mmol) of the compound obtained from step 8.1, dissolved in anhydrous THF, and the reaction mixture is then heated at 70° C. for 5 hours. 28 μl of water, 28 μl of sodium hydroxide (1N) and 84 μl of water are successively added to the mixture, cooled to RT, to form a cake. The mixture is stirred vigorously for 30 minutes and the precipitate is then removed by filtration. The filtrate is concentrated under reduced pressure to give 0.06 g of product in the form of a colourless oil, which is used without purification in the following step.

Yield: 100%.

$^1$H NMR (300 MHz, DMSO-d$_6$), δ (ppm): 3.82 (m, 2H); 3.61 (m, 2H); 2.92 (m, 2H); 2.77 (m, 2H); 2.4 (m, 3H); 1.53 (s, 2H); 1.1 (t, 3H, 7.5 Hz).

8.3: 2-Amino-1-ethyl-7-[4-(2-{[(4-ethylmorpholin-3-yl)methyl]amino}-2-oxoethyl)phenyl]-N-methyl-4-oxo-1,4-dihydro-1,8-naphthyridine-3-carboxamide hydrochloride Using the same procedure as that described in Example 7, step 7.3, starting with 0.14 g (0.37 mmol) of the compound obtained from step 2.5, 0.05 g (0.37 mmol) of the compound obtained from step 8.2, 0.13 g (0.4 mmol) of TBTU and 0.12 g (0.92 mmol) of diisopropylethylamine in anhydrous DMF (4 ml) and 0.17 ml of a solution (1M) of HCl in ether, 0.07 g of product is obtained, in the form of a white powder. Yield: 50%. Melting point: 190° C. MH$^+$: 507.1 (tr: 5.4 min., condition 1).

$^1$H NMR (400 MHz, DMSO-d$_6$), δ (ppm): 11.73 (s, 1H); 11.12 (q, 1H, 4.6 Hz); 11.03+10.76 (2s, 1H); 8.52 (d, 2H, 8.1 Hz); 8.15 (d, 2H, 8.1 Hz); 7.98 (broad s, 1H); 7.95 (d, 1H, 8.1 Hz); 7.47 (d, 2H, 8.1 Hz); 4.61 (m, 2H); 3.94 (m, 2H); 3.81 (m, 1H); 3.58 (m, 3H); 3.38 (m, 4H); 3.18 (m, 3H); 2.81 (d, 3H, 4.6 Hz); 1.28 (m, 6H).

EXAMPLE 9

1-Ethyl-7-[5-(2-{[(1-ethylpyrrolidin-2-yl)methyl]amino}-2-oxoethyl)thiophen-2-yl]-N,2-dimethyl-4-oxo-1,4-dihydro-1,8-naphthyridine-3-carboxamide (compound 52)

9.1: (5-Chlorothiophen-2-yl)acetic acid 1.2 g (29.8 mmol) of sodium hydroxide powder are added to 19.7 g (158.8 mmol) of FAMSO, the mixture is heated at 70° C. for 30 minutes, 3 g (19.8 mmol) of 5-chloro-2-thiophenecarboxaldehyde are then added and the mixture is heated again at 70° C. overnight. At room temperature, 850 ml of water are added and the aqueous phase is then extracted with ethyl acetate (3×430 ml). The combined organic phases are washed with saturated aqueous NaCl solution, dried over Na$_2$SO$_4$, filtered and concentrated under reduced pressure. 6.7 g of product are obtained in the form of a brown oil, which is used without purification in the following step.

MH$^+$: 253 (tr: 7.6 min condition 1)

33 ml (132 mmol) of a solution (4M) of HCl in dioxane are added to 6.7 g of the compound obtained from the preceding step, dissolved in ethanol (44 ml), and the mixture is heated at 80° C. for 2 hours 15 minutes. The mixture, cooled to RT, is diluted with ethyl acetate (400 ml) and washed with saturated aqueous NaHCO$_3$ solution (350 ml) and then with NaCl (200 ml). The organic phase is then dried over Na$_2$SO$_4$, filtered and concentrated under reduced pressure. The residue is purified by flash chromatography on a column of silica gel (eluent: heptane/dichloromethane), with a gradient of 0% to 50% dichloromethane. 1.93 g of product are obtained, in the form of a brown oil. Yield: 32%. MH$^+$: 205.1 (tr: 5.33 min condition 1)

0.97 g (23.1 mmol) of lithium hydroxide monohydrate is added to 1.93 g (6.6 mmol) of the compound obtained from the preceding step, dissolved in a solvent mixture (1/1/1 THF/methanol/water) (33 ml). The mixture is heated at 70° C. for 2 hours, cooled to RT and acidified to pH 1 by adding 23 ml of aqueous HCl solution (1N) and then extracted with dichloromethane (twice 30 ml). The combined organic phases are washed with saturated aqueous NaCl solution, dried over Na$_2$SO$_4$, filtered and concentrated under reduced pressure. 1.44 g of product are obtained in the form of a brown powder, which is used without purification in the following step. MH$^+$: 176 (tr: 12.3 min condition GC Cl/CH4+).

9.2: 2-(5-Chlorothiophen-2-yl)-N-[(1-ethylpyrrolidin-2-yl)methyl]-acetamide

Using the same procedure as that described in Example 4, step 4.1, starting with 1.77 g (10 mmol) of compound obtained from the preceding step, 5.4 g (40 mmol) of 1-ethylpyrrolidinylmethylamine, 6.4 g (20 mmol) of TBTU and 2.58 g (20 mmol) of diisopropylethylamine in anhydrous DMF (100 ml), 1.62 g of product are obtained in the form of a white powder. Yield: 56%. Melting point: MH$^+$: 287.1 (tr: 4.1 min., condition 1).

9.3 1-Ethyl-7-[5-(2-{[(1-ethyl pyrrolidin-2-yl)methyl]amino}-2-oxoethyl)-thiophen-2-yl]-N,2-dimethyl-4-oxo-1,4-dihydro-1,8-naphthyridine-3-carboxamide (compound 52)

Using the same procedure as that described in Example 1, step 1.12, starting with 1 g (3.5 mmol) of the compound obtained from step 9.2, 1.3 g (4.5 mmol) of the compound obtained from step 1.7, 0.24 g (0.2 mmol) of tetrakis(triphenylphosphine)palladium and 14 ml of saturated NaHCO$_3$ solution, in a 2/1 mixture of DME/EtOH (35 ml), 0.05 g of product is obtained, in the form of a white powder. Yield: 2%. Melting point: 250° C. MH$^+$: 497 (tr: 5.3 min., condition 1).

$^1$H NMR (400 MHz, DMSO-d$_6$), δ (ppm): 11.7 (s, 1H); 11.1 (q, 1H, 4.5 Hz); 8.43 (d, 1H, 8.3 Hz); 8.0 (m, 1H); 7.95 (broad s, 1H); 7.82 (d, 1H, 8.3 Hz); 7.80 (d, 1H, 3.7 Hz); 7.0 (d, 1H, 3.7 Hz); 4.5 (m, 2H); 3.72 (s, 2H); 3.27 (m, 1H); 3.01 (m, 1H); 2.89 (m, 1H); 2.8 (t, 3H, 4.5 Hz); 2.76 (m, 1H); 2.42 (m, 1H); 2.18 (m, 1H); 2.07 (m, 1H); 1.76 (m, 1H); 1.61 (m, 2H); 1.48 (m, 1H); 1.3 (t, 3H, 6.9 Hz); 1.01 (t, 3H, 7.2 Hz);

EXAMPLE 10

2-Amino-1-ethyl-N-methyl-4-oxo-7-{4-[2-(pyrid-2-ylamino)ethyl]phenyl}-1,4-dihydro-1,8-naphthyridine-3-carboxamide hydrochloride (compound 64)

10.1 N-[2-(4-Bromophenyl)ethyl]pyrid-2-amine

In a sealed tube, a mixture of 1.9 g (20.4 mmol) of 2-aminopyridine and 6.1 g (30.6 mmol) of 4-bromophenethylamine dissolved in butanol (10 ml) is heated at 230° C. for 1 hour by microwave. The mixture, cooled to room temperature, is poured into water (50 ml) and extracted with ethyl acetate (3×100 ml), and the combined organic phases are dried over sodium sulfate, filtered and concentrated. The residue is purified by flash chromatography on a column of silica gel (eluent: dichloromethane/ethyl acetate, from 0% to 50% ethyl acetate). 1.4 g of product are obtained in the form of a white powder. Yield: 24%. Melting point: 71° C. MH$^+$: 278.1 (tr: 3.71 min., condition 1).

10.2: 2-Amino-1-ethyl-N-methyl-4-oxo-7-{4-[2-(pyrid-2-ylamino)ethyl]-phenyl}-1,4-dihydro-1,8-naphthyridine-3-carboxamide hydrochloride (compound 64)

Using the same procedure as that described in Example 1, step 1.12, starting with 0.3 g (1.1 mmol) of the compound obtained from step 10.1, 0.345 g (1.2 mmol) of the compound obtained from step 1.7, 0.06 g (0.05 mmol) of tetrakis(triphenylphosphine)palladium and 4.7 ml of saturated NaHCO$_3$ solution, in a 2/1 mixture of DME/EtOH (15 ml), 0.12 g of product thus obtained is taken up in methanol (3 ml) and 0.03 ml of concentrated 36% HCl is added. 0.130 g of product is obtained, in the form of a white powder. Yield: 25%. Melting point: 242° C. MH$^+$: 497 (tr: 5.33 min., condition 1).

$^1$H NMR (400 MHz, DMSO-d$_6$), δ (ppm): 13.7 (s, 1H); 11.73 (m, 1H); 11.12 (q, 1H, 4.5 Hz); 8.9 (s, 1H); 8.52 (d, 1H, 8.1 Hz); 8.17 (d, 2H, 8.3 Hz); 8.02 (broad s, 1H); 7.96 (d, 1H, 8.1 Hz); 7.89 (m, 1H); 7.51 (d, 2H, 8.3 Hz); 7.08 (d, 1H, 9.1 Hz); 6.84 (broad t, 1H, 6.7 Hz); 4.6 (m, 2H); 3.69 (m, 2H); 3.01 (t, 2H, 7.2 Hz); 2.81 (d, 3H, 4.5 Hz); 1.32 (t, 3H, 6.9 Hz).

Compounds 1, 2, 3, 4, 5, 6, 7, 8, 9, 10, 11, 12, 13, 14, 15, 16, 17, 18, 20, 23, 25, 28, 30, 31, 45, 46, 47, 51, 52, 56, 62, 63 and 64 were synthesized according to the synthetic route described in Example 1. Compounds 35, 36, 37, 38, 39, 40, 41, 42, 44, 48, 49, 50, 53, 54 and 55 were synthesized according to the synthetic route described in Example 2. Compounds 29, 34 and 43 were synthesized according to the synthetic route described in Example 3.

The tables that follow illustrate the chemical structures and the physical properties of a few examples of compounds according to the invention.

Table 1 illustrates compounds of formula (Ia) corresponding to compounds of formula (I) for which U represents a carbonyl group and R6=—(CH$_2$)$_n$-L.

Table 2 illustrates compounds of formula (Ib) corresponding to compounds of formula (I) for which U represents a carbonyl group, Y, V and W represent a —CH— group, Z represents a carbon atom, R7 represents a hydrogen atom and R6=—(CH$_2$)$_n$-L.

Table 3 illustrates compounds of formula (Ic) corresponding to compounds of formula (I) for which U represents a —CH$_2$— group, Z, Y, V and W represent a —CH— group, R7 represents a hydrogen atom, and R6=-(CH$_2$)$_n$-L.

In these tables:

- in the "salt" column, "-" represents a compound in free base form, whereas "HCl" represents a compound in hydrochloride form, and the ratio in parentheses is the (acid:base) ratio,
- Me, Et, n-Pr, i-Pr, n-Bu and i-Bu represent, respectively, methyl, ethyl, n-propyl, isopropyl, n-butyl and isobutyl groups, and
- Ph and Bn represent, respectively, phenyl and benzyl groups.

TABLE 1

(Ia)

in which R6 = (CH$_2$)$_n$—L, (*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (°C.) |
|---|---|---|---|---|---|---|---|---|---|---|---|---|---|---|---|
| 1 | 1 | 0 | CH3 | H | H | H | phenyl | Et | CH | CH | CH | CH | — | 7.2 (3) 97% 456.36 | 299 |
| 2 | 1 | 1 | CH3 | H | H | CH3 | N-ethylpyrrolidinyl | Et | CH | CH | CH | CH | — | 9.6 94.5% 505.4 | 138 |
| 3 | 1 | 0 | CH3 | H | H | H | 3-pyridyl | Et | CH | CH | CH | CH | HCl (1.07) | 6.4(3) 100% 457 | 270 |
| 4 | 1 | 0 | CH3 | H | H | H | 2-pyridyl | Et | CH | CH | CH | CH | HCl (1.07) | 6.7 (3) 95.6% 457 | 258 |

TABLE 1-continued

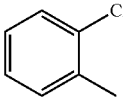

(Ia)

in which R6 = (CH₂)ₙ—L,
(*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (° C.) |
|---|---|---|---|---|---|---|---|---|---|---|---|---|---|---|---|
| 5 | 1 | 0 | CH3 | H | H | H | 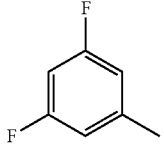 | Et | CH | CH | CH | CH | — | 7.9 (3) 96% 490 | >260 |
| 6 | 1 | 0 | CH3 | H | H | H | 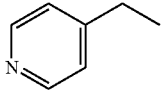 | Et | CH | CH | CH | CH | — | 8.1 100% 492 | >260 |
| 7 | 1 | 1 | CH3 | H | H | H | 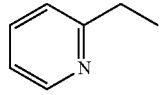 | Et | CH | CH | CH | CH | HCl (1.07) | 4.9 (3) 97% 471.1 | 230 |
| 8 | 1 | 1 | CH3 | H | H | H | 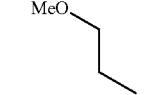 | Et | CH | CH | CH | CH | HCl (1.07) | 5.1 (3) 96% 471.1 | 268 |
| 9 | 1 | 2 | CH3 | H | H | H |  | Et | CH | CH | CH | CH | — | 6.2 98.4% 438.5 | 262 |
| 10 | 1 | 0 | CH3 | H | H | H |  | Et | CH | CH | CH | CH | — | 6.3 96.5% 420.3 | >260 |
| 11 | 1 | 0 | CH3 | H | H | H |  | Et | CH | CH | CH | CH | — | 6.6 99.2% 422.5 | 315 |
| 12 | 1 | 0 | CH3 | H | H | H | 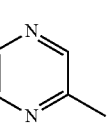 | Et | CH | CH | CH | CH | — | 14.3 (2) 98.7% 448.3 | 300 |
| 13 | 1 | 0 | CH3 | H | H | H | 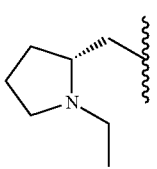 | Et | CH | CH | CH | CH | — | 6.6 97% 458.3 | 290 |
| 14 | 1 | 1 | CH3 | H | H | H |  | Et | CH | CH | CH | CH | — | 4.8 97.4% 491.3 | 270 |

TABLE 1-continued (Ia)

Structure with R1, R2, R3, R4, R5, R6, V, W, Y, Z substituents on a 1,8-naphthyridine core.

in which R6 = (CH$_2$)$_n$—L, (*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (° C.) |
|---|---|---|---|---|---|---|---|---|---|---|---|---|---|---|---|
| 15 | 1 | 1 | CH3 | H | H | H | N-ethylpyrrolidin-2-yl-methyl | Et | CH | CH | CH | CH | — | 4.8 97.9% 491.3 | 262 |
| 16 | 1 | 0 | CH3 | H | H | H | 4-methylpyrimidin-6-yl | Et | CH | CH | CH | CH | — | 6.59 6.5% 458.3 | >280 |
| 17 | 1 | 0 | CH3 | H | H | H | 4-methylpyridin-3-yl | Et | CH | CH | CH | CH | HCl (1.07) | 5.07 96% 457.3 | 250 |
| 18 | 1 | 2 | CH3 | H | H | H | 3-morpholinopropyl | Et | CH | CH | CH | CH | HCl (1.07) | 5.34 100% 493.2 | 220-222 |
| 19 | 1 | 0 | CH3 | H | H | H | 2-methylpyridin-3-yl | Et | CH | CH | N | CH | HCl (1.15) | 6.3 97.7% 458.3 | 268-288 |
| 20 | 1 | 0 | CH3 | H | CH3 | H | 2-methylpyridin-3-yl | Et | CH | CH | CH | CH | HCl (1.07) | 7.7 97.7% 471.1 | 188 |
| 21 | 1 | 0 | CH3 | H | H | H | 2-methylpyridin-3-yl | Et | CH | CH | CH | N | — | 6.5 96.3% 458.1 | 266 |
| 22 | 1 | 1 | CH3 | H | H | H | (4-ethylmorpholin-3-yl)methyl | Et | CH | CH | CH | CH | HCl (1.15) | 5.4 95% 507.1 | 188-190 |
| 23 | 1 | 1 | CH3 | H | H | H | (4-ethylmorpholin-3-yl)methyl | Et | CH | CH | CH | N | HCl (1.07) | 4.6 97.8% 508.4 | 199 |

TABLE 1-continued
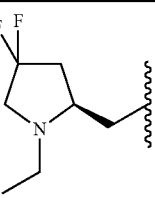
in which R6 = (CH$_2$)$_n$—L,
(*) LC/UV/MS conditions: if they are not mentioned, the conditions 1 are the ones used.
| No. | m | n | R1 | R3 | R4 | R5 | R6 | R2 | V | W | Y | Z | Salt | LCMS tr min. (*) purity MH+ | Melting point (° C.) |
|---|---|---|---|---|---|---|---|---|---|---|---|---|---|---|---|
| 24 | 1 | 1 | CH3 | H | H | H | 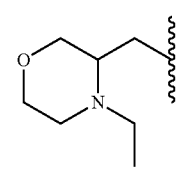 [SMILES: *CC1COCCN1CC] | Et | CH | CH | CH | CH | HCl (1.07) | 6.04 100% 527.3 | 266 |
| 25 | 1 | 1 | CH3 | H | CH3 | H | 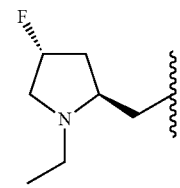 | Et | CH | CH | CH | CH | HCl (1.07) | 5.7 96.5% 521.3 | 190 |
| 26 | 1 | 1 | CH3 | H | H | H | 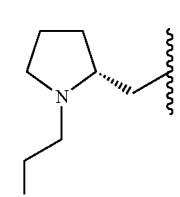 | Et | CH | CH | CH | CH | HCl (1.07) | 5.2 96.7% 509.3 | 170 |
| 27 | 1 | 1 | CH3 | H | H | H | 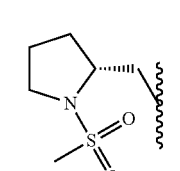 | Et | CH | CH | CH | CH | HC (1.07) | 4.64 509.3 | 180 |
| 28 | 1 | 1 | CH3 | H | H | H | 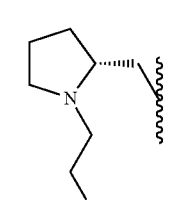 | Et | CH | CH | CH | CH | — | 6.7 97.2% 541.2 | >260 |
| 29 | 1 | 1 | CH3 | H | H | H |  | Et | CH | CH | N | CH | HCl (1.07) | 4.97 92% 510.2 | 194 |

TABLE 1-continued (Ia)

in which R6 = (CH₂)ₙ—L,
(*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (° C.) |
|---|---|---|---|---|---|---|---|---|---|---|---|---|---|---|---|
| 30 | 1 | 1 | CH3 | H | H | H | pyrrolidine-N-CH2CF3 | Et | CH | CH | CH | CH | — | 7.1 99.1% 545.2 | >260 |
| 31 | 1 | 1 | CH3 | H | H | H | pyrrolidine-N-CH2CHF2 | Et | CH | CH | CH | CH | HCl (1.07) | 9.8 (2) 96.4% 527.3 | 214-228 |
| 32 | 1 | 1 | CH3 | H | H | H | morpholine-N-iPr | Et | CH | CH | CH | CH | HCl (1.07) | 9.1 (2) 93.2% 521.3 | 192 |
| 33 | 1 | 1 | CH3 | H | H | H | morpholine-N-cyclopropyl | Et | CH | CH | CH | CH | HCl (1.07) | 5.5 97.8% 519.2 | 250 |
| 34 | 1 | 1 | CH3 | H | H | H | pyrrolidine-N-CH2CHF2 | Et | CH | CH | N | CH | HCl (1.07) | 5.2 92.1% 528.2 | 260 |
| 35 | 1 | 0 | CH3 | H | H | H | thiazole | Et | CH | CH | CH | CH | — | 7.2 94.4% 463.2 | 303 |
| 36 | 1 | 1 | CH3 | H | H | H | N-methylimidazole | Et | CH | CH | CH | CH | HCl (1.07) | 5.2 96.3% 474.2 | 270 |

TABLE 1-continued

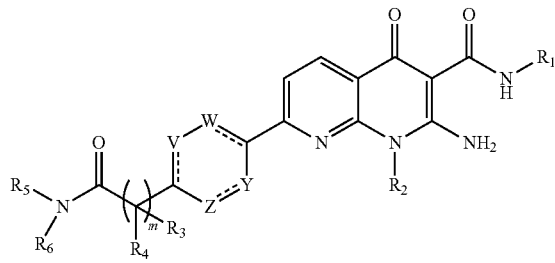

(Ia)

in which R6 = (CH₂)ₙ—L,
(*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (°C.) |
|---|---|---|---|---|---|---|---|---|---|---|---|---|---|---|---|
| 37 | 1 | 2 | CH3 | H | H | H | 3-pyridyl-propyl | Et | CH | CH | CH | CH | HCl (1.07) | 5.4 98.7% 485.2 | 222 |
| 38 | 1 | 3 | CH3 | H | H | H | morpholino-butyl | Et | CH | CH | CH | CH | HCl (1.07) | 5.2 98.2% 507.2 | 196 |
| 39 | 1 | 2 | CH3 | H | H | H | 2-pyridyl-propyl | Et | CH | CH | CH | CH | HCl (1.07) | 5.4 96.5% 485.2 | 248 |
| 40 | 1 | 2 | CH3 | H | H | H | phenyl-propyl | Et | CH | CH | CH | CH | — | 7.7 99.3% 484.2 | 270 |
| 41 | 1 | 3 | CH3 | H | H | H | phenyl-butyl | Et | CH | CH | CH | CH | — | 8.3 (3) 97.1% 498.3 | 278 |
| 42 | 1 | 2 | CH3 | H | H | H | 1-methyl-pyrrol-2-yl-ethyl | Et | CH | CH | CH | CH | — | 7.3 96.4% 487.2 | 252 |
| 43 | 1 | 1 | CH3 | H | H | H | 1-ethyl-pyrrolidin-2-yl-methyl | Et | CH | S | N | — | HCl (1.07) | 5.1 96.2% 498.2 | 228 |
| 44 | 1 | 0 | CH3 | H | H | H | 6-methyl-pyridin-2-yl | 3-methoxypropyl | CH | CH | CH | CH | HCl (1.07) | 6.45 99.8% 501.3 | 230 |
| 45 | 1 | 0 | CH3 | H | H | H | 1-(difluoromethyl)-3-methylpyrrolidinyl | Et | CH | CH | CH | CH | — | 5.4 98% 513.2 | 267 |

TABLE 1-continued
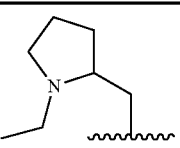
in which R6 = (CH$_2$)$_n$—L,
(*) LC/UV/MS conditions: if they are not mentioned, the conditions 1 are the ones used.
| No. | m | n | R1 | R3 | R4 | R5 | R6 | R2 | V | W | Y | Z | Salt | LCMS tr min. (*) purity MH+ | Melting point (°C.) |
|---|---|---|---|---|---|---|---|---|---|---|---|---|---|---|---|
| 46 | 2 | 1 | CH3 | H | H | H | 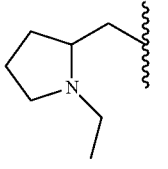 | Et | CH | CH | CH | CH | — | 9.8(2) 97.6% 505.4 | 218 |
| 47 | 3 | 1 | CH3 | H | H | H | 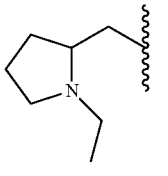 | Et | CH | CH | CH | CH | — | 5.7 97.6% 519.4 | 230 |
| 48 | 1 | 1 | —(CH$_2$)$_2$—CH$_3$ | H | H | H | 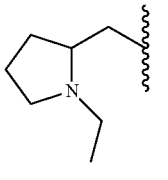 | Et | CH | CH | CH | CH | — | 5.9 96.8% 519.4 | 264 |
| 49 | 1 | 1 | CH3 | H | H | H | 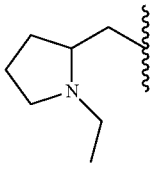 [SMILES: *CC1CCCN1CC] | CH$_2$CF | CH | CH | CH | CH | — | 5.6 97.1% 545.2 | 300 |
| 50 | 1 | 1 | CH3 | H | H | H | 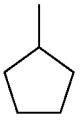 | 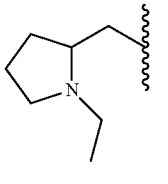 [SMILES: *CC1CCCN1CC] | CH | CH | CH | CH | — | 5.7 98.7% 531.4 | 222 |
| 51 | 4 | 1 | CH3 | H | H | H | 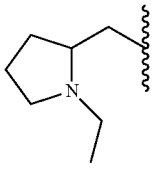 [SMILES: *CC1CCCN1CC] | Et | CH | CH | CH | CH | — | 5.9 94.2% 533.4 | 180 |
| 52 | 1 | 1 | CH3 | H | H | H | 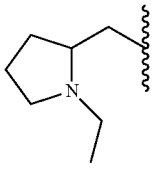 [SMILES: *CC1CCCN1CC] | Et | — | S | CH | CH | — | 5.3 98% 497 | 250 |

TABLE 1-continued

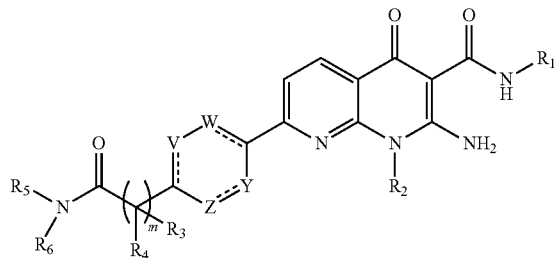

in which R6 = (CH$_2$)$_n$—L, (*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (° C.) |
|---|---|---|---|---|---|---|---|---|---|---|---|---|---|---|---|
| 53 | 1 | 1 | CH3 | H | H | H | (1-ethylpyrrolidin-2-yl)methyl | IsoBu | CH | CH | CH | CH | — | 5.66 98.9% 519.3 | 233 |
| 54 | 1 | 1 | CH3 | cyclopropyl | H |  | (1-ethylpyrrolidin-2-yl)methyl | Et | CH | CH | CH | CH | — | 5.8 99.3% 517.2 | 189 |
| 55 | 1 | 1 | CH3 | H | H | H | (1-ethylpyrrolidin-2-yl)methyl | Et | — | N | CH | S | — | 5.06 99.6% 498.2 | 214 |
| 56 | 1 | 1 | CH3 | H | H | H | (1-ethylpyrrolidin-2-yl)methyl | Et | CH | CF | CH | CH | — | 5.47 98% 509.2 | 253 |

TABLE 1-continued

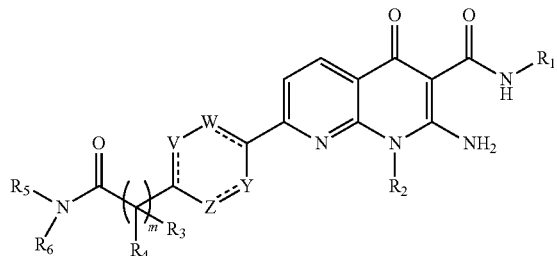

(Ia)

in which R6 = (CH₂)ₙ—L, (*) LC/UV/MS conditions: if they are not mentioned, the conditions 1 are the ones used.

| No. | m | n | R1 | R3 | R4 | R5 | R6 | R2 | V | W | Y | Z | Salt | LCMS tr min. (*) purity MH+ | Melting point (° C.) |
|---|---|---|---|---|---|---|---|---|---|---|---|---|---|---|---|
| 57 | 1 | 1 | CH3 | H | H | H | (1-ethylpyrrolidin-2-yl)methyl | Et | CCl | CH | CH | CH | HCl (1.07) | 5.58 96.6% 525.2 | 228 |
| 58 | 1 | 1 | CH3 | H | H | H | (1-ethylpyrrolidin-2-yl)methyl | Et | CF | CH | CH | CH | — | 5.45 93.2% 509.2 | 275 |
| 59 | 1 | 1 | CH3 | H | H | H | (1-ethylpyrrolidin-2-yl)methyl | Et | CCH3 | CH | CH | CH | — | 5.51 96% 505.2 | 277 |
| 60 | 1 | 1 | CH3 | H | H | H | (1-ethylpyrrolidin-2-yl)methyl | cyclopropylmethyl | CH | CH | CH | CH | — | 5.59 98.3% 517.2 | 260 |
| 61 | 1 | 1 | CH3 | H | H | H | (1-ethylpyrrolidin-2-yl)methyl | Et | CH | CCH3 | CH | CH | — | 5.52 92% 505.2 | 178 |

TABLE 2

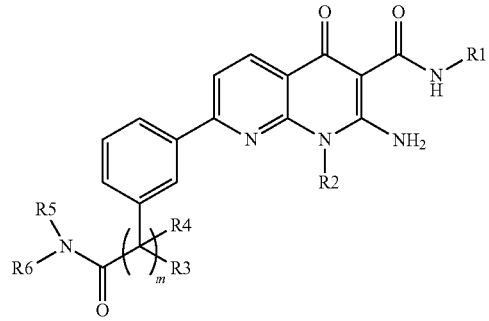

(Ib)

in which Y, V and W represent a —CH— group. Z represents a carbon atom, R7 represents a hydrogen atom and R6 = —(CH$_2$)$_n$—L
(*) LC/UV/MS conditions: if they are not mentioned, the conditions 1 are the ones used.

| No. | m | n | R1 | R3 | R4 | R5 | R6 | R2 | Salt | LCMS tr min. (*) purity MH+ | Melting point (° C.) |
|---|---|---|---|---|---|---|---|---|---|---|---|
| 62 | 1 | 1 | CH3 | H | H | H | pyrrolidinyl-ethyl (N-ethyl) | Et | HCl | 5.4 (1.07) 97.7% 491.4 | 213 |
| 63 | 1 | 0 | CH3 | H | H | H | 2-methylpyridinyl | Et | HCl | 6.3 (1.07) 99.6% 457.3 | 176 |

TABLE 3

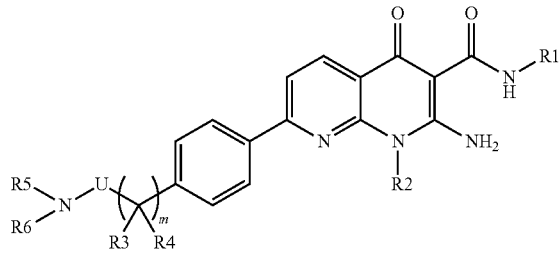

(Ic)

in which U = —CH$_2$—, V and W represent a —CH— group, Z represents a carbon atom, R7 represents a hydrogen atom and R6 = —(CH$_2$)$_n$—L
(*) LC/UV/MS conditions: if they are not mentioned, the conditions 1 are the ones used.

| No. | m | n | R1 | R3 | R4 | R5 | R6 | R2 | Salt | LCMS tr min. (*) purity MH+ | Melting point (° C.) |
|---|---|---|---|---|---|---|---|---|---|---|---|
| 64 | 1 | 0 | CH3 | H | H | H | 2-methylpyridinyl | Et | HCl | 5.57 (1.07) 97.5% 443.2 | 242 |

The compounds according to the invention underwent pharmacological trials to determine their inhibitory effect on proteins with tyrosine kinase activity.

By way of example, their inhibitory effects on the tyrosine kinase activity of PDGF-R and/or FLT3 were measured in vitro in cell models.

The inhibitory activity with respect to the PDGF or FLT3 receptors is given by the concentration that inhibits 50% of the proliferation activity of Baf3 tel/PDGF or MV4-11 cells, respectively.

Measurement of Inhibition of the Tyrosine Kinase Activity of the PDGF Beta (PDGF-Rβ) (Baf-3 tel/PDGFIRβ) Receptor:

This test consists in evaluating the effects of the compounds on the tyrosine kinase activity of the PDGF beta receptor.

The inhibitory effect of the compounds according to the invention towards the tyrosine kinase activity of the PDGF-R receptor was evaluated on the murine haematopoietic cell line BaF/3 transfected with a plasmid coding for the fusion protein Tel/PDGF-Rβ. This fusion protein is found in chronic myelomonocytic myeloid leukaemias (CMML). It comprises the N-terminal part of the Tel transcription factor and the transmembrane and intracellular part of the PDGF-Rβ receptor. This fusion protein is present in dimerized form (presence of an oligomerization domain in the N-terminal part of Tel) and, as a result, leads to constitutive activity of the kinase domain of PDGF-Rβ. This line BaF3 Tel/PDGF has been described in the literature several times and especially, in detailed manner, in the article by M. Carroll et al., PNAS, 1996, 93, 14845-14850.

The BaF3 Tel/PDGF cells are washed with phosphate buffer and inoculated in 96-well plates, at a density of $5 \times 10^4$ cells/ml (100 ml per well), in RPMI 1640 containing 10% FCS, in the presence or absence of the test compounds. After incubation for 72 hours, the viable cells are quantified by measuring the cellular ATP by means of the CellTiter-Glo® kit (Promega, Cat G7571). The cells are treated according to the instructions given by the kit manufacturer, and the luminescence is measured using a Luminoskan (Ascent, Labsystem) with the following parameters: measurement: single; integration time: 1000 ms, lag time: 5 s.

It is thus seen that the compounds according to the invention have inhibitory activity on the tyrosine kinase activity of PDGF-Rβ. This activity is given by the concentration that inhibits 50% of the proliferation of the BaF3 Tel/PDGF cells ($IC_{50}$). The $IC_{50}$ values for the compounds according to the invention are less than 1.0 µM.

For example, compounds 6, 14, 19, 22, 24, 29, 33, 35, 41, 47 and 48 had an $IC_{50}$, respectively, of 11, 11, 27, 0.07, 2, 35, 4.7, 3.7, 5.5, 48 and 162 nM in the test of measurement of the tyrosine kinase activity of the PDGF receptor.

Measurement of Inhibition of the Tyrosine Kinase Activity of the PDGF Alpha Receptor:

The inhibitory effect of the compounds according to the invention towards the tyrosine kinase activity of the PDGF alpha receptor was evaluated on the EOL-1 cell line, which line is established from a leukaemia of constitutively active chronic eosinophilic leukaemia (CEL) type. The EOL-1 line has been described as expressing the fusion protein FIP1L1-PDGF-Rα and is sensitive to kinase inhibitors in proliferation tests (Cools J. et al., Blood 2004, 103, 2802-2005). The inhibitory activity is correlated to the inhibition of cell growth.

The EOL-1 cells are washed with PBS buffer and inoculated in 96-well plates, at a density of $5 \times 10^4$ cells/ml (100 µL per well), in RPMI 1640 containing 10% FCS, in the presence or absence of the test compounds. After incubation for 72 hours, the viable cells are quantified by measuring the cellular ATP by means of the CellTiter-Glo® kit (Promega, Cat G7571). The cells are treated according to the instructions given by the kit manufacturer, and the luminescence is measured using a Luminoskan (Ascent, Labsystem) with the following parameters: measurement: single; integration time: 1000 ms, lag time: 5 s.

It is thus seen that the compounds according to the invention have inhibitory activity on the tyrosine kinase activity of PDGF-Rα. This activity is given by the concentration that inhibits 50% of the proliferation of the EOL-1 cells. The $IC_{50}$ values for the compounds according to the invention are less than 1.0 µM.

For example, compounds 5, 6, 22, 19, 24, 33, 35, 43, 50 and 51 had an $IC_{50}$, respectively, of 1.6, 0.57, <0.01, 0.4, <0.01, <0.01, 0.8, 29.7, 3.2 and 92.7 nM in the test of measurement of the tyrosine kinase activity of the PDGF alpha receptor.

Besides their inhibitory properties on PDGF-R tyrosine kinase, it is also seen that the compounds in accordance with the invention have inhibitory properties on the tyrosine kinase activity of the FLT3 receptor, as described below.

Measurement of Inhibition of the Tyrosine Kinase Activity of the FLT3 Receptor

The inhibitory effect of the compounds according to the invention towards the tyrosine kinase activity of the FLT3 receptor was evaluated on an MV4-11 cell line, which line is established from a leukaemia of constitutively active AML type bearing an FLT3ITD mutant. The inhibitory activity is correlated to the inhibition of cell growth, according to the protocols described by Spiekermann, K. et al., Blood, 2003, 101, (4) 1494-1504 and O'Farrell, A.-M. et al., Blood, 2003, 101, (9) 3597-3605.

MV4-11 cells are washed with PBS buffer and inoculated in 96-well plates, at a density of $1 \times 10^5$ cells/ml (100 µL per well), in RPMI 1640 containing 10% FCS, in the presence or absence of the test compounds. After incubation for 72 hours, the viable cells are quantified by measuring the cellular ATP by means of the CellTiter-Glo® kit (Promega, Cat G7571). The cells are treated according to the instructions given by the kit manufacturer, and the luminescence is measured using a Luminoskan (Ascent, Labsystem) with the following parameters: measurement: single; integration time: 1000 ms, lag time: 5 s.

The inhibitory activity with respect to the FLT3 receptor is given by the concentration that inhibits 50% of the proliferation of the MV4-11 cells. It is thus seen that compounds according to the invention have inhibitory activity on the tyrosine kinase activity of the FLT3 receptor with $IC_{50}$ values of less than 1.0 µM.

For example, compounds 3, 4, 5, 6, 14, 16, 19, 22, 24, 33 and 35 had an $IC_{50}$, respectively, of 0.33, 0.21, 0.19, 0.1, 0.34, 0.182, 0.1, 0.13, 0.19, 0.056 and 0.083 µM, in the test of measurement of the tyrosine kinase activity of the FLT3 receptor.

Ex vivo activity of the compounds of the invention was measured. These compounds are thus administered orally to female Balb/c mice at a dose of 10, 30 or 100 mg/kg in suspension or in solution in a vehicle such as methylcellulose/Tween and the inhibition of the tyrosine kinase activity is measured in vitro in a cell test, using plasma collected at 15 minutes, 1 hour and 4 hours.

Measurement of Inhibition of the Tyrosine Kinase Activity of the PDGF Alpha Receptor Ex Vivo:

1) Protocol for Administration of the Products to the Mice

The products are prepared in a mortar with 0.5% Tween 80 and 0.6% methylcellulose qs final volume. Depending on the case, preparations of different vehicles may be used: water, mixture of labrasol solutol 5% glucose-water. The suspended or dissolved products are administered by gavage (10 ml/kg) to female Balb/c mice 8 to 15 weeks old.

The animals are then collected at the time given by the protocol (15 min, 1 hour, 4 hours, 16 hours).

The animals are anaesthetized by intraperitoneal injection (10 ml/kg) of a ketamine (0.1 g/kg)-xylazine (20 mg/kg) mixture. A laparotomy is performed to expose the descending abdominal aorta and inferior vena cava assembly. The blood sample is collected from the vein or the artery using a dry syringe and needle. The blood is immediately transferred into heparin lithium tubes (BD microtainer). Centrifugation for 3 minutes at 12 000 rpm allows recovery of the plasma, on which the biochemical test may be performed after storage by freezing at −20° C.

2) Preparation of the HEK Tel/PDGF-R Cells and Measurement of the Phosphorylation of PDGF-R In order to detect the ex vivo activity of the products using the mouse plasmas, the HEK cells are transiently transfected beforehand with an expression vector coding for the fusion protein Tel/PDGF-R (fusion protein described previously). After 24 hours of transfection, the cells are deprived of serum overnight and then incubated for 30 minutes with the animal plasmas treated with the products of the invention. The cells are then lysed in RIPA buffer, and detection of the phosphorylation of PDGF-Rβ is then performed via the ELISA technique, using a commercial kit (R&D Systems, DYC1767). The results are expressed as a percentage of inhibition of the autophosphorylation.

In this test of measurement of the ex vivo activity, the effect of the compounds of the invention is quantified by the percentage of inhibition of phosphorylation of the kinase domain of the PDGF-Rβ receptor in HEK cells, induced by the inhibitory activity of the product present in the plasma of the treated animals, as described in the following table:

| Administration 30 mg/kg po Compound No. | % inhibition of autophosphorylation of PDGFR tyrosine kinase in HEK cells | | |
|---|---|---|---|
| | 15 min | 1 h | 4 h |
| 18 | 55 | 62 | 17 |
| 24 | 85 | 57 | 74 |
| 26 | 58 | 67 | 20 |
| 31 | 85 | 68 | 42 |
| 33 | 80 | 82 | 75 |
| 34 | 73 | 64 | 58 |

Thus, according to one of the subjects of the present invention, the compounds of formula (I) have very advantageous inhibitory activity on phosphorylation of the kinase domain of the PDGF-Rβ receptor in HEK cells, induced by the inhibitory activity of the product present in the plasma of the treated animals.

The compounds according to the invention are thus inhibitors of protein kinases, especially of the PDGF alpha and beta tyrosine kinase receptors, and, for some of them, also of the FLT3 tyrosine kinase receptor.

The compounds according to the invention may thus be used for the preparation of medicaments, in particular protein kinase-inhibiting medicaments.

These are protein kinase-inhibiting medicaments, especially medicaments that inhibit the PDGF-R tyrosine kinase receptor and possibly the FLT3 tyrosine kinase receptor.

Thus, according to another of its aspects, a subject of the invention is medicaments that comprise a compound of formula (I), or an addition salt thereof with a pharmaceutically acceptable acid, or alternatively a solvate of the compound of formula (I).

These medicaments find their therapeutic use especially in the treatment of diseases associated with the activity of protein kinases and especially proliferative diseases such as liquid-tumour cancers, chronic or acute leukaemias, lymphocytic lymphomas, Hodgkin's disease and myeloproliferative syndromes, and myelodysplastic syndromes, and also solid-tumour cancers, for example lung cancer (NSCLC), bone cancer, pancreatic cancer or skin cancer, Kaposi's sarcoma, intraocular melanomas, breast cancer, uterine cancer, cervical cancer, ovarian cancer, cancer of the endometrium, of the vagina, of the vulva, of the urethra, of the penis or of the prostate, fallopian tube carcinomas, cancers such as GIST and of the anal region, of the rectum, of the small intestine, bowel cancer, stomach cancer, cancer of the oesophagus, of the endocrine, thyroid, parathyroid or adrenal glands, soft-tissue sarcomas, Ewing's sarcomas, osteosarcomas, dermatofibrosarcoma and other fibrosarcomas, cancer of the bladder or of the kidney, neoplasms of the central nervous system, spinal column tumours and desmoid tumours, brain stem gliomas and glioblastomas, pituitary adenomas and metastases thereof.

Another aspect of the invention comprises a combination between at least one compound according to the invention and at least one chemotherapy agent.

Specifically, the compounds of the present invention may be used alone or as a mixture with at least one chemotherapy agent, which may be chosen from cytotoxic agents and antiangiogenic agents. For example, the antiangiogenic agent may be a compound that inhibits the kinase activity of VEGF-R or a growth factor antagonist compound.

It is also possible to combine the compounds according to the invention with a radiation treatment.

The combinations of the compounds according to the invention with the chemotherapy agents mentioned above and/or with radiation are another subject of the present invention.

The chemotherapy agents mentioned above and/or the radiation may be administered simultaneously, separately or sequentially. The treatment will be adapted by the doctor as a function of the patient to be treated.

These medicaments also find their therapeutic use in non-malignant proliferative diseases, for instance restenosis, atherosclerosis, thrombosis, cardiac insufficiency, cardiac hypertrophy, pulmonary arterial hypertension, fibrosis, diabetic nephropathy, glomerulonephritis, chronic pyelonephritis, haemangiomas, autoimmune diseases such as psoriasis, sclerodermatitis and immunosuppression (for example graft rejection).

According to another of its aspects, the present invention relates to pharmaceutical compositions containing, as active principle, a compound according to the invention. These pharmaceutical compositions contain an effective dose of at least one compound according to the invention, or a pharmaceutically acceptable salt thereof, or alternatively a solvate of the said compound, and also at least one pharmaceutically acceptable excipient.

The said excipients are chosen according to the pharmaceutical form and the desired mode of administration, from the usual excipients known to those skilled in the art.

In the pharmaceutical compositions of the present invention for oral, sublingual, subcutaneous, intramuscular, intravenous, topical, intratracheal, intranasal, transdermal or rectal administration, the active principle of formula (I) above, or the possible salt or solvate thereof, may be administered in a unit administration form, as a mixture with standard pharmaceutical excipients, to man and animals for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention can be used in creams, gels, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Croscaramellose sodium | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathologies indicated above, which comprises the administration, to a patient, of an effective dose of a compound according to the invention, or a pharmaceutically acceptable salt or solvate thereof.

What is claimed is:

1. A compound of formula (I):

$$\text{(I)}$$

wherein
R1 represents a (C1-C4)alkyl group,
R2 represents —(CH$_2$)$_{n'}$—B wherein n'=0, 1, 2, 3, or 4, and B is a (C3-C5)-cycloalkyl group or a (C1-C4)alkyl group optionally substituted with one or more fluorine atoms or a (C1-C4)alkoxy group,
U represents a carbonyl group or a —CH$_2$— group,
Y, Z, V and W represent, independently of each other, a —CH— group, a carbon atom optionally substituted with a group R7, heteroatom selected from the group consisting of a nitrogen atom, a sulfur atom and an oxygen atom, or no atom, wherein the ring comprising Y, Z, V, and W is aromatic and 5- or 6-membered,
R3 and R4 represent, independently of each other, a hydrogen atom or a linear (C1-C4)alkyl group, or R3 and R4 form, together with the carbon to which they are attached, a (C3-C5)cycloalkyl group,
m is an integer equal to 1, 2, 3, or 4,
R5 represents a hydrogen atom or a (C1-C4)alkyl group,
R6 represents —(CH$_2$)$_n$-L wherein n=0, 1, 2, or 3, and L is a group independently selected from the group consisting of:
a (C1-C5)alkyl group optionally substituted with a (C1-C4)alkoxy group,
a (C3-C5)cycloalkyl group,
a phenyl group optionally substituted with one or more halogen atoms,
a 5- or 6-membered heteroaryl containing at least one heteroatom selected from the group consisting of a nitrogen atom and a sulfur atom, optionally substituted with a (C1-C4)alkyl group, and
a saturated heterocycle, wherein the said heterocycle is 4- to 7-membered containing at least one heteroatom selected from the group consisting of a nitrogen atom and an oxygen atom, and is optionally substituted in any position, including on the nitrogen atom, with one or more substituents selected from the group consisting of a fluorine atom, a (C1-C4)fluoroalkyl group, a linear or branched (C1-C4)alkyl group, a (C3-C5) cycloalkyl group and a (C1-C4)alkylsulfonamide group, the absolute configuration of a carbon substituted on the said heterocycle possibly being R or S, or racemic, and
R7 represents a hydrogen atom, a (C1-C4)alkyl group or a halogen atom,
in the form of a base or an acid-addition salt thereof, or in the form of an enantiomer or diastereoisomer thereof.

2. The compound according to claim 1, wherein
R1 represents a (C1-C4)alkyl group,
R2 represents —(CH$_2$)$_{n'}$—B wherein n'=0 or 1, and B is a (C3-C5)cycloalkyl group or a (C1-C4)alkyl group optionally substituted with one or more fluorine atoms or a (C1-C4)alkoxy group,
U represents a carbonyl group or a —CH$_2$— group,
Y, Z, V and W represent, independently of each other, a —CH— group, a carbon atom optionally substituted with a group R7, a heteroatom selected from the group consisting of a nitrogen atom and a sulfur atom, or no atom, wherein the ring comprising Y, Z, V, and W is aromatic and 5- or 6-membered, and
R6 represents —(CH$_2$)$_n$-L wherein n=0, 1, 2, or 3, and L is a group independently selected from the group consisting of:
a (C1-C5)alkyl group optionally substituted with a (C1-C4)alkoxy group,
(C3-C5)cycloalkyl group,
an aryl comprising 6 carbon atoms and optionally substituted with one or more halogen atoms,
a 5- or 6-membered heteroaryl containing at least one heteroatom selected from the group consisting of a nitrogen atom and a sulfur atom, optionally substituted with a (C1-C4)alkyl group, and
a saturated heterocycle, wherein the heterocycle is 5- to 7-membered containing at least one heteroatom selected from the group consisting of a nitrogen atom and an oxygen atom, and is optionally substituted in any position, including on the nitrogen atom, with one or more substituents selected from the group consisting of a fluorine atom, a (C1-C4)fluoroalkyl group, a linear or branched (C1-C4)alkyl group, a (C3-C5) cycloalkyl group and a (C1-C4)alkylsulfonamide group, the absolute configuration of a carbon substituted on the said heterocycle possibly being R or S, or racemic.

3. The compound according to claim 1, wherein U represents a carbonyl group.

4. The compound according to claim 1, wherein the ring comprising Y, Z, V and W is chosen from phenyl, pyridine, thiazole and thiophene groups.

5. The compound according to claim 1, wherein R3, R4 and R5 each represents a hydrogen atom.

6. The compound according to claim 1, wherein the chain —[C(R3R4)]$_m$-U—N(R5)(R6) is in the para or meta position relative to the ring to which it is attached.

7. The compound according to claim 1, selected from the group consisting of:
2-amino-1-ethyl-N-methyl-4-oxo-7-{4-[2-oxo-2-(phenylamino)ethyl]phenyl}-1,4-dihydro-1,8-naphthyridine-3-carboxamide,
2-amino-1-ethyl-7-[4-(2-{[(1-ethylpyrrolidin-2-yl)methyl](methyl)amino}-2-oxoethyl)phenyl]-N-methyl-4-oxo-1,4-dihydro-1,8-naphthyridine-3-carboxamide, 2-amino-1-ethyl-N-methyl-4-oxo-7-{4-[2-oxo-2-(pyrid-3-ylamino)ethyl]phenyl}-1,4-dihydro-1,8-naphthyridine-3-carboxamide, 2-amino-1-ethyl-N-methyl-4-oxo-7-{4-[2-oxo-2-(pyrid-2-ylamino)ethyl]phenyl}-1,4-dihydro-1,8-naphthyridine-3-carboxamide, 2-amino-7-(4-{2-[(2-chlorophenyl)amino]-2-oxoethyl}phenyl)-1-ethyl-N-methyl-4-oxo-1,4-dihydro-1,8-naphthyridine-3-carboxamide, 2-amino-7-(4-{2-[(3,5-difluorophenyl)amino]-2-oxoethyl}phenyl)-1-ethyl-N-methyl-4-oxo-1,4-dihydro-1,8-naphthyridine-3-carboxamide, 2-amino-1-ethyl-N-methyl-4-oxo-7-(4-{2-oxo-2-[(pyrid-4-ylmethyl)amino]ethyl}-phenyl)-1,4-dihydro-1,8-naphthyridine-3-carboxamide, 2-amino-1-ethyl-N-methyl-4-oxo-7-(4-{2-oxo-2-[(pyrid-2-ylmethyl)amino]ethyl}-phenyl)-1,4-dihydro-1,8-naphthyridine-3-carboxamide, 2-amino-1-ethyl-7-(4-{2-[(2-methoxyethyl)amino]-2-oxoethyl}phenyl)-N-methyl-4-oxo-1,4-dihydro-1,8-naphthyridine-3-carboxamide, 2-amino-7-{4-[2-(cyclopropylamino)-2-oxoethyl]phenyl}-1-ethyl-N-methyl-4-oxo-1,4-dihydro-1,8-naphthyridine-3-carboxamide, 2-amino-1-ethyl-N-methyl-7-(4-{2-[(1-methylethyl)amino]-2-oxoethyl}phenyl)-4-oxo-1,4-dihydro-1,8-naphthyridine-3-carboxamide, 2-amino-7-{4-[2-(cyclopentylamino)-2-oxoethyl]phenyl}-1-ethyl-N-methyl-4-oxo-1,4-dihydro-1,8-naphthyridine-3-carboxamide, 2-amino-1-ethyl-N-methyl-4-oxo-7-{4-[2-oxo-2-(pyrazin-2-ylamino)ethyl]phenyl}-1,4-dihydro-1,8-naphthyridine-3-carboxamide, 2-amino-1-ethyl-7-{4-[2-({[(2R)-1-ethylpyrrolidin-2-yl]methyl}amino)-2-oxoethyl]-phenyl}-N-methyl-4-oxo-1,4-dihydro-1,8-naphthyridine-3-carboxamide, 2-amino-1-ethyl-7-{4-[2-({[(2S)-1-ethylpyrrolidin-2-yl]methyl}amino)-2-oxoethyl]-phenyl}-N-methyl-4-oxo-1,4-dihydro-1,8-naphthyridine-3-carboxamide, 2-amino-1-ethyl-N-methyl-4-oxo-7-{4-[2-oxo-2-(pyrimidin-4-ylamino)ethyl]phenyl}-1,4-dihydro-1,8-naphthyridine-3-carboxamide, 2-amino-1-ethyl-N-methyl-4-oxo-7-{4-[2-oxo-2-(pyrid-4-ylamino)ethyl]phenyl}-1,4-dihydro-1,8-naphthyridine-3-carboxamide, 2-amino-1-ethyl-N-methyl-7-(4-{2-[(2-morpholin-4-yl-ethyl)amino]-2-oxoethyl}phenyl)-4-oxo-1,4-dihydro-1,8-naphthyridine-3-carboxamide, 2-amino-1-ethyl-N-methyl-4-oxo-7-{4-[2-oxo-2-(pyrid-2-ylamino)ethyl]pyrid-2-yl}-1,4-dihydro-1,8-naphthyridine-3-carboxamide, 2-amino-1-ethyl-N-methyl-7-{4-[1-methyl-2-oxo-2-(pyrid-2-ylamino)ethyl]phenyl}-4-oxo-1,4-dihydro-1,8-naphthyridine-3-carboxamide, 2-amino-1-ethyl-N-methyl-4-oxo-7-{6-[2-oxo-2-(pyrid-2-ylamino)ethyl]pyrid-3-yl}-1,4-dihydro-1,8-naphthyridine-3-carboxamide, 2-amino-1-ethyl-7-[4-(2-{[(4-ethylmorpholin-3-yl)methyl]amino}-2-oxoethyl)phenyl]-N-methyl-4-oxo-1,4-dihydro-1,8-naphthyridine-3-carboxamide, 2-amino-1-ethyl-7-[6-(2-{[(4-ethylmorpholin-3-yl)methyl]amino}-2-oxoethyl)pyrid-3-yl]-N-methyl-4-oxo-1,4-dihydro-1,8-naphthyridine-3-carboxamide, 2-amino-1-ethyl-7-{4-[2-({[(2S)-1-ethyl-4,4-difluoropyrrolidin-2-yl]methyl}amino)-2-oxoethyl]phenyl}-N-methyl-4-oxo-1,4-dihydro-1,8-naphthyridine-3-carboxamide, 2-amino-1-ethyl-7-[4-(2-{[(4-ethylmorpholin-3-yl)methyl]amino}-methyl-2-oxoethyl)phenyl]-N-methyl-4-oxo-1,4-dihydro-1,8-naphthyridine-3-carboxamide, 2-amino-1-ethyl-7-{4-[2-({[(2S,4R)-1-ethyl-4-fluoropyrrolidin-2-yl]methyl}amino)-2-oxoethyl]phenyl}-N-methyl-4-oxo-1,4-dihydro-1,8-naphthyridine-3-carboxamide, 2-amino-1-ethyl-7-{4-[2-({[(2R)-1-(2-fluoroethyl)pyrrolidin-2-yl]methyl}amino)-2-oxoethyl]phenyl}-N-methyl-4-oxo-1,4-dihydro-1,8-naphthyridine-3-carboxamide, 2-amino-1-ethyl-N-methyl-7-{4-[2-({[(2R)-1-(methylsulfonyl)pyrrolidin-2-yl]methyl}-amino)-2-oxoethyl]phenyl}-4-oxo-1,4-dihydro-1,8-naphthyridine-3-carboxamide, 2-amino-1-ethyl-7-{5-[2-({[(2R)-1-(2-fluoroethyl)pyrrolidin-2-yl]methyl}amino)-2-oxoethyl]pyrid-2-yl}-N-methyl-4-oxo-1,4-dihydro-1,8-naphthyridine-3-carboxamide, 2-amino-1-ethyl-N-methyl-4-oxo-7-{4-[2-oxo-2-({[(2R)-1-(2,2,2-trifluoroethyl)pyrrolidin-2-yl]methyl}amino)ethyl]phenyl}-1,4-dihydro-1,8-naphthyridine-3-carboxamide, 2-amino-7-{4-[2-({[(2R)-1-(2,2-difluoroethyl)pyrrolidin-2-yl]methyl}amino)-2-oxoethyl]-phenyl}-1-ethyl-N-methyl-4-oxo-1,4-dihydro-1,8-naphthyridine-3-carboxamide, 2-amino-1-ethyl-N-methyl-7-{4-[2-({[4-(1-methylethyl)morpholin-3-yl]methyl}amino)-2-oxoethyl]phenyl}-4-oxo-1,4-dihydro-1,8-naphthyridine-3-carboxamide, 2-amino-7-[4-(2-{[(4-cyclopropylmorpholin-3-yl)methyl]amino}-2-oxoethyl)phenyl]-1-ethyl-N-methyl-4-oxo-1,4-dihydro-1,8-naphthyridine-3-carboxamide, 2-amino-7-{5-[2-({[(2R)-1-(2,2-difluoroethyl)pyrrolidin-2-yl]methyl}amino)-2-oxoethyl]pyrid-2-yl}-1-ethyl-N-methyl-4-oxo-1,4-dihydro-1,8-naphthyridine-3-carboxamide, 2-amino-1-ethyl-N-methyl-4-oxo-7-{4-[2-oxo-2-(1,3-thiazol-2-ylamino)ethyl]phenyl}-1,4-dihydro-1,8-naphthyridine-3-carboxamide, 2-amino-1-ethyl-N-methyl-7-[4-(2-{[(1-methyl-1H-imidazol-5-yl)methyl]amino}-2-oxoethyl)phenyl]-4-oxo-1,4-dihydro-1,8-naphthyridine-3-carboxamide, 2-amino-1-ethyl-N-methyl-4-oxo-7-(4-{2-oxo-2-[(2-pyrid-3-ylethyl)amino]ethyl}-phenyl)-1,4-dihydro-1,8-naphthyridine-3-carboxamide, 2-amino-1-ethyl-N-methyl-7-(4-{2-[(3-morpholin-4-yl-propyl)amino]-2-oxoethyl}-phenyl)-4-oxo-1,4-dihydro-1,8-naphthyridine-3-carboxamide, 2-amino-1-ethyl-N-methyl-4-oxo-7-(4-{2-oxo-2-[(2-pyrid-2-ylethyl)amino]ethyl}-phenyl)-1,4-dihydro-1,8-naphthyridine-3-carboxamide, 2-amino-1-ethyl-N-methyl-4-oxo-7-(4-{2-oxo-2-[(2-phenylethyl)amino]ethyl}phenyl)-1,4-dihydro-1,8-naphthyridine-3-carboxamide, 2-amino-1-ethyl-N-methyl-4-oxo-7-(4-{2-oxo-2-[3-phenylpropyl)amino]ethyl}phenyl)-1,4-dihydro-1,8-naphthyridine-3-carboxamide, 2-amino-1-ethyl-N-methyl-7-[4-(2-{[2-(1-methyl-1H-pyrrol-2-yl)ethyl]amino}-2-oxoethyl)phenyl]-4-oxo-1,4-dihydro-1,8-naphthyridine-3-carboxamide, 2-amino-1-ethyl-7-[4-(2-{[(1-ethylpyrrolidin-2-yl)methyl]amino}-2-oxoethyl)-1,3-thiazol-2-yl]-N-methyl-4-oxo-1,4-dihydro-1,8-naphthyridine-3-carboxamide, 2-amino-1-(3-methoxypropyl)-N-methyl-4-oxo-7-{4-[2-oxo-2-(pyrid-2-ylamino)ethyl]-phenyl}-1,4-dihydro-1,8-naphthyridine-3-carboxamide, 2-amino-7-[4-(2-{[1-(2,2-difluoroethyl)pyrrolidin-3-yl]
    amino}-2-oxoethyl)phenyl]-1-ethyl-N-methyl-4-oxo-
    1,4-dihydro-1,8-naphthyridine-3-carboxamide,
2-amino-1-ethyl-7-[4-(3-{[(1-ethylpyrrolidin-2-yl)me-
    thyl]amino}-3-oxopropyl)phenyl]-N-methyl-4-oxo-1,
    4-dihydro-1,8-naphthyridine-3-carboxamide,
2-amino-1-ethyl-7-[4-(4-{[(1-ethylpyrrolidin-2-yl)me-
    thyl]amino}-4-oxobutyl)phenyl]-N-methyl-4-oxo-1,4-
    dihydro-1,8-naphthyridine-3-carboxamide,
2-amino-1-ethyl-7-[4-(2-{[(1-ethylpyrrolidin-2-yl)me-
    thyl]amino}-2-oxoethyl)phenyl]-4-oxo-N-propyl-1,4-
    dihydro-1,8-naphthyridine-3-carboxamide,
2-amino-7-[4-(2-{[(1-ethylpyrrolidin-2-yl)methyl]
    amino}-2-oxoethyl)phenyl]-N-methyl-4-oxo-1-(2,2,2-
    trifluoroethyl)-1,4-dihydro-1,8-naphthyridine-3-car-
    boxamide,
2-amino-1-cyclopentyl-7-[4-(2-{[(1-ethylpyrrolidin-2-yl)
    methyl]amino}-2-oxoethyl)phenyl]-N-methyl-4-oxo-
    1,4-dihydro-1,8-naphthyridine-3-carboxamide,
2-amino-1-ethyl-7-[4-(5-{[(1-ethylpyrrolidin-2-yl)me-
    thyl]amino}-5-oxopentyl)phenyl]-N-methyl-4-oxo-1,
    4-dihydro-1,8-naphthyridine-3-carboxamide,
1-ethyl-7-[5-(2-{[(1-ethylpyrrolidin-2-yl)methyl]amino}-
    2-oxoethyl)thiophen-2-yl]-N,2-dimethyl-4-oxo-1,4-di-
    hydro-1,8-naphthyridine-3-carboxamide,
2-amino-7-{4-[2-({[(2R)-1-ethyl pyrrolidin-2-yl]
    methyl}amino)-2-oxoethyl]phenyl}-N-methyl-1-(2-
    methylpropyl)-4-oxo-1,4-dihydro-1,8-naphthyridine-
    3-carboxamide,
2-amino-1-ethyl-7-{4-[1-({[(2R)-1-ethylpyrrolidin-2-yl]
    methyl}carbamoyl)cyclopropyl]-phenyl}-N-methyl-4-
    oxo-1,4-dihydro-1,8-naphthyridine-3-carboxamide,
2-amino-1-ethyl-7-{2-[2-({[(2R)-1-ethylpyrrolidin-2-yl]
    methyl}amino)-2-oxoethyl]-1,3-thiazol-4-yl}-N-me-
    thyl-4-oxo-1,4-dihydro-1,8-naphthyridine-3-carboxa-
    mide,
2-amino-1-ethyl-7-{4-[2-({[(2R)-1-ethylpyrrolidin-2-yl]
    methyl}amino)-2-oxoethyl]-2-fluorophenyl}-N-me-
    thyl-4-oxo-1,4-dihydro-1,8-naphthyridine-3-carboxa-
    mide,
2-amino-7-[3-chloro-4-(2-{[(1-ethylpyrrolidin-2-yl)me-
    thyl]amino}-2-oxoethyl)phenyl]-1-ethyl-N-methyl-4-
    oxo-1,4-dihydro-1,8-naphthyridine-3-carboxamide,
2-amino-7-[3-fluoro-4-(2-{[(1-ethylpyrrolidin-2-yl)me-
    thyl]amino}-2-oxoethyl)phenyl]-1-ethyl-N-methyl-4-
    oxo-1,4-dihydro-1,8-naphthyridine-3-carboxamide,
2-amino-7-[3-methyl-4-(2-{[1-ethylpyrrolidin-2-yl)me-
    thyl]amino}-2-oxoethyl)phenyl]-1-ethyl-N-methyl-4-
    oxo-1,4-dihydro-1,8-naphthyridine-3-carboxamide,
2-amino-1-(cyclopropylmethyl)-7-[4-(2-{[(1-ethylpyrro-
    lidin-2-yl)methyl]amino}-2-oxoethyl)phenyl]-N-me-
    thyl-4-oxo-1,4-dihydro-1,8-naphthyridine-3-carboxa-
    mide,
2-amino-1-ethyl-7-[4-(2-{[(1-ethyl pyrrolidin-2-yl)me-
    thyl]amino}-2-oxoethyl)-2-methylphenyl]-N-methyl-
    4-oxo-1,4-dihydro-1,8-naphthyridine-3-carboxamide;
2-amino-1-ethyl-7-[3-(2-{[(1-ethyl pyrrolidin-2-yl)me-
    thyl]amino}-2-oxoethyl)phenyl]-N-methyl-4-oxo-1,4-
    dihydro-1,8-naphthyridine-3-carboxamide,
2-amino-1-ethyl-N-methyl-4-oxo-7-{3-[2-oxo-2-(pyrid-
    2-ylamino)ethyl]phenyl}-1,4-dihydro-1,8-naphthyri-
    dine-3-carboxamide, and
2-amino-1-ethyl-N-methyl-4-oxo-7-{4-[2-(pyrid-2-
    ylamino)ethyl]phenyl}-1,4-dihydro-1,8-naphthyridine-
    3-carboxamide.

8. A process for preparing the compound according to claim 1, comprising the step of reacting a compound of formula (XI):

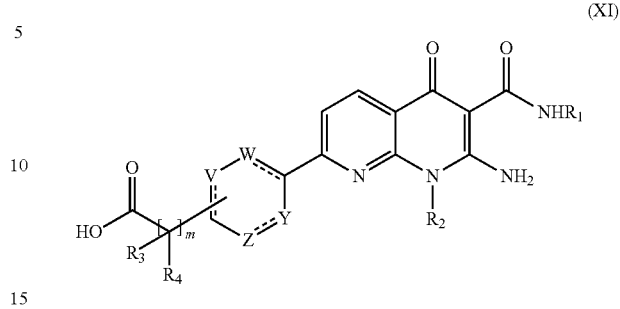

(XI)

with a compound of formula HNR5R6, in the presence of a coupling agent and a base, wherein R1, R2, R3, R4, R5, R6, V, W, Y, Z and m are as defined in claim 1.

9. A process for preparing the compound according to claim 1, comprising the step of reacting a compound of formula (VII):

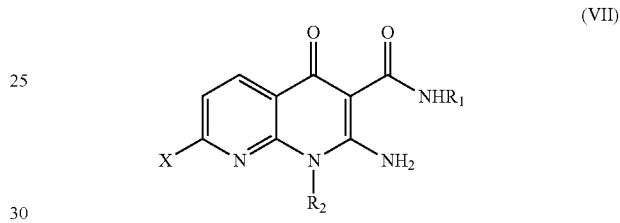

(VII)

with a compound of formula (IXa)

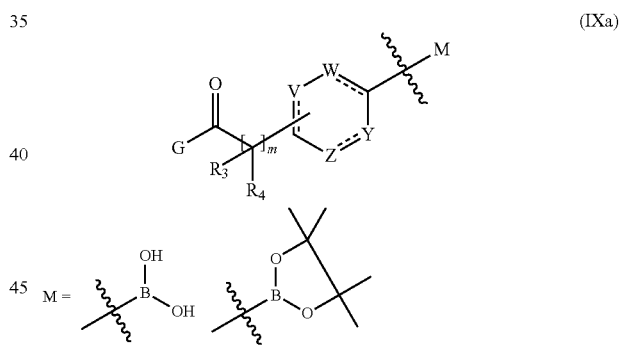

(IXa)

wherein X represents a halogen atom,
    G represents a (C1-C4)alkoxy group or a group —NR5R6, and
    R1, R2, R3, R4, R5, R6, V, W, Y, Z and m are as defined in, claim 1.

10. A process for preparing the compound according to claim 1, comprising reacting a compound of formula (VII):

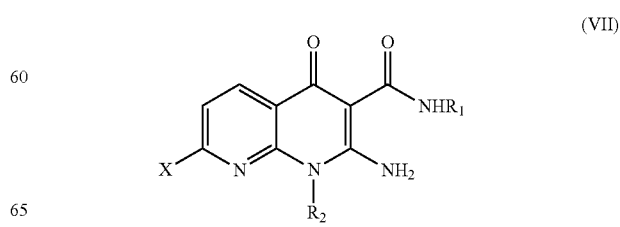

(VII)

with a compound of formula (IXb):

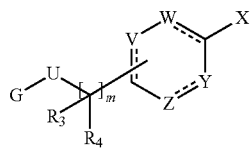

wherein G represents a (C1-C4)alkoxy group or a group —NR5R6, X represents a halogen atom and R1, R2, R3, R4, R5, R6, V, W, Y, Z and m are as defined in claim 1.

11. A pharmaceutical composition, comprising the compound according to claim 1, or a pharmaceutically acceptable salt thereof, and at least one pharmaceutically acceptable excipient.

12. A method for treating a leukaemia, comprising administering to a patient in need thereof an effective dose of the compound according to claim 1.

13. A composition comprising at least one compound according to claim 1 and at least one chemotherapy agent.

* * * * *